US011862299B2

(12) United States Patent
Yin et al.

(10) Patent No.: US 11,862,299 B2
(45) **Date of Patent: *Jan. 2, 2024**

(54) ALGORITHMS FOR SEQUENCE DETERMINATIONS

(71) Applicant: GEN-PROBE INCORPORATED, San Diego, CA (US)

(72) Inventors: Tongjia Yin, San Diego, CA (US); Steven T. Brentano, San Diego, CA (US); Jennifer Bungo, San Diego, CA (US); Xianqun Wang, San Diego, CA (US); Michael Hadjisavas, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 1236 days.

This patent is subject to a terminal disclaimer.

(21) Appl. No.: 16/175,742

(22) Filed: Oct. 30, 2018

(65) Prior Publication Data

US 2019/0121941 A1 Apr. 25, 2019

Related U.S. Application Data

(63) Continuation of application No. 14/346,954, filed as application No. PCT/US2012/057237 on Sep. 26, 2012, now Pat. No. 10,152,569.

(60) Provisional application No. 61/539,440, filed on Sep. 26, 2011.

(51) Int. Cl.
*G16B 30/00* (2019.01)
*G16B 30/10* (2019.01)

(52) U.S. Cl.
CPC ............ *G16B 30/00* (2019.02); *G16B 30/10* (2019.02)

(58) Field of Classification Search
None
See application file for complete search history.

(56) References Cited

U.S. PATENT DOCUMENTS

| | | | |
|---|---|---|---|
| 10,152,569 | B2 | 12/2018 | Yin et al. |
| 2003/0200033 | A1 | 10/2003 | Segal et al. |
| 2010/0169026 | A1 | 7/2010 | Sorenson et al. |

FOREIGN PATENT DOCUMENTS

| | | | |
|---|---|---|---|
| WO | WO 2013/049135 | A1 | 4/2013 |

OTHER PUBLICATIONS

Jeck et al., "Extending assembly of short DNA sequences to handle error," *Bioinformatics*, 23(21): 2942-2944, (2007).
Bryant Jr. et al., "QSRA â a quality-value guided de novo short read assembler," *BMC Bioinformatics*, Biomed Central, 10(1): 69, (2009).
Dohm et al., "SHARCGS, a fast and highly accurate short-read assembly algorithm for de novo genomic sequencing," *Genome Research*, Cold Spring Harbor Laboratory Press, 17(1): 1697-1706, (2007).
PCT International Search Report and Written Opinion of the International Searching Authority, for application PCT/US2012/057237 dated Dec. 21, 2012.
PCT International Preliminary Report on Patentability for application PCT/US2012/057237 dated Apr. 1, 2014.
U.S. Appl. No. 14/346,954 Non-Final Office Action dated Oct. 8, 2015.
U.S. Appl. No. 14/346,954 Final Office Action dated May 17, 2016.
U.S. Appl. No. 14/346,954 Advisory dated Aug. 2, 2016.
U.S. Appl. No. 14/346,954 Non-Final Office Action dated May 22, 2017.
U.S. Appl. No. 14/346,954 Final Office Action dated Dec. 1, 2017.
U.S. Appl. No. 14/346,954 Notice of Allowance dated Jul. 30, 2018.

*Primary Examiner* — Joseph Woitach
(74) *Attorney, Agent, or Firm* — Alston & Bird LLP; Jeff Landes

(57) ABSTRACT

The invention provides methods of determining a consensus sequence from multiple raw sequencing reads of a nucleic acid target. The nucleic acid target includes an anchor segment of known sequence and an adjacent segment of unknown sequence. The anchor segment provides a means to assess the quality of a raw target sequencing read. Raw target sequencing reads meeting or exceeding a threshold are assigned to an accepted class. The consensus sequence of the adjacent segment can be determined from raw target sequencing reads in the accepted class. Successive polling steps determine successive consensus nucleobases in a nascent sequence of the adjacent segment. Raw target sequencing reads can be removed or reintroduced from the accepted class depending on their correspondence to the most recently determined consensus nucleobase and/or the nascent sequence.

10 Claims, 8 Drawing Sheets

Specification includes a Sequence Listing.

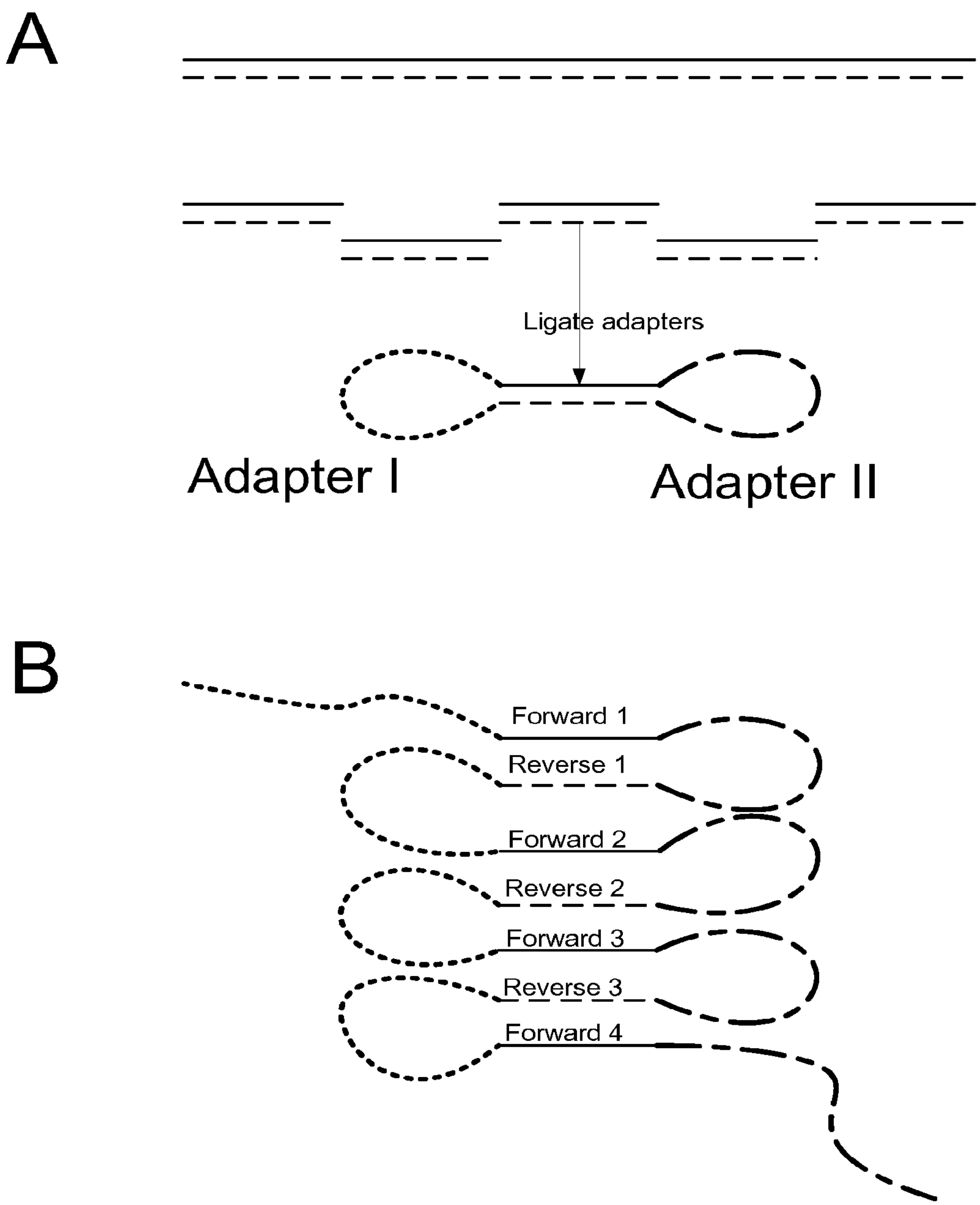
*FIGS. 3A, B*

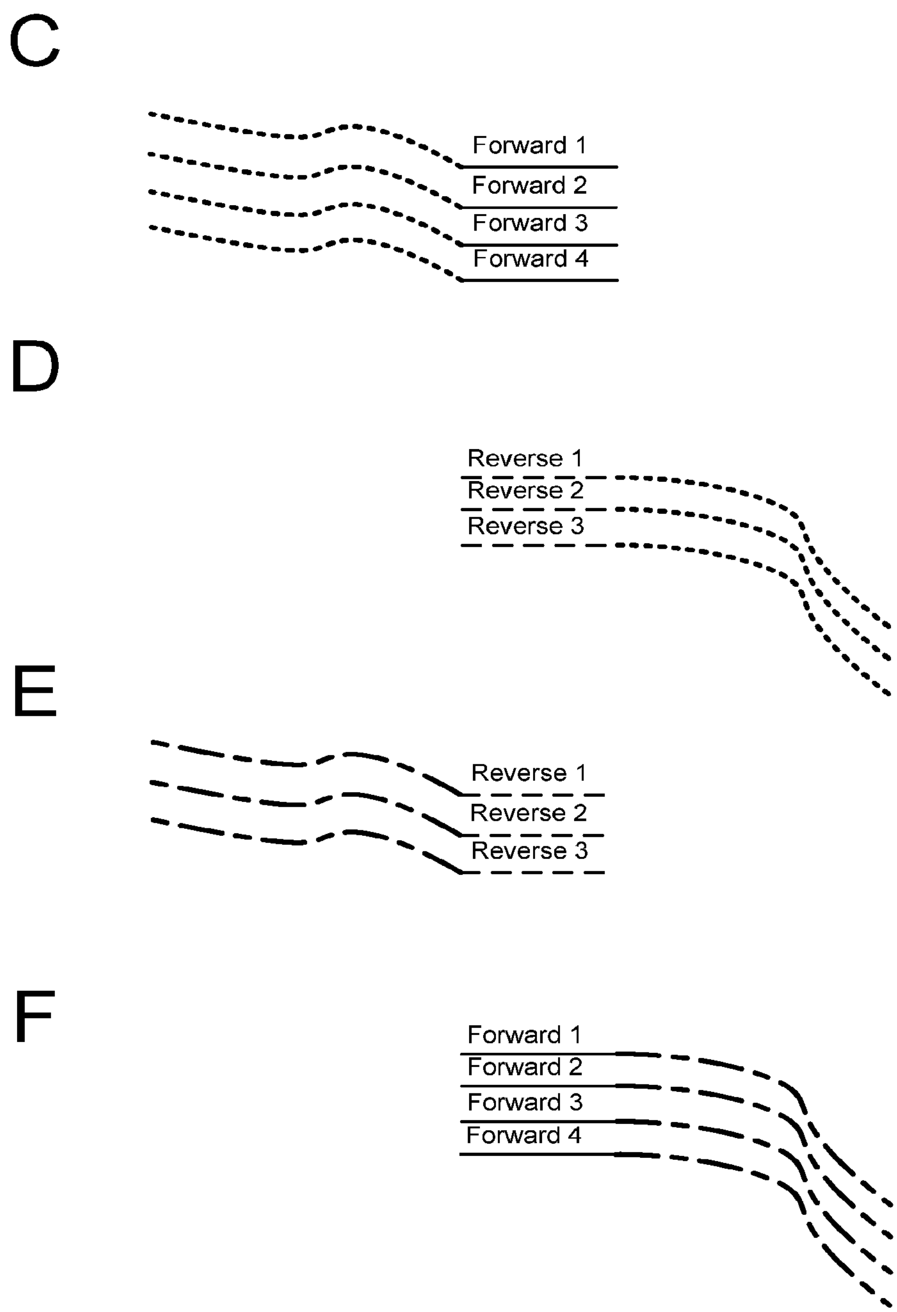
*FIGS. 3C-F*

SEQUENCE LISTING

```
<160> NUMBER OF SEQ ID NOS: 74

<210> SEQ ID NO 1
<211> LENGTH: 12
<212> TYPE: DNA
<213> ORGANISM: Artificial Sequence
<220> FEATURE:
<223> OTHER INFORMATION: Synthesized

<400> SEQUENCE: 1

cgcggaaacc gg                                                          12


<210> SEQ ID NO 2
<211> LENGTH: 13
<212> TYPE: DNA
<213> ORGANISM: Artificial Sequence
<220> FEATURE:
<223> OTHER INFORMATION: Synthesized

<400> SEQUENCE: 2

cgactgaacc tgg                                                         13


<210> SEQ ID NO 3
<211> LENGTH: 10
<212> TYPE: DNA
<213> ORGANISM: Artificial Sequence
<220> FEATURE:
<223> OTHER INFORMATION: Synthesized
```

<400> SEQUENCE: 3
ctgcggtgag 10

<210> SEQ ID NO 4
<211> LENGTH: 12
<212> TYPE: DNA
<213> ORGANISM: Artificial Sequence
<220> FEATURE:
<223> OTHER INFORMATION: Synthesized

<400> SEQUENCE: 4
cctgcgaacc gg 12

<210> SEQ ID NO 5
<211> LENGTH: 14
<212> TYPE: DNA
<213> ORGANISM: Artificial Sequence
<220> FEATURE:
<223> OTHER INFORMATION: Synthesized

<400> SEQUENCE: 5
tctgcggaca ccgg 14

<210> SEQ ID NO 6
<211> LENGTH: 14
<212> TYPE: DNA
<213> ORGANISM: Artificial Sequence
<220> FEATURE:
<223> OTHER INFORMATION: Synthesized

<400> SEQUENCE: 6
ctggcggaac acag 14

<210> SEQ ID NO 7
<211> LENGTH: 15
<212> TYPE: DNA
<213> ORGANISM: Artificial Sequence
<220> FEATURE:
<223> OTHER INFORMATION: Synthesized

<400> SEQUENCE: 7
ctttcggaac gcagg 15

<210> SEQ ID NO 8
<211> LENGTH: 15
<212> TYPE: DNA
<213> ORGANISM: Artificial Sequence
<220> FEATURE:
<223> OTHER INFORMATION: Synthesized

<400> SEQUENCE: 8
ctgacggaaa cccgg 15

<210> SEQ ID NO 9
<211> LENGTH: 11
<212> TYPE: DNA
<213> ORGANISM: Artificial Sequence
<220> FEATURE:
<223> OTHER INFORMATION: Synthesized

<400> SEQUENCE: 9
ctgcgggacg g 11

<210> SEQ ID NO 10
<211> LENGTH: 164

<212> TYPE: DNA
<213> ORGANISM: Hepatitis C virus

<400> SEQUENCE: 10
ctgcggaacc ggtgagtaca ccggaattgc caggacgacc gggtcctttc gtggataaac 60
ccgctcaatg cctggagatt tgggcgtgcc cccgcaagac tgctagccga gtagtgttgg 120
gtcgcgaaag gccttgtggt actgcctgat agggtgcttg cgag 164

<210> SEQ ID NO 11
<211> LENGTH: 45
<212> TYPE: DNA
<213> ORGANISM: Artificial Sequence
<220> FEATURE:
<223> OTHER INFORMATION: Synthesized

<400> SEQUENCE: 11
atctctctca acaacaacaa cggaggagga ggaaaagaga gagat 45

<210> SEQ ID NO 12
<211> LENGTH: 16
<212> TYPE: DNA
<213> ORGANISM: Artificial Sequence
<220> FEATURE:
<223> OTHER INFORMATION: Synthesized

<400> SEQUENCE: 12
aaaaaaaaaa aaaaaa 16

<210> SEQ ID NO 13
<211> LENGTH: 482
<212> TYPE: DNA
<213> ORGANISM: Artificial Sequence
<220> FEATURE:
<223> OTHER INFORMATION: Synthesized

<400> SEQUENCE: 13
tgcagcaggg cggctgctga gagtgatggt cgcgacactt gactcgcagg gtgacaagaa 60
agcgcctctc ccccattgcc tcttgtaaaa tccacgagaa caagaccgcc atccgaccca 120
aacaaaaacg acactcaaaa aacagccacc aaaaaaacaa gcacagaagc aaccaaaaga 180
aaccaccaac cacacccagg aaaaaaaaaa caaaaaaaaa caaaaaaaaa acaaaaaaaa 240
aaccacaccc acacatcatc tacaaacaac aaaaaagacc gaaaaaaaaa aaagatcgga 300
cccaccacca ataacctata caaccactta agaacgcgca gccaccccca tccacgaaca 360
aaaaacacaa cagccaaaga acaccaaaaa aaaaaaacaa aaaaaaaaaa aaaaaaaaaa 420
aaaaaaaaaa aaaacaacaa aaaaaaaagc tggacgtgct tgccgaatgc gcggtggcgc 480
tt 482

<210> SEQ ID NO 14
<211> LENGTH: 4664
<212> TYPE: DNA
<213> ORGANISM: Artificial Sequence
<220> FEATURE:
<223> OTHER INFORMATION: Synthesized

<400> SEQUENCE: 14
ggccgctctg tccagcgatt cgccgtgtta ccgtaatcgc tcaaggcagc cctcacgctt 60
cagcgcggtg tctgtaggat agatctttcc gagcgacaga gtggacggcc ctcgaagagg 120
actggcccgg cctcgagcct gagatctgcg ttaatggctc ccgatagagt ccgtcggcta 180

-continued

```
gtggttggag ctctcgcgcg ctcctaataa ctcgctgcgc ttcctcgcag cagcaatcta    240
cgcgtccact cttcagctca gactaacaac ctcgcgaaga cggaaggaga agaggcagta    300
tagggatgag gtcatcgcga aggccgcatc tatgcgcgag gaaaccggtg agtaacaccg    360
cgggtgcatc cgtgtattgt atagatctct gtgccgagca ccacaacaac ggaagggtcg    420
ccgttacggg aaaagcagaa acgagaactc ggataaacct ttatcttggc tcattcgcac    480
ggctctcggg acctgcctct cgagatagag gaatatgcgg tagacgcgct cgcgaaagga    540
cctcagcggc attcttttct tacacataca gctcttttta ttctgcgcca cgccgacagg    600
tctcccccag atcccttctt caacctaacc agagctacaa gctcttggcg gggaaggcgg    660
cggcgacgcg catctgtaga tacgcggcgg cggtgtatag ttctccgacg cggtacgcgg    720
tcactcctgg catgctcgca agggtgtaac ttagatagct ccgggtttcc cccgacttcc    780
ccaggcctgg cagtaggagt aggcgtcctt tgcgttagat tcttcgtttc tgcctacaaa    840
caaaccacaa acacgccaga tcgaggaatg tgaggaacca cgagccgcaa gaactccatc    900
cgcacgcgcc tacacccgag tactatttgg ttcggggcgt gggtgaccca ttccaccggc    960
ctgtgatcga caggacccct ataggcatct atactctcgg agcctggata tcgtacggtg   1020
gctttggcgg gggtcggacc ggcatatatc tctccatgcg tcatcttaga gcacaggcag   1080
tatttcggta cacagaaaaa ggacgagaca ggacgagtcg tcctgtgcaa ttctggctcg   1140
tagctcacac cggtcagtcc gcagactgct ctctcaacca aacacgagac gcaggtaggt   1200
tatggccaaa aggaagaccg aggatttcaa actctctggc cggaaccgcg tgggacagtt   1260
cacctttcgg cgcacgccaa tctggcagtg ctattgtcgc aggcgcccgg ggttcatcta   1320
aacggatcgc tcgatatctt aaatcctcgc gctacaatgc cttccggtgg aatgtaactt   1380
caccgtcctt ctggggccag atagcccctc accgccaaga accaaccaac gagggaggag   1440
aaagaactgg acatttaccc agaccgtgtg gatgtgcatc cgcgaccggc ttagatggtc   1500
ctcaaggctg agcctggatt cctgtgtcgg tgcttaatcg cgccgctcac attccttctc   1560
gatatctgga gacaacagga cggaggtagg agggaaaaga gcgagggaag gtccctcgcc   1620
aagcacccta tcaggcagta ccacaggcct ttcgcgaccc aacactactt cgggcaagac   1680
ttctaacgca gtaccttgag tgacgggggc acggtccaaa tctcccaggc attgagcggg   1740
tatccacgaa aaaggacccg gtcgtcctgg caatttccgg tgtctcaccg gttccgcaga   1800
atcttctctc aaacaacaac aacggaggag gaggaaatcg gcaggagaag acgtgcgtgt   1860
ttacacgggt gtgtattaca caccggaatt gccaggacgg accctggtcc ttgtcggtga   1920
gtgaatacct ttcggcgtct acacactcgt cactcgagcg agaatctaaa ctaggcagag   1980
gaaagcgtaa ggaagagctc tccaaaagca ccttcctgca ctccgcaacg aacgtgctcg   2040
cttgttgtcg cagctcctgg gaaccactcg ccgaaggcct tcggtgggta ctctcttagg   2100
tcaggtgtgt cgcggttggg aggatcccct ctcaaacatc cacatttgag gcgttttttt   2160
aattcacgga aaaggacccg tcggttccac ccaaattccg ggtgtactca ccggtcccca   2220
gattcttcta ttcaacaaaa aacgagagga accaacggag gaggaggaaa agagagaaga   2280
tctcgcaagc accctaatca gagcaaggga tacggcgagg aacctacttg gcctttccgc   2340
ggccgaaccc gtggagttaa cccgaattca acacctagga cctggcggct aagcagtctt   2400
gcggggcgca tcgccagata ctaccacgcg ccttgcaacg gttctcacga aggaggaccc   2460
ggtcggtcct gggcaattcc ggtcgtactc acgccgagtg cacgcgatac tcaatgccgt   2520
caacgcaaca agcagaacgg aggccaggga ccgccgtttt gagttagatg agacgaggaa   2580
```

-continued

```
tctgcggacc ggtgagtaca ccgcataatt cgtgggccat ggatcgacac gctcaaggca   2640
agcatctgat tcgtggaatg gataaaaaga aaaccttctt ccgcaacgct caactgcctg   2700
gcagatttgg ctgacgttca ggcccccagc tcgcacagac actgcctttt cgcgacgcgt   2760
acgtctaccg agtagtcgtt gcgaggcgtt cttggtcggc cgaaggcccc aaactccagg   2820
gttgctcggt tggaagcctg ttttatccac cgaaggaacc gccgtcggtc ctgcatgctc   2880
cgtgataggc tcacgcgctt tcctcgggca tgtatggatc tttctccata cacaaagcaa   2940
caagcggaga ggcagggaaa gagagagcta atccccgcaa gcacaccgct atgcggcagt   3000
tgacgcaaga acagagagac agcgggcctt ctcgcttgga cgccaattca cactcagcct   3060
cggctagcaa gtcttgcggg gcacgccacc atctcaggtg cttgcatttg agcggtctga   3120
ttcccactgt atagcgaccc gcgctcgtcc tgggcaattc cgtgtacccc accggttccg   3180
cagatctctc tcaaccaaca acaaacggag gaggcagggg aaaagagaga gatgctgagg   3240
cggaagccgg tgagtaggcc accggaattg ccaggacgac gccggtcctt tcgtggataa   3300
aacccgctca atgcctgaag ttctgggcgt gcccgcaaga ctgctagccg agttagtgtt   3360
gtggtcgcga aatgggaggc ctgtggtact cggcctgata gggtgcttgc gagatctctc   3420
tcaacaaaca acaacggagg agaggaggaa agagacggca ggatccgcaa gcacccctac   3480
tcaggccagg tacgcacaag gcgctgttcg ccgaacgccc cacacctact ccggctagca   3540
gtcttggcgg ggggcagcgc ccaaatctcc aggcattgag cgggtttaat gccacgaaag   3600
gaccgccggt cgtcctggca attccgcgtg tactcagccg gtttcgcaga tctctcatca   3660
acaacaagca acgcgaggag gaggaaaagg agatgatctg cggacgcgtg aagtacaccg   3720
gaattgccag gacgaccggt ccttcctcgt ggataaacgc ccggcttcca aatgcgctgg   3780
ccagatttgg cggcgatggc ccgcaagact gctagccgag ttagtgttgg gtcgcgaagg   3840
ccttgtggta ctagccgtga gtagggtgct tgccgagatc tctctcccaa acaaccaaca   3900
acggaggagg aggaaaaaga gagagatcct cggcaagcac gccttatgca ggccagtacc   3960
acgaaggcct tcgcgacggc ggcaacaact actcggctac aaagactctt gggcgggggg   4020
gcacggccaa atctccaggc attgagcggg tttatccaac gaaaggacgc gcggtcgtcc   4080
tgggcaattc cggtgtagct cacggtttcc gccagaatct gctctcaaca agcaacacgg   4140
aggagggagg aaaagggggg gaaagagaga tctgcggaac cggtgagtac agccggaatt   4200
gccaggacgc aaccgggggt cctttcgtgg ataaacccgt caatgcctgg aagaatttgg   4260
gggcgtgccc ccgcaagact cgctaggccg agtagctgtt gggctgcggg cgaaaggcct   4320
tgtggtatct cgcctgatag gcgtcgcctt ggcgagatct ctgctcagcc caacagacag   4380
acggaggcag agaggaaaag agagagaatc ccttcgcaag cacgcctatc aggccagtac   4440
cacaaaggcc tttcgcgagc gcgtcaacac tagcctcgct aagcagtctt ggcgggggc   4500
agccaaatct cgcaggcatg aggcgggttt atccacgaaa ggacccggtc gtcgctgagc   4560
aattccgggt tagctcaccg gttccgcaga tctctctcaa caacaacaag ccaccaaacg   4620
gaggaggagg aaagagagag atctggcgga acgcgtgagt accg                     4664
```

<210> SEQ ID NO 15
<211> LENGTH: 3694
<212> TYPE: DNA
<213> ORGANISM: Artificial Sequence
<220> FEATURE:
<223> OTHER INFORMATION: Synthesized

<400> SEQUENCE: 15

```
ggtggagtac aagccacgga attggccacc gggacgacgc acgcagcacg acccgggtcc      60
atttcgtgga ataacccgct catgcctgga gatttgggcg tgccccccac cccgcaagac     120
tgctgccgag tagtgttggt cgccgaaagc gccttgtggc taagcctgcc gccctgatca     180
agcacgggtg cttgcgagat tcctctcaca acaacaccac ggatgaggag gccaaaagag     240
cagaactctc gccagcaccc tacttcaagg cagtaccacc aaggccttcc gcgacagccc     300
gcaacaccta ctccggccta gccagtcttg aagcgggcgg gcaaggcgcc caacgatcct     360
ccagggcatt ggccgggttt tatcccacga aaggactccg gcgtgcctgg cccattccgt     420
tgtactccac gcggcttccg cagctcctct cctccaaaca accaaccaaa aacgaagagg     480
aaggaggcaa aagagagaga tcatgcggaa ccaaggtgag tacaaaccag agaatataac     540
acaaggacag aaccaaaaaa gaagagaacc cattcataat cgatgataac acaaaccgct     600
ccacagacat ataaagaaga acgcacgaac acgcggcgcg tcgccaaacg ccaagatagc     660
gagtaagcca atagataaga gagcaaaaca aagtcagaca gagaagacca taatagagat     720
aacaaaaaaa aaaaaaaaaa aacataaaag ctgataagag aaaaaaaaga tgctacagag     780
aaaatatcat ctccatcaca caacacaaca cagagaggaa ggaaaggaaa agaagaagag     840
aagatacatg cagcacacta aatcaagaga aaaaaaccaa aaaaaagaca agataacaaa     900
aaaaaaaaaa aaaaaataca cacaaaaaca ccaaacacac acaacaaaca cacaccaaac     960
aacacacaaa caaaaaaaca aacaaaaaca ccaaaaaaaa agaaaaaaaa aaaaaacaaa    1020
aaaacaagac acaaacaaac aacaaaaaac caaaacaaaa aaacaaaaaa aaacaaaggc    1080
ctttcgccaa aagaaccaca acaactacaa aacagactag aacagatacc atataagcgg    1140
aggagcaaaa gcacaaatac aaaaaatacc aggcatattg aaagacaaag gcgataataa    1200
taaaccacga aaggaccggt cgtaaaacct ggcaatttcc ggcgtgtact caccgttccg    1260
cagatctctc ctcacccaac acaaccggac ggcaggaggc aaaagagaga gagatctgcg    1320
gaaccgcgcg tacaccggaa ttgccagccg gacgaccggc gtccttttcg tggactacac    1380
ccagctcaat ccgcctctgg agatttgggc gtgccccccg ccaaggccgg acggaccact    1440
gctagccgag tcagtgtgat ggggcgcctc tggccctccg gccctttggc ggggcgggtt    1500
tgccttccga ccgtggacgg gtcgccgaaa ggccgccgtg tgctcggtca ctccgccgcc    1560
tgaaataggc gctgggcttg gggagatctt ctcctcaacg cgtccgtctg gcaattcggg    1620
tgggcgcccc gggagcggga gtgacgcgca ggaaagagag agcgctctgc atgccgcccc    1680
tattccccag gcgagggcgc gacagagaag ggccgctgtg ttctgctgcg gccacgagca    1740
tactgcggcc tatgtagtcg tggcggggcg cccagatctc ccaggcattg agcgggttat    1800
ccacgaagct tatctcccgt cgtggccttg gccaacgccc ttccggtgta ctcatctggg    1860
tgacggcgat ctcgcgccac gccattataa gagcggcagg agggagacgc gccgagagca    1920
tgctgctgga accgctgagc gcgttaacag ccggagtttt ctgtgcctag gacgggctgt    1980
cgagaccgtg gtcctttgtc gtcgctacat acccgctcaa tgccttcgga gattggtggg    2040
cgtctgccgg cccgcgaagg cacgggcctc tccggaggta agccgctgtg gtgggattcg    2100
cgaaagggcc ttgtggtact ggcctgatag cgcgtttccg cgcttgcgcg agcgatctcg    2160
tctgcgaaca taaccaaaac ggggaggcgg cggcggaaca gagagagcag agtcctgcgc    2220
gccccccctct cacccggtcg cggcgcggcg atcgatgcac cacaggcgcc gctttcgcgg    2280
cccaacatct cactactgcg cgctagcgct ctgtgcggcg gctatactgt ccaagatgcg    2340
```

```
tcctaccggg caggccgccg cccggcacca gtcgcagcat cctggagccc gcgggtttca   2400
gtccacggca gcaggtggac gcccccgggc tcgtggccct cgcgactctc cgggtacgca   2460
cccggttccg gcaggatccc tccatcagcg cgggccgggc gccggccaca acagacgggg   2520
ccgcggcagg aagggccggg acccaagaag agagagatct gcggaaccgg tgagtacacg   2580
gaattgccag gacgaccggg tccttcgtgg ataaacgctc gcttcaatgc ctggagattt   2640
tgggcgtgcc ccgaactgct agccgagtag tgttgggctc gcgaagccct tgtgggtact   2700
ccgcctgata ggcgtgcctt gcgagatctc tctcaacaac aagcaagcgg aggaaggagg   2760
gaaaagaaag gagatcgctc cggcaaggca ccctaatcag gcagtaccac gagagggcct   2820
ttcgcgacca agcactactc gcgctagcag tctttgcggg ggcacgccaa atcctccgag   2880
aggcatctga gggcgggttt attccaacga aaggacccgg tcgtcgcctg gcaattcccc   2940
ggtgtagatc acgcgtttcg cgggcagaat tctctctcac aacgacagca acggagagag   3000
caaaagaaga gagatcgtgg cggaaccggt gagtacaccc ggaattggca ggaacgaccg   3060
gtcctttcgt ggataaaccc cgtccaatgc cgtcggagaa tttgggcgtg cccgcaagac   3120
tgcttaggcc gagtagtgtt ggtcgccgaa aggccttgtt tgtgactcgc ctgatagggt   3180
gcttgcgggg atgctctctc caaacaaggc acacggagga gggaggcaaa agagagagat   3240
cttcgcaagc ccgagcctat caagtggcgc agtacccaac aaggcttcgg cgagcccacc   3300
aacactactc gggctaggca gtccttgcgg ggcacgccca aatccggcag cattgaggcg   3360
ggtttttttc tttttaaaa tccagggtgc ggctaaagga cccggtcgtc ctggcaatcc   3420
gtgtgtacct cccggtccgc agatctgctc caaacagaca acaacgggag gcagaggaaa   3480
agagagagat ctgcggaacg tcgtgtgagt acgaaccgga attgcgcagg acgacctggt   3540
cccttcttcg tggatagaac ccgcctcaat gcactggaga tttggggcgt ggcccgccgc   3600
aaagactccg gcttagccga gtagatggtt gggtcgcgga tgcgcgaaag gccttgtggt   3660
acctcgcgtt ttttttttt atttgttctt ccaa                                  3694
```

<210> SEQ ID NO 16
<211> LENGTH: 3893
<212> TYPE: DNA
<213> ORGANISM: Artificial Sequence
<220> FEATURE:
<223> OTHER INFORMATION: Synthesized

<400> SEQUENCE: 16

```
cttgttgggt cgcgcaacag tgggcctgtg gtaactgagt tttgttcagg cctgcatagg     60
ttgtgctgcg agtctctctc gtgaagcaga gacagacggg aggcggagga aaagagacgc    120
cggatatgat ccgaagttgt tatctgcagc acctatcggc agtaccacag tgcctttcgc    180
gacccatagc actactcggc tagccagttc tgcgggggca cgccaaatct caggcattga    240
gcgggttatc cacgaagacg gaacccggcg tctggcaatc ggtgctactc cggttcgcag    300
catcttctca cacaaacaac gggggagaca ggaaagagag aaagatcaat gcgaaccggt    360
gagtcacacc aggattcgcc aggcgtaccg ggtccctttc gtggataaac ccagctcaat    420
gcctggagat tttggcgtgc caccgccaga cctgctcagc cgagtatgtt gggtcggaaa    480
ggccattgtg gtactagcct gataggggtg ctgtgcgaga tctctcttca acacacaacg    540
cagcgagaac ggttaaggta aacggagagt tctcggaagc accctatcgg gggcaagtcc    600
acaggaggcc cttttcgcga ccccatgaca ctactcgggg gggtcttcgc agtcttagcc    660
```

-continued

```
gggggccgcc caaatctctc aggcatttgg gcgggttttt tttatccacg aatgacctgg    720
cgggcggtcg tctggcaatg tcggtggtac tacaccgttt ctcgcagagt ctctctccaa    780
catccacaca agcggaggag gaggaaaaga gaagagatct ggcggagccc ggtggtactc    840
ggaattgcca ggacgaccgg ggtctttcgt gataaaccgc tcaatgcctg gaaatttggg    900
cgtgcccccg caagactgct agccgagtag tgttggcggt cgcgaatggc ttgtgtactg    960
gcctgaatag ggttgcttgc ggacgatctt cgtctcgaaa caacaacaaa cggaggaggg   1020
agggaaaaga gagagatcgt cgcagcaccc tatcagccgc agctaccaca agcctttcgc   1080
gacgggcaac gactactttg cggggagcag tcgttgcggg ccacgccaat ctcgcccagg   1140
catattcgag gcgggtttta tcccgcggag ggagcccggt cggtctggca attcggtgta   1200
ctcgcacggt ttcgcagatc tccttctcaa gcaacagggg ggggggaaca gagggggagg   1260
gaggcaggac caagaggagg atgatcctgc ggaaaccggt gagtacagcc gggacattgc   1320
ccaggacgac cgcgcagccg gccgcaccgc ccccccggtg cggtccttct cgtggccgca   1380
gacgccccgc ccaccggcgc ccgtcagtcc gcccgtgccg gagaagtatt gggatgggcg   1440
tgccgcccgc aagacgtgct cacgccgaag tagttgtgtt ggtggcgctg gagggtactt   1500
gtcggcgaaa ggcgctttcg ggtagctgcc tgataggccg tgcttggaga tctcctctca   1560
acaacaacaa cggaggccac ggaggcaaag agagctagat gctcgcagcg actatcccgg   1620
cgcaagggcc tcatgtatgg agccgaacac tcagctcggg ccgctaaggc ggctctggcg   1680
gggccgacgc ctcgcgcgcg ctcgaggctc gggtttatcc gcaccgacgg tacgccggtc   1740
gtcctggcat cggtgtcacc tcaccgttcc gcagatctct cgctgccgac caagcaagcc   1800
aaccggggag gccggggaaa agatgatcga gatcgtgcgg acgcctggtg acgtacaccg   1860
gattgccagg gactacgacc tccctttccc gggctcctct tcgtggtatc aagaccagca   1920
acgaaaccag agcgctcaca tggcctggac gggtttgcgc gtgtccggca agactgctag   1980
gcgcgagata ggtgttgggc gtgcgcgaag gaaaccttag tggtactaag aagcctgata   2040
gggcgtgcct tagcgagatc tctcgtgcac agagatttta cttcgcccac cacaaacaac   2100
cggaagaagg acggccaaca gagacgagat cctctcgcaa gcacccctat caggcagtat   2160
agcgcacaag gcctttcgcg acccagcact actcgggtcg ctcggcagag tctttggggc   2220
gcgccaaatg tgccaggcat tggacggcgt tatccccgaa agggacacca cggtcgtcct   2280
gcagaagcgt gccggtgtca ctgcaccggt tccgcgcagt ctctcttcgc tcaacaagca   2340
gacaacggaa gcggaggaaa agagagtaga tctggcaccg ggtgagtact acgcaatttt   2400
gcgccaggca gcacgggtcc cttcgtggat agaacccggc tcatgcctgg gactttgggc   2460
gtcggccccc gcaagactgc taggcccgag tagtgttggg tcgcgaaaat ggccttgtgg   2520
tactactcgc cttaggagta cgcttgtgag atcttctctc gcaacaaacc acgacggagg   2580
cgggaggaaa agagagagaa tcggtcgcaa agccccacta catcaggcag taccctacaa   2640
gggcctttcg cgactccaac actacttcgg ctctacgtca gtcttgcgcg ggggcagggc   2700
cgaatctcaa gacattgacg cggggtttct ccacggagga cgagatccgt tccttgtgca   2760
attccgtgta ctacagccgg tttcgcagat cctctcccaa caagcaacgc gaggcggcaa   2820
cggaacatga gagagatctg gcaccgtgag tgtacgcacg gaattgcagg cacgacgggt   2880
ctttcgtgga tagtcaaccc gctattgctg gagatttgtg cgttgcaccc agcaatgact   2940
gctagcggcc gacgtacgac ggggttagga aaaaggggtc gcgaaggcct ttgtggtaac   3000
taccggctga taggcgtgct tggcgagatc ctgctctcct ctcgcactaa caacagcggg   3060
```

```
gaggcctgga agaggagaat tcttcgccag ccgcccgatc cagacagcat agtactacac   3120
ccggtggctt cttcgcgccc acactactcg gctcgacgat cttgcggggc acgcccaaaa   3180
tcgtccgcag ggccttgagg cgggttatcc acgtaaaggc cacgaccggt cgtcctggcg   3240
acatatctcg gtgtactccg cgagttccgc tcgatctctt ctcgatatca ccaacgtgag   3300
gccaggcggc aaaaagagag agtctgcgaa cgcggctgac gatacaccgg attgcaggac   3360
gaccgggtct ttatccgtgg atagacaccc gccatgcctg gagatttggc gcgttgcccg   3420
caagactgct agcgagtagc tcgttgggcg tcggccgaac ggccttgtgg tactggctga   3480
taaggggtgc ttgcgacgat ctcttccttc acaacaacaa ccggaggagg aggaaaagag   3540
aggaaggatc tcgcagcacc cctacctcag gcaagtacca caaggctttc ggacccaacc   3600
tacctcgcta gcaggtcttg cgggggccac gccaaatctc cccaggcatt gagcaggcgt   3660
ttatccaacc gacaagcctc gcccgggcgg cgcccgcccg cccagcctgt ctcctcttct   3720
ctttctcttt cttctggcgc tcgcctcctc gtcggtcccc ggcgttccgg cccggcgtcc   3780
cctcatgtct cgccgcgcgc ccccctcctc ctttgcctgc ccgctctcgc cccctgtttc   3840
cttccacgct ggctcgcgcg tgcgctgtca ctcccgccct cccggtccgc aga          3893
```

<210> SEQ ID NO 17
<211> LENGTH: 1833
<212> TYPE: DNA
<213> ORGANISM: Artificial Sequence
<220> FEATURE:
<223> OTHER INFORMATION: Synthesized

<400> SEQUENCE: 17

```
cccgcagact gctagccgag tagtgttggg tcgcgaaggg ccttgtggta ctctccgcct     60
gatggggtgg cttgcgagaa cgccccccgcg ccaaaaaaac atgctctcct ccacaacaac    120
aacggaggag ggtgctgctt taggaaaaga gagagattcg cagcccccacg cagccctagt    180
cccgcagcag cgtacccacc caccccagcg cctgttcgcc gaccgccaca ctaccggctt    240
agcaagtctt gcggggcacg cccaaatctc ccgggcattg agcgcgtttt actccaccgg    300
aaagaccaga cctcgggcgt ctgggcattc ggttgctaac tgcaccggtt ttccccgcag    360
atcttttctc acacaaccac ggggcggagg aaaagagaga gatctggcgg tgaaccggct    420
tggtacaccc ggaattggcc cagggacgac cccgggtccc tttctcgtgg atagaacccg    480
cctccatgcc tggagatttg ggcgtccccc cgccagactg ctagccgagg tagctgtttg    540
ggctccgcga agggctttgt ggtactgctg aatagggtgc ttgcgagatc tccgtctcca    600
acaacaacaa caacggagga ggaggaaaca tgaagagaga tccttcgcaa gcacccctag    660
tccagcggca gtaccaacaa ggcctttcgg cgacccaaca cgttactcgg ctagcagtcc    720
ttgcgggggc acgcccaaat ctcccaggca tttgagccga cgcgcgtttt ttttatgccc    780
accgaaaggg gacccggccg tcctgtgcca aattcccggt gtactgccac ccggttccgc    840
agattcgtct ctccaacaac aacaacggag gaggaaggga aaagagagag atctgcggac    900
ccggtgaagc tcaccggaaa ttgccaaaag gagacccggg tcctttttttc gtttggataa    960
actccgctca tgcctggaga tttgggcgcg tgcccgcccc gcaagactgc ttaactagcc   1020
gagtagtgtt gggtcggcga aaggccttgg tggtaactgc ctgatagggt gggcgttggc   1080
gagatctcct ttcaacaaca acaacgggag ggaggaggaa aagagagaga tctcgcaagc   1140
aagccctatc aggcgtacca cacggccttt tcgcggaacc aaacacctac tccggctagc   1200
```

-continued

```
aagcttcctg cgggggggcca cggccaatct ccagccattt gagcgggttt ttatcacacg   1260

aagacccggc cggtctggca atctccggtg tagctgcaac gcggttccgc agatctcttg   1320

ctcaacaaca acaacggagg aggcaaagga aacagagaga gatctgcgga accggtgagt   1380

caccggaaat ttgcccagga cgacacgggt cctttcgtgg ataacaccgc caatgccgtg   1440

ggagatttgg gcgtgccccg caagaaactc tgcctagccg agtacgtgtt tgggtccggc   1500

gaaagggcct tgtggtaatt cgcctgatag ggtgcttggc ggagcatctc tctcaacaac   1560

ggaaaaacgg aggaggaggg aaagagagga gatcctcgca aagcacccta tcaggcagtg   1620

acaacaaggc ctttcgcgac ctaacactac ttcggcgtta gcatctttgc cgggggcagg   1680

cccaaatctc atacaggcat tggaggcgcg ggttttatcc acccgaaaag acccgccggt   1740

ctggcggggc aattccggtg gtacttcaac ggtttcccgc caagaatttc tcctcaaaca   1800

acaacaacgg ggaggaggaa aagagagaga tcc                                1833
```

<210> SEQ ID NO 18
<211> LENGTH: 3527
<212> TYPE: DNA
<213> ORGANISM: Artificial Sequence
<220> FEATURE:
<223> OTHER INFORMATION: Synthesized

<400> SEQUENCE: 18

```
cccgtctgag cccggcgttc ctatccacga ccccggaccc ccgcgcctcg tcccctgcgc     60

cgcaactgtc cggccctgct caaccctccg gttccggcca gatctcctct aacaacacca    120

acggaaggag gaggaaaaga gatgacgatc tgcggaaccg gttgagtaca ccggaattgc    180

caggacgacc gggtcctttc gtggataaac ccgctcatgc ccggagaatt tgggcggtgc    240

ccacgcaaga cctcgctccg attcagcgat agtcgttggg tcgcgaaagg cctttgtggt    300

actgcctgat aagggtgcct gcgagatctt ctcaaccagc acaagcggca gggaggcgag    360

gaaaagagag aagatctcgc acgcaccccc gcctatcagc gcagtaccac aaggcctttc    420

gcgaccaaca acctactcgg cccgcctagc agtcttgccg gggggcacgca aatctccagg    480

catgagcggg ttatccaccg acaggaccgt cgcgtcgtcc tggcaattcc ggtgtactgc    540

acaaggcttc cgcaggcatc tctctcaacc cacaccgcaa cgaggaggag gaaatacaga    600

gagagatctg cggaaccggt gagtacaccc ggattgcagg acaccgggtc ctttccgtgg    660

ataacccgtc gaatgccccg gagactttgg gcgtgccacg caagatgctc agcccgagta    720

gtgtctgggt cgcgaaaggc cttgtgtact gctgataggg tgcttgcgaa gatctctctc    780

aacaacaaca acggggagga ggaaagagat gagatctcgc aagcaacccc tatcagggca    840

ggtcaccaca agggcctcgt atcgcgaccc acactactcg gcctagcagt cttgcggggg    900

ggcacgccga aatctccagg catgtgagcg ggtttatccc gcgaaagggc cacgcggctc    960

gtgctggccg aattccggtg tacactcacc ggttccgcag atctcttctc catcagcaca   1020

acaacgagga ggaggaaaag agcaggaaga tctgcggaac cggtgaccgt acaccggatt   1080

gccaggacga ccagggtcct tctcgtggat atacccgctc aatgccctcg gagatttttg   1140

gccgtgccca cgcaagaatg ctagccgagt attgtttggg ttcgcgaaag gccttgtggt   1200

ctgcgcctga tagggtgctt gcgagtctct ctcaacaaca acaccggagg gaggacaaga   1260

gagagatctc gcaagcaccc tatgccaggg ccgtaccccc acggggcggg gcctggttcg   1320

cgagcccaaa cacctactcg gctaggcagg tcttgcgggg cacgcccaaa tctccaggca   1380

ttgagcgggt ttatcacgac aggacccgcg tcgtcctggc attccgtgtg tactccaacc   1440
```

-continued ggtttcccgc agatctatct caacaacaca acggaggaag gtaaggaaca gaggagagat 1500
ctgaggagaa acgccgcgtg gagtacacgg attgccagga cggaccgggt cctttcgtgg 1560
ataaacccgc tcaaatccgg agatttgggg cgtcggccca ccgcagactg ctagccgagt 1620
actgttgggt cgcgaaaggc cttgtgggta ctgcctatag ggtggctgcc gagatcttct 1680
ctcaacacac acggagggca gcgaggaaaa gagagacagc tctcggaacg ccoctattca 1740
ggggccaagg ccttcccgct cggcgacccc acactactcg gatagccagt cttgcggggc 1800
cacgcccaaa atctccagcc attcggagcg ggtttaatcc acgaaaggac cccggtcgtc 1860
ctgcaattcc ggtgtactca ccggttccgc agattctctc tcaacaacaa caaccgagag 1920
gagggacgga aaagagagac gatctgcgga accggtgagg ctacagcccg gaattgccag 1980
gacgaccggt ccttctcgtg atacaacccg cctcaatgcc gaagaatttg ggcgttgccc 2040
acgcaacgac tcgctagccc gacgtagtgt tgggtccgac gaaaggcttg tttgcgtact 2100
gctgtagggt gctttgcgag atcttcgctc tcacaacaac aacggaggca ggaagggaaa 2160
agagagagtc ctcgcaagca ccgcctagtc aggcagtacc acaaggcctt tccgcgaccg 2220
caacaactat cgggccgcta gcagtcttgc ggggcacgcc caattctcca ggcttgagcg 2280
ggttttatca ccgaaggacc cggtcgtcct ggcaattccg gttgtacgct caccggtccg 2340
cagatctcct ctcacacaca caacggagga ggaggaaaga cgagagatct gcggaaccgg 2400
ggtgagtaca cggacattgc caggacgccg ggttctttcg tggataaacc gctcaatgcc 2460
cggagatttg ggcgtgcccc acgcaatgac tgctagccag tagtgttggg ctcgcgaaag 2520
gcccttgtgg gtactgcgcc tgataagggt gcttgcgaga tcttctcaac aacacaacga 2580
gaggagggaa aagagagaga tctcgcaagc acctatcagg cgtacacaac ggccttcaat 2640
cagaaaaaag acccagacac tactcggcta gacagtcttg cgggggcacg ccccaaatct 2700
caggcattga acgggtttat ccacgaaagg accgcggtcg tcccctggca atctcggtgt 2760
actccagcgg tttccgcaca gatcctctcc tcccacacgc ccaacaacaa caacgcgagg 2820
aggaggcgaa aagacgagag attctgcgaa ccggtgagta caccggaatt gccaggccgg 2880
accgggtcct ttcgtggcta aaccccgctc aatgccgcgg agatttgggg cgttcgccac 2940
gcacgactcg ctagccgagt agtgttgggc tccgccccgg aaaggccttg gtggctactg 3000
cctgataggg tgctgcgaga tctctctcaa gcaacaacaa cggaggacgg gaggaaaaga 3060
cgacgacgca tctcgccacg cagccctaat caggggggcag tcaccgggca caaggcgctt 3120
tcgcgcaccc catcacactc aatgcgcgcc tggagcagtc cacccgcttg ccgggaggcc 3180
tcggcacggc caaacgcgcc agatctcgca cggcatccgt ggagccgcgg tttactccca 3240
cgaagaggat ccccggtcgt gcgctgggca attccggtgt acctcgcttg cagcccggct 3300
tccgcatgat ctcctctcca atcaacaaca acggaggagg gaggaaaaaa cgaggagcag 3360
atccgtggcg gacaacgccg gtgaggtaca acccgggaaa ttccgccgaa gcaaacggcg 3420
accggtctct tccccacgca acaccacgcg atcaatccaa acaaaaaaaa aaaaaaaaaa 3480
aaaaaacgtg gaaaccaaga ggaacaccac ccgccccccg ggcaccc 3527

<210> SEQ ID NO 19
<211> LENGTH: 5
<212> TYPE: DNA
<213> ORGANISM: Artificial Sequence
<220> FEATURE:
<223> OTHER INFORMATION: Synthesized

```
<400> SEQUENCE: 19

ctgcg                                                                  5


<210> SEQ ID NO 20
<211> LENGTH: 6
<212> TYPE: DNA
<213> ORGANISM: Artificial Sequence
<220> FEATURE:
<223> OTHER INFORMATION: Synthesized

<400> SEQUENCE: 20

ctggcg                                                                 6


<210> SEQ ID NO 21
<211> LENGTH: 6
<212> TYPE: DNA
<213> ORGANISM: Artificial Sequence
<220> FEATURE:
<223> OTHER INFORMATION: Synthesized

<400> SEQUENCE: 21

ctggca                                                                 6


<210> SEQ ID NO 22
<211> LENGTH: 4
<212> TYPE: DNA
<213> ORGANISM: Artificial Sequence
<220> FEATURE:
<223> OTHER INFORMATION: Synthesized

<400> SEQUENCE: 22

ctgc                                                                   4


<210> SEQ ID NO 23
<211> LENGTH: 6
<212> TYPE: DNA
<213> ORGANISM: Artificial Sequence
<220> FEATURE:
<223> OTHER INFORMATION: Synthesized

<400> SEQUENCE: 23

ctgcgg                                                                 6


<210> SEQ ID NO 24
<211> LENGTH: 7
<212> TYPE: DNA
<213> ORGANISM: Artificial Sequence
<220> FEATURE:
<223> OTHER INFORMATION: Synthesized

<400> SEQUENCE: 24

ctgcgga                                                                7


<210> SEQ ID NO 25
<211> LENGTH: 8
<212> TYPE: DNA
<213> ORGANISM: Artificial Sequence
<220> FEATURE:
<223> OTHER INFORMATION: Synthesized

<400> SEQUENCE: 25

ctgcggaa                                                               8


<210> SEQ ID NO 26
<211> LENGTH: 9
```

-continued

<212> TYPE: DNA
<213> ORGANISM: Artificial Sequence
<220> FEATURE:
<223> OTHER INFORMATION: Synthesized

<400> SEQUENCE: 26 ctgcggaac 9

<210> SEQ ID NO 27
<211> LENGTH: 10
<212> TYPE: DNA
<213> ORGANISM: Artificial Sequence
<220> FEATURE:
<223> OTHER INFORMATION: Synthesized

<400> SEQUENCE: 27
ctgcggaacc 10

<210> SEQ ID NO 28
<211> LENGTH: 11
<212> TYPE: DNA
<213> ORGANISM: Artificial Sequence
<220> FEATURE:
<223> OTHER INFORMATION: Synthesized

<400> SEQUENCE: 28
ctgcggaacc g 11

<210> SEQ ID NO 29
<211> LENGTH: 12
<212> TYPE: DNA
<213> ORGANISM: Artificial Sequence
<220> FEATURE:
<223> OTHER INFORMATION: Synthesized

<400> SEQUENCE: 29
ctgcggaacc gg 12

<210> SEQ ID NO 30
<211> LENGTH: 13
<212> TYPE: DNA
<213> ORGANISM: Artificial Sequence
<220> FEATURE:
<223> OTHER INFORMATION: Synthesized

<400> SEQUENCE: 30
ctgcggaacc ggt 13

<210> SEQ ID NO 31
<211> LENGTH: 14
<212> TYPE: DNA
<213> ORGANISM: Artificial Sequence
<220> FEATURE:
<223> OTHER INFORMATION: Synthesized

<400> SEQUENCE: 31
ctgcggaacc ggtg 14

<210> SEQ ID NO 32
<211> LENGTH: 15
<212> TYPE: DNA
<213> ORGANISM: Artificial Sequence
<220> FEATURE:
<223> OTHER INFORMATION: Synthesized

<400> SEQUENCE: 32
ctgcggaacc ggtga 15

<210> SEQ ID NO 33
<211> LENGTH: 16
<212> TYPE: DNA
<213> ORGANISM: Artificial Sequence
<220> FEATURE:
<223> OTHER INFORMATION: Synthesized

<400> SEQUENCE: 33
ctgcggaacc ggtgag 16

<210> SEQ ID NO 34
<211> LENGTH: 17
<212> TYPE: DNA
<213> ORGANISM: Artificial Sequence
<220> FEATURE:
<223> OTHER INFORMATION: Synthesized

<400> SEQUENCE: 34
ctgcggaacc ggtgagt 17

<210> SEQ ID NO 35
<211> LENGTH: 18
<212> TYPE: DNA
<213> ORGANISM: Artificial Sequence
<220> FEATURE:
<223> OTHER INFORMATION: Synthesized

<400> SEQUENCE: 35
ctgcggaacc ggtgagta 18

<210> SEQ ID NO 36
<211> LENGTH: 19
<212> TYPE: DNA
<213> ORGANISM: Artificial Sequence
<220> FEATURE:
<223> OTHER INFORMATION: Synthesized

<400> SEQUENCE: 36
ctgcggaacc ggtgagtac 19

<210> SEQ ID NO 37
<211> LENGTH: 20
<212> TYPE: DNA
<213> ORGANISM: Artificial Sequence
<220> FEATURE:
<223> OTHER INFORMATION: Synthesized

<400> SEQUENCE: 37
ctgcggaacc ggtgagtaca 20

<210> SEQ ID NO 38
<211> LENGTH: 21
<212> TYPE: DNA
<213> ORGANISM: Artificial Sequence
<220> FEATURE:
<223> OTHER INFORMATION: Synthesized

<400> SEQUENCE: 38
ctgcggaacc ggtgagtaca c 21

<210> SEQ ID NO 39
<211> LENGTH: 22
<212> TYPE: DNA
<213> ORGANISM: Artificial Sequence
<220> FEATURE:
<223> OTHER INFORMATION: Synthesized

<400> SEQUENCE: 39
ctgcggaacc ggtgagtaca cc 22

<210> SEQ ID NO 40
<211> LENGTH: 23
<212> TYPE: DNA
<213> ORGANISM: Artificial Sequence
<220> FEATURE:
<223> OTHER INFORMATION: Synthesized

<400> SEQUENCE: 40
ctgcggaacc ggtgagtaca ccg 23

<210> SEQ ID NO 41
<211> LENGTH: 24
<212> TYPE: DNA
<213> ORGANISM: Artificial Sequence
<220> FEATURE:
<223> OTHER INFORMATION: Synthesized

<400> SEQUENCE: 41
ctgcggaacc ggtgagtaca ccgg 24

<210> SEQ ID NO 42
<211> LENGTH: 25
<212> TYPE: DNA
<213> ORGANISM: Artificial Sequence
<220> FEATURE:
<223> OTHER INFORMATION: Synthesized

<400> SEQUENCE: 42
ctgcggaacc ggtgagtaca ccgga 25

<210> SEQ ID NO 43
<211> LENGTH: 26
<212> TYPE: DNA
<213> ORGANISM: Artificial Sequence
<220> FEATURE:
<223> OTHER INFORMATION: Synthesized

<400> SEQUENCE: 43
ctgcggaacc ggtgagtaca ccggaa 26

<210> SEQ ID NO 44
<211> LENGTH: 27
<212> TYPE: DNA
<213> ORGANISM: Artificial Sequence
<220> FEATURE:
<223> OTHER INFORMATION: Synthesized

<400> SEQUENCE: 44
ctgcggaacc ggtgagtaca ccggaat 27

<210> SEQ ID NO 45
<211> LENGTH: 28
<212> TYPE: DNA
<213> ORGANISM: Artificial Sequence
<220> FEATURE:
<223> OTHER INFORMATION: Synthesized

<400> SEQUENCE: 45
ctgcggaacc ggtgagtaca ccggaatt 28

<210> SEQ ID NO 46
<211> LENGTH: 29
<212> TYPE: DNA
<213> ORGANISM: Artificial Sequence
<220> FEATURE:
<223> OTHER INFORMATION: Synthesized

<400> SEQUENCE: 46
ctgcggaacc ggtgagtaca ccggaattg 29

<210> SEQ ID NO 47
<211> LENGTH: 30
<212> TYPE: DNA
<213> ORGANISM: Artificial Sequence
<220> FEATURE:
<223> OTHER INFORMATION: Synthesized

<400> SEQUENCE: 47
ctgcggaacc ggtgagtaca ccggaattgc 30

<210> SEQ ID NO 48
<211> LENGTH: 4
<212> TYPE: DNA
<213> ORGANISM: Artificial Sequence
<220> FEATURE:
<223> OTHER INFORMATION: Synthesized

<400> SEQUENCE: 48 ctcg 4

<210> SEQ ID NO 49
<211> LENGTH: 5
<212> TYPE: DNA
<213> ORGANISM: Artificial Sequence
<220> FEATURE:
<223> OTHER INFORMATION: Synthesized

<400> SEQUENCE: 49 ctcgc 5

<210> SEQ ID NO 50
<211> LENGTH: 6
<212> TYPE: DNA
<213> ORGANISM: Artificial Sequence
<220> FEATURE:
<223> OTHER INFORMATION: Synthesized

<400> SEQUENCE: 50 ctcgca 6

<210> SEQ ID NO 51
<211> LENGTH: 7
<212> TYPE: DNA
<213> ORGANISM: Artificial Sequence
<220> FEATURE:
<223> OTHER INFORMATION: Synthesized

<400> SEQUENCE: 51 ctcgcaa 7

<210> SEQ ID NO 52
<211> LENGTH: 8
<212> TYPE: DNA
<213> ORGANISM: Artificial Sequence
<220> FEATURE:
<223> OTHER INFORMATION: Synthesized

<400> SEQUENCE: 52 ctcgcaag 8

<210> SEQ ID NO 53
<211> LENGTH: 9
<212> TYPE: DNA
<213> ORGANISM: Artificial Sequence
<220> FEATURE:
<223> OTHER INFORMATION: Synthesized

<400> SEQUENCE: 53 ctcgcaagc 9

<210> SEQ ID NO 54
<211> LENGTH: 10
<212> TYPE: DNA
<213> ORGANISM: Artificial Sequence
<220> FEATURE:
<223> OTHER INFORMATION: Synthesized

<400> SEQUENCE: 54
ctcgcaagca 10

<210> SEQ ID NO 55
<211> LENGTH: 11
<212> TYPE: DNA
<213> ORGANISM: Artificial Sequence
<220> FEATURE:
<223> OTHER INFORMATION: Synthesized

<400> SEQUENCE: 55
ctcgcaagca c 11

<210> SEQ ID NO 56
<211> LENGTH: 12
<212> TYPE: DNA
<213> ORGANISM: Artificial Sequence
<220> FEATURE:
<223> OTHER INFORMATION: Synthesized

<400> SEQUENCE: 56
ctcgcaagca cc 12

<210> SEQ ID NO 57
<211> LENGTH: 13
<212> TYPE: DNA
<213> ORGANISM: Artificial Sequence
<220> FEATURE:
<223> OTHER INFORMATION: Synthesized

<400> SEQUENCE: 57
ctcgcaagca ccc 13

<210> SEQ ID NO 58
<211> LENGTH: 14
<212> TYPE: DNA
<213> ORGANISM: Artificial Sequence
<220> FEATURE:
<223> OTHER INFORMATION: Synthesized

<400> SEQUENCE: 58
ctcgcaagca ccct 14

<210> SEQ ID NO 59

<211> LENGTH: 15
<212> TYPE: DNA
<213> ORGANISM: Artificial Sequence
<220> FEATURE:
<223> OTHER INFORMATION: Synthesized

<400> SEQUENCE: 59
ctcgcaagca cccta 15

<210> SEQ ID NO 60
<211> LENGTH: 16
<212> TYPE: DNA
<213> ORGANISM: Artificial Sequence
<220> FEATURE:
<223> OTHER INFORMATION: Synthesized

<400> SEQUENCE: 60
ctcgcaagca ccctat 16

<210> SEQ ID NO 61
<211> LENGTH: 17
<212> TYPE: DNA
<213> ORGANISM: Artificial Sequence
<220> FEATURE:
<223> OTHER INFORMATION: Synthesized

<400> SEQUENCE: 61
ctcgcaagca ccctatc 17

<210> SEQ ID NO 62
<211> LENGTH: 18
<212> TYPE: DNA
<213> ORGANISM: Artificial Sequence
<220> FEATURE:
<223> OTHER INFORMATION: Synthesized

<400> SEQUENCE: 62
ctcgcaagca ccctatca 18

<210> SEQ ID NO 63
<211> LENGTH: 19
<212> TYPE: DNA
<213> ORGANISM: Artificial Sequence
<220> FEATURE:
<223> OTHER INFORMATION: Synthesized

<400> SEQUENCE: 63
ctcgcaagca ccctatcag 19

<210> SEQ ID NO 64
<211> LENGTH: 20
<212> TYPE: DNA
<213> ORGANISM: Artificial Sequence
<220> FEATURE:
<223> OTHER INFORMATION: Synthesized

<400> SEQUENCE: 64
ctcgcaagca ccctatcagg 20

<210> SEQ ID NO 65
<211> LENGTH: 21
<212> TYPE: DNA
<213> ORGANISM: Artificial Sequence
<220> FEATURE:
<223> OTHER INFORMATION: Synthesized

<400> SEQUENCE: 65
ctcgcaagca ccctatcagg c 21

<210> SEQ ID NO 66
<211> LENGTH: 22
<212> TYPE: DNA
<213> ORGANISM: Artificial Sequence
<220> FEATURE:
<223> OTHER INFORMATION: Synthesized

<400> SEQUENCE: 66
ctcgcaagca ccctatcagg ca 22

<210> SEQ ID NO 67
<211> LENGTH: 23
<212> TYPE: DNA
<213> ORGANISM: Artificial Sequence
<220> FEATURE:
<223> OTHER INFORMATION: Synthesized

<400> SEQUENCE: 67
ctcgcaagca ccctatcagg cag 23

<210> SEQ ID NO 68
<211> LENGTH: 24
<212> TYPE: DNA
<213> ORGANISM: Artificial Sequence
<220> FEATURE:
<223> OTHER INFORMATION: Synthesized

<400> SEQUENCE: 68
ctcgcaagca ccctatcagg cagt 24

<210> SEQ ID NO 69
<211> LENGTH: 25
<212> TYPE: DNA
<213> ORGANISM: Artificial Sequence
<220> FEATURE:
<223> OTHER INFORMATION: Synthesized

<400> SEQUENCE: 69
ctcgcaagca ccctatcagg cagta 25

<210> SEQ ID NO 70
<211> LENGTH: 26
<212> TYPE: DNA
<213> ORGANISM: Artificial Sequence
<220> FEATURE:
<223> OTHER INFORMATION: Synthesized

<400> SEQUENCE: 70
ctcgcaagca ccctatcagg cagtac 26

<210> SEQ ID NO 71
<211> LENGTH: 27
<212> TYPE: DNA
<213> ORGANISM: Artificial Sequence
<220> FEATURE:
<223> OTHER INFORMATION: Synthesized

<400> SEQUENCE: 71
ctcgcaagca ccctatcagg cagtacc 27

<210> SEQ ID NO 72
<211> LENGTH: 28
<212> TYPE: DNA

-continued

```
<213> ORGANISM: Artificial Sequence
<220> FEATURE:
<223> OTHER INFORMATION: Synthesized

<400> SEQUENCE: 72

ctcgcaagca ccctatcagg cagtacca                                    28


<210> SEQ ID NO 73
<211> LENGTH: 29
<212> TYPE: DNA
<213> ORGANISM: Artificial Sequence
<220> FEATURE:
<223> OTHER INFORMATION: Synthesized

<400> SEQUENCE: 73

ctcgcaagca ccctatcagg cagtaccac                                   29


<210> SEQ ID NO 74
<211> LENGTH: 30
<212> TYPE: DNA
<213> ORGANISM: Artificial Sequence
<220> FEATURE:
<223> OTHER INFORMATION: Synthesized

<400> SEQUENCE: 74

ctcgcaagca ccctatcagg cagtaccaca                                  30
```

ALGORITHMS FOR SEQUENCE DETERMINATIONS

CROSS-REFERENCE TO RELATED APPLICATIONS

The present application is a continuation of U.S. application Ser. No. 14/346,954 filed Mar. 24, 2014, which is a US National Stage application of PCT/US2012/057237 filed Sep. 26, 2012, which claims the benefit of 61/539,440 filed Sep. 26, 2011, each of which is incorporated by reference in its entirety for all purposes.

REFERENCE TO A SEQUENCE LISTING

This application includes an electronic sequence listing in a file named 443115CON_SEQLST.txt, created on Oct. 30, 2018 and containing 34,532 bytes, which is hereby incorporated by reference in its entirety for all purposes.

BACKGROUND

Over the past decade, DNA sequencing throughput has increased over 50-fold. Advances in DNA sequencing have revolutionized the fields of cellular and molecular biology. High-throughput sequencing platforms include the 454 FLX™ or 454 TITANIUM™ (Roche), the SOLEXA™ Genome Analyzer (Illumina), the HELISCOPE™ Single Molecule Sequencer (Helicos Biosciences), the SOIID™ DNA Sequencer (Life Technologies/Applied Biosystems) instruments), SMRT™ technology developed by Pacific Biosystems, as well as other platforms still under development by companies such as Intelligent Biosystems.

Although such sequencing platforms generate vast amounts of sequencing data including multiple reads of the same target sequence, difficulties remain in deducing correct sequences present in a sample due to errors introduced by the high-throughput sequencing methods. With the high error rate, it is difficult to identify the majority species consistently and reliably. It is even more difficult to identify the minority species that differ little from the majority species and to determine their prevalence. Most sequence alignment-based methods alone cannot overcome high frequencies of error.

SUMMARY OF THE CLAIMED INVENTION

The invention provides computer-implemented methods of developing a consensus sequence from a plurality of sequencing reads of a nucleic acid target. Such methods involve (a) receiving a population of raw target sequencing reads of a nucleic acid target comprising an anchor segment and an adjacent segment; the anchor segment being of known sequence and the adjacent segment being of unknown sequence; and at least some of the raw target sequencing reads containing sequencing errors; (b) evaluating the accuracy of sequencing of the anchor segment in different raw target sequencing reads by comparing raw target sequencing reads of the anchor segment with the known sequence of the anchor segment; (c) assigning a subset of the raw target sequencing reads into an accepted class based on reaching at least a threshold level of accuracy of the sequencing of the anchor segment; (d) polling nucleobases at a position equidistant to the anchor segment sequence in raw target sequencing reads in the accepted class to determine a consensus nucleobase, which consensus nucleobase is assigned as the first nucleobase of a nascent sequence of the adjacent segment; (e) assigning raw target sequencing reads having the consensus nucleobase determined in the prior polling step to remain in an accepted class and assigning raw target sequencing reads lacking the consensus nucleobase determined in the prior polling step to the rejected class; (f) optionally reassigning a raw target sequencing read from the rejected class to the accepted class by scoring similarity of the raw target sequencing read to the nascent sequence and reintroducing the raw target sequencing read if the sequence similarity reaches at least a threshold level of similarity; and (g) repeating steps (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment.

In some methods, step (f) is performed at least once. In some methods, step (g) is performed at least 20 times and step (f) at least 5 times. In some methods, step (g) is performed at least 100 times and step (f) at least 20 times. In some methods, the threshold for step (f) is at least 80% identity between the raw target sequencing read and nascent sequence when maximally aligned and a match between the last assigned nucleobase of the nascent sequence and corresponding nucleobase of the raw targeting sequencing read. In some methods, the threshold level of accuracy of the sequencing the anchor segment is based on percentage of sequence identity and/or location of matched nucleobases between a raw target sequencing read and the known anchor segment. In some methods the threshold level of accuracy requires a raw target sequencing read to have the correct nucleobase corresponding to the nucleobase of the anchor segment immediately adjacent the adjacent segment. In some methods, the nucleic acid target includes a nucleobase variation at a position and when step (g) polls the position it determines two consensus nucleobases for the position, wherein the nascent sequence is branched into two nascent sequences differing between the two consensus nucleobases and the consensus nucleobase determined in further repetitions of step (g) is assigned to both nascent sequences. In some methods, the nucleic acid target comprises first and second anchor segments at opposing ends of the nucleic acid target and the raw target sequencing reads include a first group of raw target sequencing reads of the first anchor segment and an adjacent segment and a second group of raw target sequencing reads of the second anchor segment and an adjacent segment; the first and second groups being raw sequencing reads of opposing strands of the nucleic acid target and the method is performed on the first and second groups of raw target sequencing reads to determine consensus sequences of opposing strands of the target nucleic acid.

In some methods, the raw sequencing reads comprise raw sequencing reads of first and second nucleic acid targets, the first nucleic acid target comprising the anchor segment linked to a first adjacent segment and the second nucleic acid target comprising the anchor segment linked to a second adjacent segment. In some methods, the first and second adjacent segments are overlapping segments. In some methods, the first and second adjacent segments are fragments of the same contiguous polynucleotide. In some methods, the first and second adjacent segments are nonoverlapping segments. In some methods, the raw sequencing reads comprising raw sequence reads of a plurality of nucleic acid targets, the different nucleic acid targets comprising the anchor segment linked to different adjacent segments; the different adjacent segments including overlapping and non-overlapping segments. In some methods, a strand of the anchor segment is a primer or primer binding site incorporated into the nucleic acid target. In some methods, a strand of the anchor segment has 4-120 nucleobases, or 8-30 nucleobases. In some methods, the anchor segment is an oligonucleotide ligated to a nucleic acid fragment to be sequenced. In some methods, the anchor segment and adjacent segment are contiguous segments in a nucleic acid from nature. In some methods, the anchor segment is a repeat sequence.

Some methods also involve outputting the sequence of at least part of the adjacent segment. Some methods also involve synthesizing a nucleic acid sequence having a sequence comprising at least part of the adjacent segment. Some methods also include experimentally determining the population of raw target sequencing reads of the target nucleic acid.

In some methods, the population of raw target sequencing reads is determined by a sequencing-by-synthesis method. In some methods, the sequencing method is single-molecule sequencing. In some methods, the sequencing method is single-molecule real time sequencing. In some methods, the nucleic acid target is in the form of a circular template. In some methods, the nucleic acid target is a homogeneous population of the same nucleic acid molecule.

In some methods the nucleic acid target is a heterogeneous population of variant nucleic acid molecules. In some methods, the variant nucleic acid molecules are variant nucleic acid molecules of the same virus. In some method, the virus is HIV or HCV. In some methods, the variants are allelic variants. In some methods, the nucleic acid target is a circular DNA molecule and the raw target sequencing reads comprise alternating reads of the anchor segment and the adjacent segment. In some methods, the reads of the adjacent segment comprise reads of alternating strands of the adjacent segment. In some methods, the circular DNA molecule is formed by ligating first and second hairpin anchor segments to the adjacent segment. In some methods, the first and second hairpin anchor segments are the same. In some methods, the first and second hairpin anchors are different and the raw target sequencing reads comprise alternating reads of the first and second hairpin anchor segments.

Some methods also involve designating a segment of the nascent sequence of the adjacent segment as a new anchor segment and repeating the method to determine a consensus sequence of an adjacent segment adjacent the new anchor segment.

The invention further provides a computer program product for analyzing a nucleic acid target, comprising (a) code for receiving a population of raw target sequencing reads of a nucleic acid target comprising an anchor segment and an adjacent segment; the anchor segment being of known sequence and the adjacent segment being of unknown sequence; and at least some of the raw target sequencing reads containing sequencing errors; (b) code for evaluating the accuracy of sequencing of the anchor segment in different raw target sequencing reads by comparing the raw target sequencing reads of the anchor segment with the known sequence of the anchor segment; (c) code for assigning a subset of the raw target sequencing reads into an accepted class based on reaching at least a threshold level of accuracy of the sequencing of the anchor segment; (d) code for polling nucleobases at a position equidistant to the anchor segment sequence in raw target sequencing reads in the accepted class to determine a consensus nucleobase, which consensus nucleobase is assigned as the first nucleobase of a nascent sequence of the adjacent segment; (e) code for assigning raw target sequencing reads having the consensus nucleobase determined in the prior polling step to remain in an accepted class and assigning raw target sequencing reads lacking the consensus nucleobase determined in the prior polling step to the rejected class; (f) code for optionally reassigning a raw target sequencing read from the rejected class to the accepted class by scoring similarity of the raw target sequencing read to the nascent sequence and reintroducing the raw target sequencing read if the sequence similarity reaches at least a threshold level of similarity; and (g) code for repeating steps coded in (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment.

In some computer program products, the threshold in (f) is at least 80% identity between the raw target sequencing read and nascent sequence when maximally aligned and a match between the last assigned nucleobase of the nascent sequence and corresponding nucleobase of the raw targeting sequencing read. In some computer program products, the threshold level of accuracy of the sequencing the anchor segment is based on percentage of sequence identity and/or location of matched nucleobases between a raw target sequencing read and the known anchor segment. In some computer program products, the threshold level of accuracy requires a raw target sequencing read to have the correct nucleobase corresponding to the nucleobase of the anchor segment immediately adjacent the adjacent segment. In some computer program products, the raw sequencing reads comprise raw sequencing reads of first and second nucleic acid targets, the first nucleic acid target comprising the anchor segment linked to a first adjacent segment and the second nucleic acid target comprising the anchor segment linked to a second adjacent segment. In some computer program products, the first and second adjacent segments are overlapping segments. In some computer program products, the first and second adjacent segments are fragments of the same contiguous polynucleotide. In some computer program products, the first and second adjacent segments are non-overlapping segments. In some computer program products, the raw sequencing reads comprise raw sequencing reads of a plurality of nucleic acid targets, the different nucleic acid targets comprising the anchor segment linked to different adjacent segments; the different adjacent segments including overlapping and nonoverlapping segments. In some computer program products, the strand of the anchor segment is a primer incorporated into the nucleic acid target. In some computer program products, the strand of the anchor segment has 4-120 nucleobases, or 8-30 nucleobases. In some computer program products, the anchor segment is an oligonucleotide ligated to a nucleic acid fragment to be sequenced. In some computer program products, the anchor segment and adjacent segment are contiguous segments in a nucleic acid from nature. In some computer program products, the anchor segment is a repeat sequence. Some computer program products further comprise code for outputting the sequence of at least part of the adjacent segment. In some computer program products, the nucleic acid target is a homogeneous population of the same nucleic acid molecule. In some computer program products, the nucleic acid target is a heterogeneous population of variant nucleic acid molecules. In some computer program products, the variant nucleic acid molecules are variant nucleic acid molecules of the same virus. In some computer program products, the virus is HIV or HCV. In some computer program products, the variants are allelic variants.

The invention further provides a system for analyzing a nucleic acid target, comprising: (1) a system bus; (2) a memory coupled to the system bus; and (3) a processor coupled to the system bus operatively disposed to: (a) receive a population of raw target sequencing reads of a nucleic acid target comprising an anchor segment and an adjacent segment; the anchor segment being of known sequence and the adjacent segment being of unknown sequence; and at least some of the raw target sequencing reads containing sequencing errors; (b) evaluate the accuracy of sequencing of the anchor segment in different raw target sequencing reads by comparing raw target sequencing reads of the anchor segment with the known sequence of the anchor segment; (c) assign a subset of the raw target sequencing reads into an accepted class based on reaching at least a threshold level of accuracy of the sequencing of the anchor segment; (d) poll nucleobases at a position equidistant to the anchor segment sequence in raw target sequencing reads in the accepted class to determine a consensus nucleobase, which consensus nucleobase is assigned as the first nucleobase of a nascent sequence of the adjacent segment; (e) assign raw target sequencing reads having the consensus nucleobase determined in the prior polling step to remain in an accepted class and assigning raw target sequencing reads lacking the consensus nucleobase determined in the prior polling step to the rejected class; (f) optionally reassign a raw target sequencing read from the rejected class to the accepted class by scoring similarity of the raw target sequencing read to the nascent sequence and reintroducing the raw target sequencing read if the sequence similarity reaches at least a threshold level of similarity; and (g) repeat steps (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment.

In some systems, the threshold in (f) is at least 80% identity between the raw target sequencing read and nascent sequence when maximally aligned and a match between the last assigned nucleobase of the nascent sequence and corresponding nucleobase of the raw targeting sequencing read. In some systems, the threshold level of accuracy of sequencing the anchor segment is based on percentage of sequence identity and/or location of matched nucleobases between a raw target sequencing read and the known anchor segment. In some systems, the threshold level of accuracy requires a raw target sequencing read to have the correct nucleobase corresponding to the nucleobase of the anchor segment immediately adjacent the adjacent segment. In some systems, the raw sequencing reads comprise raw sequencing reads of first and second nucleic acid targets, the first nucleic acid target comprising the anchor segment linked to a first adjacent segment and the second nucleic acid target comprising the anchor segment linked to a second adjacent segment. In some systems, the first and second adjacent segments are overlapping segments. In some systems, the first and second adjacent segments are fragments of the same contiguous polynucleotide. In some systems, the first and second adjacent segments are nonoverlapping segments. In some systems, the raw sequencing reads comprising raw sequence reads of a plurality of nucleic acid targets, the different nucleic acid targets comprising the anchor segment linked to different adjacent segments; the different adjacent segments including overlapping and nonoverlapping segments. In some systems, the strand of the anchor segment is a primer incorporated into the nucleic acid target. In some systems, the strand of the anchor segment has 4-120 nucleobases. In some systems, the strand of the anchor segment has 8-30 nucleobases. In some systems, the anchor segment is an oligonucleotide ligated to a nucleic acid fragment to be sequenced. In some systems, the anchor segment and adjacent segment are contiguous segments in a nucleic acid from nature. In some systems, the anchor segment is a repeat sequence. In some systems, the processer is operatively disposed to outputting the sequence of at least part of the adjacent segment. In some systems, the nucleic acid target is a homogeneous population of the same nucleic acid molecule. In some systems, the nucleic acid target is a heterogeneous population of variant nucleic acid molecules. In some systems, the variant nucleic acid molecules are variant nucleic acid molecules of the same virus. In some systems, the virus is HIV or HCV. In some systems, the variants are allelic variants.

The invention further provides methods of differentially treating a patient population. Such methods involve sequencing samples from members of the patient population; wherein for each sample the sequencing comprises: (a) receiving a population of raw target sequencing reads of a nucleic acid target comprising an anchor segment and an adjacent segment; the anchor segment being of known sequence and the adjacent segment being of unknown sequence; and at least some of the raw target sequencing reads containing sequencing errors; (b) evaluating the accuracy of sequencing of the anchor segment in different raw target sequencing reads by comparing raw target sequencing read of the anchor segment with the known sequence of the anchor segment; (c) assigning a subset of the raw target sequencing reads into an accepted class based on reaching at least a threshold level of accuracy of the sequencing of the anchor segment; (d) polling nucleobases at a position adjacent the anchor segment sequence in raw target sequencing reads in the accepted class to determine a consensus nucleobase, which consensus nucleobase is assigned as the first nucleobase of a nascent sequence of the adjacent segment; (e) assigning raw target sequencing reads having the consensus nucleobase determined in the prior polling step to remain in an accepted class and assigning raw target sequencing reads lacking the consensus nucleobase determined in the prior polling step to the rejected class; (f)

optionally reassigning a raw target sequencing read from the rejected class to the accepted class by scoring similarity of the raw target sequencing read to the nascent sequence and reintroducing the raw target sequencing read if the sequence similarity reaches at least a threshold level of similarity; and (g) repeating steps (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment. Different members of the patient population receive different treatment regimes depending on the determined sequence for the sample from each member.

The invention further provides computer-implemented methods of analyzing a nucleic acid target. Such methods involve (a) receiving a population of raw target sequencing reads of a nucleic acid target comprising an anchor segment and an adjacent segment; the anchor segment being of known sequence and the adjacent segment being of unknown sequence; and at least some of the raw target sequencing reads containing sequencing errors; (b) evaluating the accuracy of sequencing of the anchor segment in different raw target sequencing reads by comparing raw target sequencing reads of the anchor segment with the known sequence of the anchor segment; (c) assigning a subset of the raw target sequencing reads into an accepted class based on the accuracy of sequencing of the anchor segment in the raw target sequencing reads; and (d) determining a sequence of the anchor segment from raw target sequencing reads in the accepted class.

In some methods, step (d) comprises polling nucleobases at corresponding positions in raw target sequencing reads in the accepted class to determine a consensus nucleobase, which consensus nucleobase is assigned as the first nucleobase of a nascent sequence of the adjacent segment and wherein step (d) is repeated and the consensus nucleobases determined in successive repetitions are assigned as successive nucleobases in the nascent sequence of the adjacent segment. Some methods also involve assigning raw target sequencing reads having the consensus nucleobase determined in the prior polling step to remain in an accepted class and assigning raw target sequencing reads lacking the consensus nucleobase determined in the prior polling step to a rejected class. Some methods also involve designating a segment of the sequence of the adjacent segment as a new anchor segment and repeating the method to determine a sequence of an adjacent segment adjacent the new anchor segment.

The invention further provides a computer program product for analyzing a nucleic acid target, comprising code for receiving a population of raw target sequencing reads of a nucleic acid target comprising an adapter segment and an adjacent segment; the adapter segment being of known correct sequence and the adjacent segment being of unknown sequence; and at least some of the raw target sequences containing sequencing errors; code for evaluating the accuracy of sequencing of the adapter segment in different raw target sequences by comparing raw target sequencing reads of the anchor segment with the known correct sequence of the adapter segment; code for assigning a subset of the raw target sequences into an accepted class based on the accuracy of sequencing of the adapter segment in the raw target sequences; code for aligning at least some of the raw target sequences from the accepted class; and code for determining a sequence of at least part of the adjacent segment from the aligned sequences.

The invention further provides a system for analyzing a nucleic acid target, comprising: (a) a system bus; (b) a memory coupled to the system bus; and (c) a processor coupled to the system bus for receiving a population of raw target sequencing reads of a nucleic acid target comprising an adapter segment and an adjacent segment; the adapter segment being of known correct sequence and the adjacent segment being of unknown sequence; and at least some of the raw target sequences containing sequencing errors; evaluating the accuracy of sequencing of the adapter segment in different raw target sequences by comparing the raw target sequencing reads of the anchor segment with the known correct sequence of the adapter segment; assigning a subset of the raw target sequences into an accepted class based on the accuracy of sequencing of the adapter segment in the raw target sequences; aligning at least some of the raw target sequences from the accepted class; and determining a sequence of at least part of the adjacent segment from the aligned sequences.

The invention further provides methods of differentially treating a patient population. Such methods involve sequencing samples from members of the patient population; wherein for each sample the sequencing comprises receiving a population of raw target sequencing reads of a nucleic acid target comprising an adapter segment and an adjacent segment; the adapter segment being of known correct sequence and the adjacent segment being of unknown sequence; and at least some of the raw target sequences containing sequencing errors; evaluating the accuracy of sequencing of the adapter segment in different raw target sequences by comparing raw target sequencing reads of the anchor segment with the known correct sequence of the adapter segment; assigning a subset of the raw target sequences into an accepted class based on the accuracy of sequencing of the adapter segment in the raw target sequences; aligning at least some of the raw target sequences from the accepted class; and determining a sequence of at least part of the adjacent segment from the aligned sequences; wherein different members of the patient population receive different treatment regimes depending on the determined sequence for the sample from each member.

Definitions

Brief descriptions of some of the terms used in this application appear below. Some of these terms are further described in the rest of the specification.

A nucleobase is the base component of a nucleotide including any of the natural bases adenine (A), cytosine (C), guanine (G) and thymine (T) (for DNA) and A, C, G, and uracil (U) (for RNA) or analogs thereof subjectable to a sequencing reaction (e.g., support template-dependent incorporation of a complementary nucleobase). Nucleobases are sometimes referred to simply as bases.

A nucleobase attached to a sugar, can be referred to as a nucleobase unit, or monomer. Sugar moieties of a nucleic acid can be ribose, deoxyribose, dideoxyribose or similar compounds, e.g., with 2' methoxy or 2' halide substitutions. Nucleotides and nucleosides are examples of nucleobase units.

A nucleic acid target is the nucleic acid unit that is the subject of a sequencing reaction and gives rise to a sequencing read. A nucleic acid target comprises an anchor segment of known sequence and an adjacent sequence whose sequence is to be determined.

A raw target sequencing read is a contiguous sequence of nucleobases assigned during a sequencing reaction on a nucleic acid target. A raw target sequencing read may contain sequencing error(s). Thus raw target sequencing reads of the same nucleic acid target can differ from one another by virtue of sequencing errors.

Raw target sequencing reads can be assigned into an accepted class or rejected class. Raw target sequencing reads in the accepted class have passed a quality control measure. The quality control measure can be that the accuracy of sequencing of the anchor segment at least reaches a defined threshold, or that a raw target sequencing read contains a consensus nucleotide at an immediately previously polled position or a raw target sequencing read exceeds a threshold level of sequence similarity with the nascent sequence. Conversely raw target sequencing reads in the rejected class have failed a quality control measure. Typically, this quality control measure is failure to contain a consensus nucleobase at a polled position. Raw target sequencing can be assigned from the accepted class to the rejected class and vice versa as described below.

Polling compares the nucleobase occupying corresponding positions among raw target sequencing reads to determine a consensus nucleobase for that position.

A nascent sequence refers to a string of contiguous nucleobases identified by repeated polling cycles. The nascent sequence is the sequence of at least part of the adjacent segment of a nucleic acid target.

A threshold relates to one or more criteria for evaluating a nucleotide sequence, such as a raw target sequencing read. Such a threshold can be stored as code or provided by user input, or selected from a menu of possible thresholds when the method is performed.

In pairwise comparisons between two nucleic acid sequences, the nucleic acids are maximally aligned when the number of nucleobase matches is greatest. Percentage sequence identity can be defined as the number of matched nucleobases between aligned sequences divided by the number of nucleobases in one of the sequences (usually the known sequence if one sequence is known and the other is not). Extra nucleobases in an unknown sequence flanking the part of the unknown aligned with a known sequence are not scored.

Some or all of a raw target sequence read corresponds with the nucleic acid target (i.e., has the same sequence as a strand of the nucleic acid target other than sequence errors). The portion of a raw target sequencing read corresponding to an anchor segment of a nucleic acid target is the portion of the raw target sequencing aligned with the known sequence of the anchor segment when the raw target sequencing read is maximally aligned with the anchor segment. A portion of the raw targeting sequencing read adjacent to the segment corresponding to the anchor segment corresponds with the adjacent segment of the nucleic acid target.

A corresponding position in two or more nucleic acid sequences is a position aligned between the sequences when the sequences are maximally aligned over their entire length or at least a defined window thereof including the corresponding position (e.g., at least 10 or 20 nucleotides).

A "primer" is an oligonucleotide, typically between about 10 to 100 nucleotides in length, capable of selectively binding to a specified nucleic acid or "template" by hybridizing with the template. The primer provides a point of initiation for polymerase-mediated template-directed synthesis of a nucleic acid complementary to the template. Primers hybridizing to opposing strands of a double-stranded sequence are referred to as forward and reverse primers. An oligonucleotide primer used to initiate a sequencing reaction is referred to as a sequencing primer.

A "sequence variation" refers to a point or region of variation between two related nucleic acid molecules (e.g., at least 50% sequence identity and usually, at least 75%, 90, 95 or 99% sequence identity). A variation can be an insertion, deletion or substitution of one or more nucleobase differences between two nucleic acid molecules. A variation can be natural, such as allelic, or between species, strains or isolates or induced. Variations can be between different molecules of viral nucleic acids in a sample. Variations can be germline or somatic. A variation in nucleotide sequence can have no effect on an encoded amino acid sequence due to degeneracy of the code or can result in a corresponding amino acid change. If there is an amino acid change, the change may or may not affect the function of the encoded protein. If the change is to a stop codon, the encoded protein becomes prematurely truncated.

A copy of an anchor segment or adjacent segment or read thereof means an identical copy or substantially identical copy (e.g., at least 80% sequence identity) differing as a result of nucleobase unit misincorporations in template-dependent extension or sequencing errors.

Description of a range by integers representing the boundaries of the range also refers to all subranges defined by integers within the range.

BRIEF DESCRIPTION OF THE DRAWINGS

FIGS. 3A-F show sequencing using hairpin anchor segments.

DETAILED DESCRIPTION

I. General

Figure 1:
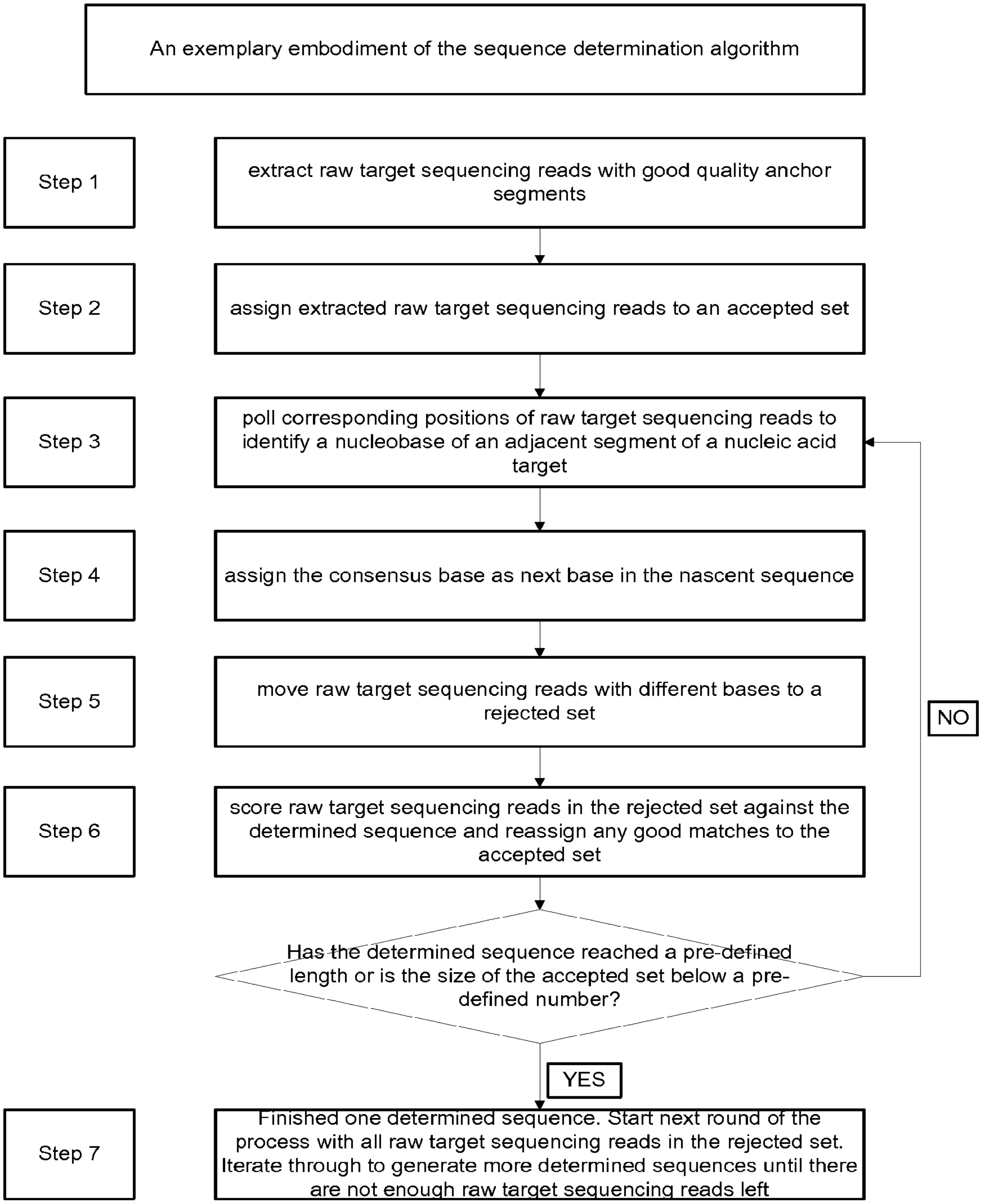
FIG. 1 shows a sequence determination algorithm.

The invention provides methods of determining a consensus sequence from multiple raw sequencing reads of a nucleic acid target. The nucleic acid target includes an anchor segment of known sequence and an adjacent segment of unknown sequence. The anchor segment provides a means to assess the quality of a raw target sequencing read. Because the anchor segment is of known sequence, comparison of the portion of the raw target sequencing read corresponding to the anchor segment provides a measure of quality of the raw target sequencing read. Raw target sequence reads exceeding a threshold level of accuracy are used in determining a consensus sequence for the adjacent target sequence. Raw target sequencing reads not meeting the threshold level of accuracy can be excluded from subsequent analysis.

The consensus sequence of the adjacent segment can be determined from raw target sequencing reads passing the threshold test by polling the target sequence reads at a corresponding position starting with a position adjacent the anchor segment. Successive polling steps can determine successive consensus nucleobases in a nascent sequence of the adjacent segment. Raw target sequencing reads can be removed or reintroduced from the accepted class depending on their correspondence to the most recently determined consensus nucleobase and/or the nascent sequence.

II. Nucleic Acid Target and Sequencing Read Thereof

The nucleic acid unit that is subject of a sequencing reaction and gives rise to a sequencing read (or two sequencing reads from opposing strands) is referred to as a nucleic acid target. A nucleic acid target can be single- or double-stranded, RNA or DNA. A nucleic acid target can be linear or circular. A nucleic acid target includes an anchor segment of known sequence and an adjacent segment whose sequence is to be determined. The adjacent segment can have a single unique sequence, can be a simple mixture of two variants (e.g., bi-allelic variants) or a complex mixture of variant sequences (e.g., a particular mRNA from a viral sample in which multiple viral strains are represented). The nucleic acid target can be of any length but preferably less than 200%, more preferably from 50% to 200%, of the maximum length of raw target sequencing read obtainable with whatever methodology is used. For example, the length of the nucleic acid target is sometimes from 20-50,000 nucleobases or bp for a double stranded nucleic acid target. The nucleic acid target or its adjacent segment can be part of a larger target molecule, such as a gene, viral genome, chromosome or full genome. In this case, as in other sequencing methods, the larger target molecule can be broken down into fragments each of which can constitute a nucleic acid target or an adjacent segment of a nucleic acid target for purposes of the present methods. The sequences of multiple nucleic acid targets or adjacent segments thereof can be compiled from overlaps to provide the sequence of a larger nucleic acid molecule.

The anchor segment refers to a segment of known sequence present in the nucleic acid target. Anchors can be or various lengths, e.g., 8-30, 4-10, 4-20, 4-30, 4-50, or 4-120 nucleobases or base pairs). Anchor segments can be formed from deoxyribonucleotides or ribonucleotides or in some cases nucleotide analogs that can be subject of sequencing reactions.

Anchor segments can be nucleic acid sequences that are heterologous (i.e., not naturally associated with adjacent segment). Examples of heterologous anchor segments include primers or portions thereof used in amplifying adjacent segments, binding sites for sequencing primers, oligonucleotides ligated or otherwise attached to adjacent segments, such as SMRT Bell™ hairpin structures. Such ligated oligonucleotides including SMRT Bell structures can also serve as primer binding sites. Anchor segments can also be nucleic acid sequences naturally associated with the adjacent nucleic acid segment. Examples of anchor segments that are endogenous to the nucleic acid template include portions of a gene of known sequence, regulatory sequences, and repetitive sequences. The anchor segment preferably has a single (i.e., without sequence variation) completely known sequence. However, anchor segments which are of substantially completely known sequences, i.e., at least 80, 95, or 99% of nucleobases are known and without nucleobase variation can also be used.

Many sequencing methods already incorporate a segment that can serve as an anchor segment in the course of preparing a sequence template. In SMRT™ technology, a nucleic acid to be sequenced is ligated to hairpin structures (the same or different from each other), which can serve as anchor segments, one anchor segment joining at each end, forming circular template. The circular template includes strands of the nucleic acid to be sequenced (adjacent segment) and the hairpin anchor segments. Such a circular template can be sequenced in a single well to generate a sequencing read including alternating target strand and anchor segments (e.g., anchor segment 1, first strand of adjacent segment, anchor segment 2, second strand of target segment, anchor segment 1, first strand of adjacent segment, anchor segment 2, second strand of target segment and so forth) Oligonucleotide anchors can be ligated to libraries of nucleic acids to be sequenced (Illumina, Inc., 454 Corporation, SOLiD). Primers for the extension of a polynucleotide complementary to a nucleic acid to be sequenced e.g., poly (T) oligonucleotides, can also be used as anchors. Target nucleic acids can contain one, two or more copies of an anchor segment, each copy interspersed between copies of the adjacent segment (and/or its complement).

Performing a sequencing reaction on a nucleic acid target gives rise to a population of raw target sequencing reads of the nucleic acid target. A raw target sequencing read includes sequence of both the adapter segment and adjacent segment. The length of raw target sequencing of the same target can show some variation. A raw target sequencing read of an anchor segment and an adjacent segment can include the complete anchor segment or a designated portion of at least 10, 15, 20 or 30 nucleotides thereof abutting an adjacent sequence, and at least some, and preferably at least 25, 50, 75, 95 or 100% of the adjacent segment. A raw target sequence read refers to a contiguous nucleobase sequence assigned during a sequencing reaction performed on nucleic acid target. If the nucleic acid is double-stranded, the raw target sequencing read can correspond to either strand of the nucleic acid target. If the nucleic acid target is single-stranded, the raw target sequencing read can correspond to the nucleic acid target strand or its complement. The sequencing reaction can be performed using any type of sequencing methodology. Depending on the type of sequencing methodology used, the reaction provides a series of signals that are individually interpreted to mean one of A, C, T, G or U (or analogs thereof). This initial assignment of contiguous nucleobases forming the raw target sequence read may contain one or more errors (i.e., insertions, deletions, substitutions and combinations thereof). Different raw target sequences of the same nucleic acid target typically contain errors in different positions. Errors can result from misincorporation of nucleotides in amplification or sequencing, reading errors associated with instrumentation and the enzymatic sequencing process, and errors introduced in base-calling.

Raw target sequencing reads can be in the form first generated by a sequencing reaction without any processing to remove errors or can have been subject to partial processing to remove some errors but in which some sequencing errors remain.

A population of raw target sequencing reads of a nucleic acid target can be generated by repeatedly sequencing the same nucleic acid target molecule, sequencing a nucleic acid containing multiple copies of the nucleic acid target (e.g., repeats generated by rolling circle replication), or by sequencing multiple individual copies of the nucleic acid target or larger molecule containing some or all of the nucleic acid target. Examples of methods of generating replicate sequence information from a single molecule are provided, e.g., in U.S. Pat. No. 7,476,503; US 2009/0298075, 2010/0075309, 2010/0075327, 2010/0081143. For example, a circular template can be used to generate replicate sequence reads of the target sequence by allowing a polymerase to synthesize a linear concatemer by continuously generating a nascent strand from multiple passes around the template molecule. The nascent strand can contain alternating reads of an anchor segment and adjacent segment. Optionally, the anchor segment itself alternates between first and second anchor segment and the adjacent segment alternates between its two strands. The population of raw target sequencing reads of a nucleic acid target may or may not begin and end at the same position as each other. However, a nucleic acid read should include at least sufficient numbers of nucleobases of the anchor segment to permit evaluation of accuracy of sequencing of the anchor segment, and at least some of the adjacent segment. Preferably raw target sequencing reads of the same target nucleic acid begin at the same point, include all of an anchor segment and as much of an adjacent segment as is compatible with the sequencing technology. Often there is some variation in the read length of different raw sequencing reads, which is preferably reflected in variation of the length of adjacent segment included in the read. The read lengths of different sequencing technology vary widely. Thus, the amount of adjacent sequence included in a read length can vary from e.g., 10 nucleobases to 50,000 nucleobases.

Raw target sequencing reads may or may not be provided with additional information as well as pure sequence data. Additional information can include estimations of per-position accuracy, features of underlying sequencing technology output (e.g., trace characteristics, integrated counts per peak, shape/height/width of peaks, distance to neighboring peaks), signal-to-noise ratios, power-to-noise ratio, signal strength, and the like.

III. Generation of a Population of Raw Target Sequencing Reads of a Nucleic Acid Target (a) Template Preparation Nucleic acid targets can be amplified before sequencing, or not amplified and used directly in sequencing. Amplification can be performed with a pair of forward and reverse primers as in conventional PCR. Optionally the forward and reverse primers include 5' tails lacking complementary to the nucleic acid being amplified. Such tails can serve to provide a binding site for sequencing primers. Some or all of the forward and/or reverse primer can be used as the anchor segment of the nucleic acid target. The forward and reverse primers can serve as anchor segments for the opposing strands of a double-stranded nucleic acid target.

In other methods, after fragmenting a nucleic acid and repairing fragment ends, if needed, hairpin anchors can be ligated onto the ends of these fragments therefore forming a circularized template for sequencing. FIG. 3A shows a sample preparation using two hairpin anchors termed anchors I and II.

A DNA polymerase can be used to open the anchor-ligated fragments into circularized templates. The anchors serve as binding sites for sequencing primer(s) as well as their role in assessing quality of sequencing reads in the present methods. FIG. 3B shows generation of continuous reads of both strands of a fragment interspersed with anchors I and II. The reads, then, include multiple reads of the same fragment by the polymerase reading around the circular template multiple times. In FIG. 3B, four reads of forward strand and three reads of reverse strand have been generated before the sequencing reaction is terminated.

For analysis, the different sequencing reads can be segregated by an anchor segment. In this example, raw target sequences can be grouped into four subsets. In the first set, anchor I segments are aligned to provide a framework for base-polling sequences of forward strands adjacent to the 3' end of the anchor I segment (FIG. 3C). In the second set, anchor II segments are aligned to provide a framework for base-polling sequences of reverse strands adjacent to the 3' end of the anchor II (FIG. 3E). In the third and fourth sets, anchor I or II segments are aligned to provide frameworks for base-polling sequences of forward strands (FIG. 3F) and reverse strands (FIG. 3D) adjacent to the 5' end of the anchor I and H. Anchors I and II can be the same or different from one another in terms of sequence.

Some amplification methods amplify many nucleic acid molecules in parallel. One such method is amplification on beads using emulsion PCR methods (see, e.g., US US2005/0042648, US2005/0079510, and US2005/0130173 and WO 05/010145). Another such method is amplification on a surface using bridge amplification to form nucleic acid clusters. Methods of generating nucleic acid clusters for use in high-throughput nucleic acid sequencing have been described (see, e.g., U.S. Pat. No. 7,115,400, US 2005/0100900 and 2005/0059048, and WO 98/44151, WO 00/18957, WO 02/46456, WO 06/064199, and WO 07/010251. Bridge amplification refers to a solid phase replication method in which primers are bound to a solid phase, e.g., flow cell, microarray, and the like. The extension product from one bound primer forms a bridge to the other bound primer.

(b) Sequencing

One class of sequencing reactions that can be used are sequencing-by-synthesis (SBS) methods. Sequencing by synthesis refers to the sequencing of a nucleic acid sequence by synthesis of the complementary strand (see US 2007/0166705, 2006/0188901, 2006/0240439, 2005/0100900, 2006/0281109; U.S. Pat. No. 7,057,026; WO 05/065814, WO 06/064199 and WO 07/010251).

SBS techniques can utilize nucleotide monomers that have a label moiety or those that lack a label moiety. If a label is present, the monomers can have the same or different label as each other. If present, incorporation events can be detected based on a characteristic of the label(s), such as fluorescence of the label(s); a characteristic of the nucleotides such as molecular weight or charge; a byproduct of incorporation of the nucleotides, such as release of pyrophosphate or a hydrogen ion; or the like.

In some methods, the incorporation of nucleobase units is detected by measuring the release of a label from the nucleobase unit being incorporated. A preferred approach as with SMRTbell™ template sequence is to use nucleobase units fluorescently labeled on the terminal phosphate of the nucleobase unit. (Korlach et al., *Nucleosides, Nucleotides and Nucleic Acids,* 27:1072-1083, 2008. The label is cleaved from the nucleotide monomer on incorporation of the nucleotide into the polynucleotide. Accordingly, the label is not incorporated into a nascent nucleic acid, increasing the signal:background ratio.

Pyrosequencing detects the release of inorganic pyrophosphate (PPi) as particular nucleotides are incorporated into the nascent strand (Ronaghi, et al., *Analytical Biochemistry* 242(1):84-9, 1996; Ronaghi, M., *Genome Res.* 11(1):3-11, 2001; Ronaghi, et al., *Science* 281(5375):363, 1998; U.S. Pat. Nos. 6,210,891, 6,258,568 and 6,274,320). Released PPi can be detected by, e.g., a process in which the released PPi is immediately converted to adenosine triphosphate (ATP) by ATP sulfurylase, and the level of ATP generated is detected via luciferase-produced photons.

A hydrogen ion released on incorporation of a nucleotide can be detected as a change in voltage by for example the Ion Torrent machine (Life Technologies, Inc).

In another example, cycle sequencing is accomplished by stepwise addition of reversible terminator nucleotides containing, for example, a cleavable or photobleachable dye label. The technique was commercialized by Solexa (now Illumina Inc.), and described, for example, in U.S. Pat. Nos. 7,427,67, 7,414,163 and 7,057,026, and WO 91/06678 and WO 07/123744. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides. In cases where two or more different nucleotides are present in a sequencing reagent, the different nucleotides can be distinguishable from each other. For example, the different nucleotides present in a sequencing reagent can have different labels and they can be distinguished using appropriate optics as exemplified by the sequencing methods developed by Solexa (now Illumina, Inc.).

SBS can utilize nucleotide monomers that have a terminator moiety or those that lack any terminator moieties. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.). Methods utilizing nucleotide monomers lacking terminators include, for example, pyrosequencing and sequencing using γ-phosphate-labeled nucleotides. In methods using nucleotide monomers lacking terminators, the number of different nucleotides added in each cycle can be dependent upon the template sequence and the mode of nucleotide delivery. Reversible terminators/cleavable fluors can include fluor linked to the ribose moiety via a 3' ester linkage (Metzker, *Genuine Res.* 15:1767-1776 (2005). Other approaches have separated the terminator chemistry from the cleavage of the fluorescence label (Ruparel et al., *Proc. Natl. Acad. Sci. USA* 102: 5932-7 (2005). Ruparel et al. described the development of reversible terminators that used a small 3' allyl group to block extension, but could easily be deblocked by a short treatment with a palladium catalyst. The fluorophore was attached to the nucleobase via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination (see U.S. Pat. Nos. 7,427,673 and 7,057,026).

Another class of sequencing reactions that can be used are nanopore sequencing methods. In nanopore sequencing, (Deamer, & Akeson, *Trends Biotechnol.* 18:147-151 (2000); Deamer & Branton, *Acc. Chem. Res.* 35:817-825 (2002); Li, et al., *Nat. Mater.* 2:611-615 (2003)), the target nucleic acid or nucleotides released from the target nucleic acid pass through a nanopore. The nanopore can be a synthetic pore or biological membrane protein, such as α-hemolysin. As the target nucleic acid or nucleotides pass through the nanopore, each base-pair (or base) can be identified by measuring fluctuations in the electrical conductance of the pore. (U.S. Pat. No. 7,001,792; Soni, G. V. & Meller, *Clin. Chem.* 53:1996-2001 (2007); Healy, K., *Nanomed.* 2:459-481 (2007); Cockroft, et al., *J. Am. Chem. Soc.* 130:818-820 (2008)).

Another class of sequencing reactions is sequencing by ligation (see U.S. Pat. Nos. 6,969,488, 6,172,218, and U.S. Pat. No. 6,306,597). A target nucleic acid is hybridized to an oligonucleotide and contacted with several probes and a ligase. Only a probe complementary to the target nucleic acid can be ligated to the oligonucleotide. The identity of the probe indicates part of the sequence of the target nucleic acid.

(c) Sequencing Platforms

Examples of sequencing platforms include the Genome Sequencer FLX System (Roche) that employs pyrosequencing to provide long read lengths and very high single-read accuracy, 454 FLX™ or 454 TITANIUM™ (Roche), the SOLEXA™ Genome Analyzer (Illumina), the HELISCOPE™ Single Molecule Sequencer (Helicos Biosciences), the SOLID™ DNA Sequencer (Life Technologies/Applied Biosystems) instruments) which performs sequencing by ligation, SMRT™ technology (Pacific Biosystems), Ion Torrent (LifeTech) as well as other platforms still under development by companies such as Intelligent Biosystems. Other sequencing platforms include OmniMoRA (Reveo, Inc. (Elmsford, N.Y.)), VisiGen® (VisiGen Biotechnologies, Inc. (Houston, Tex.), now Life Technologies (Carlsbad, Calif.)), SBS technology (Intelligent Bio-Systems (Waltham, Mass.)), or Hybridization-Assisted Nanopore Sequencing (HANS; NABsys Inc. (Providence, R.I.)), or the target fragment isolated may be sent to a third party for further analysis and/or sequencing (e.g., Really Tiny Stuff, Inc., Cohasset, Mass.).

A sequencing platform provided by Helicos Biosciences Corp. uses TRUE SINGLE MOLECULE SEQUENCING (tSMS)™ technique (Harris et al., *Science* 320:106-109 (2008). The tSMS™ technique uses a library of target nucleic acids prepared by the addition of a 3' poly(A) tail to each target nucleic acid. The poly(A) tail hybridizes to poly(T) oligonucleotides anchored on a glass cover slip. The poly(T) oligonucleotide can be used as a primer for the extension of a polynucleotide complementary to the target nucleic acid.

Sequencing platforms implementing real-time monitoring of DNA polymerase activity can be used. For example, nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414. Nucleotide incorporations can also be detected with zero-mode waveguides as described, for example, in U.S. Pat. No. 7,315,019 and using fluorescent nucleotide analogs and engineered polymerases as described, for example, in U.S. Pat. No. 7,405,281 and US 2008/0108082. The illumination can be restricted to a zeptoliter-scale volume around a surface-tethered polymerase such that incorporation of fluorescently labeled nucleotides can be observed with low background (Levene et al., *Science* 299:682-686 (2003); Lundquist et al., *Opt. Lett.* 33:1026-1028 (2008); Korlach et al., *Proc. Natl. Acad. Sci. USA* 105:1176-1181 (2008).

Single-molecule, real-time (SMRT™) DNA sequencing technology is described in U.S. Pat. Nos. 7,181,122, 7,302,146, and 7,313,308. SMRT chips and similar technology can be used in association with nucleotide monomers fluorescently labeled on the terminal phosphate of the nucleotide (Korlach et al., *Nucleosides, Nucleotides and Nucleic Acids,* 27:1072-1083, 2008). The label is cleaved from the nucleotide monomer on incorporation of the nucleotide into the polynucleotide. Accordingly, the label is not incorporated into the polynucleotide, increasing the signal:background ratio.

(d) Multiplexing

As already described, some amplification methods amplify multiple nucleic acids in parallel. Sequencing reactions can also be carried out in multiplex formats such that multiple different nucleic acid targets are manipulated simultaneously. For example, different nucleic acid targets can be treated in a common reaction vessel or on a surface of a particular substrate. This allows convenient delivery of sequencing reagents, removal of unreacted reagents and detection of incorporation events in a multiplex manner. Nucleic acid targets can also be in an array format in a spatially distinguishable manner. The target nucleic acids can be bound by direct covalent attachment, attachment to a bead or other particle or binding to a polymerase or other molecule that is attached to the surface. The array can include a single copy of a nucleic acid target at each site (also referred to as a feature) or multiple copies having the same sequence can be present at each site or feature.

In deep sequencing a plurality of related or identical nucleic acids are attached to the surface of a reaction platform (e.g., flow cell, microarray, and the like) (see e.g., Bentley et al., *Nature* 2008, 456:53-59). The attached DNA molecules can be amplified in situ and used as templates for synthetic sequencing (i.e., sequencing by synthesis) using a detectable label (e.g. fluorescent reversible terminator deoxyribonucleotide). Representative reversible terminator deoxyribonucleotides include 3'-O-azidomethyl-2'-deoxynucleoside triphosphates of adenine, cytosine, guanine and thymine, each labeled with a different recognizable and removable fluorophore, optionally attached via a linker. When fluorescent tags are employed, after each cycle of incorporation, the identity of the inserted base may be determined by excitation (e.g., laser-induced excitation) of the fluorophores and imaging of the resulting immobilized growing duplex nucleic acid. The fluorophore, and optionally linker, can be removed by conventional methods, thereby regenerating a 3' hydroxyl group ready for the next cycle of nucleotide addition.

IV. Determining a Consensus Sequence

The present methods can be used to provide a consensus sequence of at least part of the adjacent segment in a nucleic acid target from a population of raw target sequencing reads of the target. If an initial population of raw target sequences do not all contain the same anchor segment, the population can be sorted to give a population of raw target sequencing reads in which part of the sequencing read is of the same anchor segment. The members of this population are then evaluated for accuracy of sequencing of the anchor segment. Members of the population in which the accuracy at least reaches (and preferably exceeds) a threshold value are carried forward for subsequent consensus sequence determination. The raw target sequencing reads carried forward are designated in a class of accepted raw sequencing reads and can be literally or conceptually assigned to an accepted class. This class is usually in the form of stored information in computer system. Members of the population failing to reach the threshold value are typically discarded and not further used in the analysis. The threshold value can be based on the percentage sequence identity between the segment of a raw target sequencing read and corresponding known sequence of an anchor segment and/or the location of matched and mismatched nucleotides between. Sequence identity is preferably determined over the full length of the known sequence of the anchor segment maximally aligned with the raw target sequencing read. Sequence identity is scored as the number of matched nucleotides divided by the number of nucleotides in the anchor segment. The sequence identity is preferably at least 80, 85, 90, 95, 99 or 100%. The threshold can additionally or alternatively be defined by the location of matched nucleotides. The nucleotide immediately adjacent to the first nucleobase of the portion of the sequencing read corresponding to the adjacent segment is particularly significant. Thus, the threshold can require this nucleobase to be accurately determined. The threshold can require a contiguous segment of at least 2, 3, 4, 5, 6, 7, 8, 9 or 10 nucleobases adjacent the first nucleobase of corresponding to the adjacent segment to be correctly determined.

Having selected a subset of raw target sequencing reads in which the accuracy of the portion of the read corresponding to an anchor segment exceeds a threshold, a consensus of the portions of the sequencing reads corresponding to the adjacent segment can be determined by a method including any or all of the polling, discarding or reassigning steps described below.

Preferred methods assign successive nucleobases to a nascent sequence of the adjacent sequence by a process referred to as polling. Polling compares nucleobases occupying a corresponding position among raw target sequencing reads to determine a consensus nucleobase at the corresponding position. A consensus nucleobase is the most represented nucleobase in the different raw target sequencing reads being polled at the polled position. If two or more nucleobases are tied for most represented, any of the tied bases can be regarded as the consensus nucleobase. The other tied nucleobases can be treated as non-consensus or can be treated as potential sites of sequences variations as discussed in more detail below. Nucleobases that are not tied, but less represented, can also be treated as potential sites of sequences variations. In most cases, the sites for sequence variations are not tied bases. The position for the initial polling step is defined by reference to the anchor segment so the position is equidistant from the sequence of the anchor segment in the raw target sequencing being polled. Typically the position is immediately adjacent the sequence of the anchor segment in the direction in which the sequencing read is performed (typically beginning at the adapter segment and moving into the adjacent segment). Polling determines the consensus nucleobase at this position and this nucleobase is assigned as a nucleobase of a sequence of the adjacent segment, typically the first base. Raw target sequencing reads having the consensus nucleobase at the position polled are retained as accepted sequences. Raw target sequencing reads lacking the consensus nucleobase at the position polled are designated as rejected raw target sequencing reads. The rejected sequencing reads can literally or conceptually be assigned to a rejected class. The rejected class, like the accepted class, is typically electronic information in computer memory. At this point, some rejected raw target sequencing reads may be reassigned as accepted sequences in a process that will be described in more detail below.

For raw target sequencing reads polled in the previous step and retained as accepted sequences, a further polling step is performed on the next nucleobase (adjacent the nucleobase polled in the previous step). The directionality is usually the same as that in which the raw target sequencing read is developed beginning at or before the anchor segment and moving into the adjacent segment. Thus, for a sequencing-by-synthesis method, the raw target sequencing read is determined in a 5'-3' direction and nucleobases in successive polling steps also usually move along the raw targeting sequences in a 5'-3' direction. However, successive polling steps can also be performed in the opposite directed to that of synthesis (i.e., 3'-5'). Again, a consensus nucleobase is determined at a corresponding position between the accepted raw target sequencing reads, and this nucleobase is assigned as the next nucleobase of the nascent sequence of the adjacent segment. Again, raw target sequencing reads having the consensus nucleobase at the polled position are retained as accepted sequences. Raw target sequencing reads lacking the consensus nucleobase at the polled position are designated as rejected sequences.

Further iterations of the poling step can be performed. A repetition polls a position adjacent the position polled in the previous polling step for accepted raw target sequencing read. The determined consensus nucleobase in successive repetitions form successive nucleobases in the nascent segment of the adjacent segment. After a polling step, raw target sequencing reads having the consensus nucleobase at the polled position are retained as accepted and raw target sequencing reads lacking the consensus nucleobase are designated as rejected.

As mentioned above, in any cycle of the above methods, rejected raw target sequencing reads can be considered for reassignment as accepted raw target sequencing reads. Usually, reassignment, if performed, occurs after the polling step and after any raw target sequencing reads not having the consensus nucleobase in the polling step are assigned as rejected sequencing reads. Reassignment allows the consensus sequence determination to make use of information from raw target sequencing reads that do not conform to the consensus sequence of the adjacent segment in one region but do in one or more other regions. Such lack of conformity may be the result of a sequencing error, a polymorphism, deletions of part of the adjacent segment of the nucleic acid target or a heterogeneous mixture of nucleic acid targets in which adjacent segments do not necessarily begin and end at the same point of a large molecule. Rejected raw target sequencing reads are reassigned based on overall sequence identity with the nascent sequence and/or the location of matched nucleobases between the rejected raw target sequencing read and the nascent sequence. A rejected raw target sequencing read is aligned with the nascent sequence to maximize matched nucleotides. The alignment can be performed over the entire length of the nascent sequence or a window of e.g., the last 10 or 20 nucleobases. Percentage sequence identity can be calculated as the number of matched nucleobases with the nascent sequence minus deletions or insertions divided by the number of nucleobases of the nascent sequence. The calculation can be performed over the entire nascent sequence or a window thereof, for example, the last 20 or 10 nucleobases. The threshold for sequence identity can be defined as at least 80, 85, 90, 95, 99 or 100% over the defined window. Additionally, or alternatively, the threshold can require identity between the last nucleotide determined for the nascent sequence and the corresponding nucleotide of the rejected raw target sequence. The threshold can alternatively require identity between the last 2, 3, 4, 5, 6, 7, 8, 9 or 10 determined nucleotides of the nascent sequence and the corresponding nucleotides of the raw target sequencing read. An exemplary criterion for reassigning a rejected raw target sequencing read to be an accepted raw target sequencing read is an overall sequence identity of at least 80% and identity between the last determined nucleobase of the nascent sequence and corresponding nucleobase of the raw target sequencing read.

Rejected raw targeting sequencing reads can be assessed for reassignment to accepted status in any iteration of the method. The fact that rejected raw targeting sequencing are assessed may or may not result in one or more of them being found to meet the threshold for reassignment to accepted status. In some methods, a reassignment is made in at least one cycle. In some methods, a reassignment is performed at least 5 times in at least 20 cycles. In some methods, a reassignment is performed at least 20 times in at least 100 cycles. Reassignment or at least assessment of rejected raw target sequencing reads for reassignment can also performed at regular intervals, e.g., every 5 or 10 polling steps, or after the first 20 polling steps, and then after each 5 or ten polling steps thereafter.

The interval between a raw target sequencing read being assigned from the accepted to rejected class and then back to accepted can be as short of one cycle. For example, a raw target sequencing read having a single nucleobase insertion can be assigned from accepted to rejected because the inserted nucleobase is not the consensus nucleobase at the relevant position being polled. However, the same raw target sequencing read can then be immediately reassigned because its next nucleobase is the last polled nucleobase in the consensus sequence and it overall meets the threshold criteria for reassignment to accepted status. In this case, the raw target sequence read effectively misses only one nucleobase being read corresponding to the nucleobase insertion. For raw target sequencing reads having a single nucleobase substitution, when the nucleobase occupied by the substitution is polled, the raw target sequencing read does not have the consensus nucleobase and is assigned to the rejected class. However, after the next round of polling, the raw target sequencing read does have a nucleobase the same as the most recently determined nucleobase of the nascent sequence and can be returned to the accepted class (assuming other threshold criteria are met). In this case, the raw target sequencing read has effectively missed two nucleobases being read in determining the consensus sequence, the substituted nucleobase and the next adjacent nucleobase. Other raw target sequencing reads are present in the rejected class of sequences for longer periods or may never be returned to the accepted raw target sequencing reads.

Returning raw target sequencing reads either were not polled in the previous polling cycle, of if polled, yielded a non-consensus nucleobase. In the polling cycle immediately after a raw targeting sequencing read is returned to the accepted class of sequencing reads, the position polled is that immediately adjacent to the position aligned with the last nucleobase determined in the nascent sequence so as to permit assessment of the next nucleobase in the nascent sequence Immediately returning raw sequencing reads are polled together with raw target sequences already having accepted status to determine a consensus nucleobase. If a returning raw target sequencing read remains in the accepted category following its initial return, positions for subsequent polling can be determined as for other raw targeting reads in the accepted category. That is, the position for one polling cycle is the position adjacent that in the previous polling cycle preserving a directionality throughout polling such that successive nucleobases in the nascent sequence are determined. For raw sequencing reads generated in a 5'-3' orientation, the directionality of polling successive nucleobases is also usually 5'-3' but can also be 3'-5'.

The steps of polling, and assigning raw target sequencing reads are continued assigning successive nucleobases to the nascent sequence until a sufficient length of nascent sequence has been determined or the complete length of the adjacent segment has been determined or the number of raw target sequencing reads in the accepted class falls below a threshold limit. The accuracy of raw target sequencing reads typically reduces further along the read. As the accuracy is reduced, more raw target sequencing reads are designated as rejected sequencing reads and fewer, if any, are returned to the accepted class. The number of cycles of polling (and auxiliary assigning and reassigning steps) depends on the length of the adjacent segment and the length of reasonably accurate sequencing read, which in turn depends on the sequencing technique. Depending on the sequencing technique, the number of polling cycles can be e.g., at least 2, 5, 10, 50, 100, 200, 1000, 10,000 or 50,000.

The process described above identifies the consensus nucleobases occupying successive positions of the nascent sequence. The process can be varied or extended to determine variants of the consensus sequence as well. The variations can be allelic variations, variations between isolates, strains or species, or sequence variations between a population of viral molecules in a clinical sample, among others. Such variations can be identified by forming branched consensus sequences as the method described above is performed or by repeating the method on raw target sequencing reads that have been rejected at one or more cycles of the method. Branching starts by identifying two (or more) consensus nucleobases in a polling step. The nucleobases may have the same or similar representation in the accepted raw target sequencing reads, or one nucleobase may have higher representation than the other but both nucleobases still have a representation exceeding a threshold. In this situation, the nascent sequence is branched into two nascent sequences with the two consensus nucleobases being the first nucleobases in the two branched arms of the nascent sequence. Raw target sequencing reads having either of the consensus nucleobases are retained in the accepted class. Subsequent consensus nucleobases are assigned to both branched nascent sequences. A branched nascent sequence can itself be subject of further branching at a further position of sequence variation.

Alternatively of additionally, a consensus sequence of the adjacent segment can be determined without branching and the process repeated using raw targeting sequences that have been rejected in at least one cycle and preferably returned to the accepted class subsequently. These sequences are a likely source of sequence variants because a raw targeting sequencing read will be rejected if it includes one or more nucleobase differing from the consensus but can then be returned to the accepted class based on identity between one or more subsequently determined nucleobases and the consensus nucleobase. Performing further iterations of the method on raw targeting sequencing reads that have returned to the accepted class can thus be used to identify one or more variants of the initially determined consensus sequence of the adjacent segment.

Once the sequence of an unknown adjacent segment has been determined by repeated polling and discarding subreads as described above, the process can be repeated starting with raw target sequencing reads in the rejected class after performing the process. If the initial population of raw target sequencing reads including sequencing reads of multiple nucleic acid targets includes the same anchor segment linked to different adjacent segments, repeating the method can be used to determine the sequence of a different adjacent segment. The method initially determines the sequence of the predominant adjacent segment in such a mixture, with nucleic acid targets containing other adjacent segments being designated as rejected sequences. Repeating the method on the rejected sequences, thus allows determination of a consensus sequence for a second and different adjacent segment. The method can be repeated multiple times to determine the consensus sequence of multiple different adjacent segments.

An initial population of raw target sequencing reads sometimes includes sequencing reads of nucleic acid target incorporating different anchor segments. Different anchor segments can be used to distinguish reads of opposing strands of an adjacent segment or different adjacent segments. If different segments, the segments can be overlapping or part of the same larger nucleic acid molecule (e.g., a genome or chromosome). In this case, the raw target sequencing reads can usually be segregated by anchor segment so as to be in groups in which the read is that of the same anchor segment. The above methods can be applied separately to the raw target sequencing reads in the same group.

In a further variation, after determining a consensus sequence of an adjacent segment, part of the consensus sequence is itself used as an anchor segment in an additional iteration of the method. The additional iteration can start with sequences in the rejected class and/or any sequences remaining in the accepted class. The adjacent segment for the new anchor segment can overlap in full, in part or not at all with adjacent segment from the first iteration. If the adjacent segment overlaps completely, then the additional iteration provides a check and possible identification and correction of errors in the consensus sequence. If the adjacent segment is completely beyond the prior adjacent segment, then an additional consensus sequence is determined contiguous with the consensus sequence initially determined. If the additional adjacent segment is partially within and partially beyond the prior adjacent segment, then it both checks and extends the consensus read from the prior adjacent segment.

The result of the above method is at least a consensus sequence of a part of an adjacent segment. Sometimes alternative consensus sequences including a sequence variation are also provided. Sometimes consensus sequences for both strands of an adjacent segment are provided. Sometimes consensus sequences of multiple adjacent segments are provided. If consensus sequences are provided for both strands of an adjacent segment and there are any discrepancies, the discrepancies can be rechecked, optionally using an alternative sequencing method. As already noted forward and reverse sequences can be readily generated using certain sequencing platforms such as SMRT technology. Discrepancies sometimes arise from reading a particular nucleobase but not its complementary nucleobase. If consensus sequences are provided for multiple adjacent segments that are part of the same larger nucleic acid molecule the sequences can be combined based on overlaps by conventional methods.

Determining sequence variations requires distinguishing between sequencing errors and true sequence variations. Such a distinction can be made by setting certain filtering criteria, or by setting a rank threshold such as a quality score. One example of a filter for identifying error or variant at any given position is to quantify the number of times each nucleobase appeared at a given position. The nucleobase that occurs the majority of the time is likely the correct residue for that position. For the remaining non-majority nucleobases that appeared at a given position, if their occurrence is relatively even meaning about 33% for each, then is can be determined that for this given position, the mismatches were errors. On the other hand, should one of the remaining non-majority nucleobases appear more frequently than the others, then that nucleobase is likely the correct nucleobase of a minority species variant. Of course, quantifying the relative occurrence of the non-majority nucleobases should take into account the statistical significance of any differences in occurrences. An example of a quality metric is a Phred score (Hillier et al., Genome Res. 8(3):175-185, 1998). for Sanger sequencing, which is calculated based on fluorescent signal characteristics for the 4 nucleobase channels at a given position. A high Phred score for a predominant non-majority nucleobase at a given position would be an indication that the variant is present in a legitimate minority species. It is often useful to calculate a log odds ratio based on quality scores for each potential nucleobase. The log odds ratio is the natural log of the ratio of odds that a nucleobase is present based on experimental data, and represents the likelihood that a particular nucleobase was correctly read at a given position. Thus, a high log odds ratio for the predominant non-majority nucleobase at a given position suggests that it is a valid nucleobase at that position in a legitimate minority species.

Sequencing errors and true sequence variations can be further distinguished by comparing determined sequences of multiple adjacent segments. For example, adjacent segments covering different but partially overlapping regions of a larger nucleic acid molecule suspected of having the sequence variations can be compared. True sequence variations are more likely to appear in most, if not all, partially overlapping sequences. Special care should be taken, however, when phasing multiple SNPs within chromosomes. For example, when phasing multiple SNPS within chromosomes, it is possible that all SNPs are located in only one allele. In these cases, data generated from each allele should not be combined. Preferably, determined sequences from each allele should be compared against each other to phase multiple SNPs.

FIG. 1 provides an overview of an exemplary analysis schema for analyzing a target nucleic acid. At step 1, raw target sequencing reads were selected to create a class of raw target sequencing reads having high-quality reads of the anchor segment. Different criteria can be applied in extracting such raw target sequencing reads. For examples, raw target sequencing reads preferably include only reads having sequences that are 100% identical to the known, correct anchor segment sequence. Optionally, reads can be filtered to create a class of raw target sequencing reads having sequences that are at least 99%, 95%, 90%, 85%, 80%, 75%, or 70% identical to the known, correct anchor segment sequence. Filtering criteria are used for evaluating the accuracy of the sequencing, and can be adjusted based on various parameters, e.g., the number of subreads having high-quality reads of the anchor segment. Raw target sequencing reads that meet pre-determined criteria are accepted for base-polling (see step 2 of FIG. 1).

VII. Computer Implementation

The present methods can be computer-implemented, such that at least one or more (e.g., at least 2, 3, 4, 5, 6, 7, or 8), or all steps of the method are carried out by a computer program (except wet chemical steps). The present methods can be implemented in a computer program stored on computer-readable media, such as the hard drive of a standard computer. A computer program for analyzing a nucleic acid target can include one or more of the following codes: (a) code for receiving a population of raw target sequencing reads of a nucleic acid target comprising an anchor segment and an adjacent segment, (b) code for evaluating the accuracy of sequencing of the anchor segment in different raw target sequencing reads by comparing raw target sequencing reads of the anchor segment with the known sequence of the anchor segment, (c) code for assigning a subset of the raw target sequencing reads into an accepted class based on reaching at least a threshold level of accuracy of the sequencing of the anchor segment, (d) code for polling nucleobases at a position equidistant to the anchor segment sequence in raw target sequencing reads in the accepted class to determine a consensus nucleobase, which consensus nucleobase is assigned as the first nucleobase of a nascent sequence of the adjacent segment, (e) code for assigning raw target sequencing reads having the consensus nucleobase determined in the prior polling step to remain in an accepted class and assigning raw target sequencing reads lacking the consensus nucleobase determined in the prior polling step to the rejected class, (f) code for optionally reassigning a raw target sequencing read from the rejected class to the accepted class by scoring similarity of the raw target sequencing read to the nascent sequence and reintroducing the raw target sequencing read if the sequence similarity reaches at least a threshold level of similarity, and code for repeating steps coded in (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment. A computer program for analyzing a nucleic acid target can also include one or more of the following codes: code for receiving a population of raw target sequences of a nucleic acid target comprising an adapter segment and an adjacent segment, code for evaluating the accuracy of sequencing of the adapter segment in different raw target sequences by raw target sequencing reads of the anchor segment with the known correct sequence of the anchor segment, code for assigning a subset of the raw target sequences into an accepted class based on the accuracy of sequencing of the adapter segment in the raw target sequences, code for aligning at least some of the raw target sequences from the accepted class, code for determining a sequence of at least part of the adjacent segment from the aligned sequences, and a computer-readable storage medium comprising the codes.

The present methods can be implemented in a system (e.g., a data processing system) for analyzing a nucleic acid target. The system can also include a processor, a system bus, a memory coupled to the system bus, wherein the processor is coupled to the system bus for one or more of the following: (a) receiving a population of raw target sequencing reads of a nucleic acid target comprising an anchor segment and an adjacent segment, (b) evaluating the accuracy of sequencing of the anchor segment in different raw target sequencing reads by comparing raw target sequencing reads of the anchor segment with the known sequence of the anchor segment, (c) assigning a subset of the raw target sequencing reads into an accepted class based on reaching at least a threshold level of accuracy of the sequencing of the anchor segment, (d) polling nucleobases at a position equidistant to the anchor segment sequence in raw target sequencing reads in the accepted class to determine a consensus nucleobase, which consensus nucleobase is assigned as the first nucleobase of a nascent sequence of the adjacent segment, (e) assigning raw target sequencing reads having the consensus nucleobase determined in the prior polling step to remain in an accepted class and assigning raw target sequencing reads lacking the consensus nucleobase determined in the prior polling step to the rejected class, (f) optionally reassigning a raw target sequencing read from the rejected class to the accepted class by scoring similarity of the raw target sequencing read to the nascent sequence and reintroducing the raw target sequencing read if the sequence similarity reaches at least a threshold level of similarity, and repeating steps (d), (e) and optionally (f), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment. The system can also include a processor, a system bus, a memory coupled to the system bus, wherein the processor is coupled to the system bus for one or more of the following: receiving a population of raw target sequences of a nucleic acid target comprising an adapter segment and an adjacent segment, evaluating the accuracy of sequencing of the adapter segment in different raw target sequences by comparing raw target sequencing reads of the anchor segment with the known correct sequence for the anchor segment, assigning a subset of the raw target sequences into an accepted class based on the accuracy of sequencing of the adapter segment in the raw target sequences, aligning at least some of the raw target sequences from the accepted class, and determining a sequence of at least part of the adjacent segment from the aligned sequences.

Various steps of the present methods can utilize information and/or programs and generate results that are stored on computer-readable media (e.g., hard drive, auxiliary memory, external memory, server; database, portable memory device (e.g., CD-R, DVD, ZIP disk, flash memory cards), and the like. For example, information used for and results generated by the methods that can be stored on computer-readable media include raw target sequencing reads of a nucleic acid target, the sequence of an anchor segment, the accepted class, the rejected class, the nascent sequence of the adjacent segment, the threshold level of similarity, the threshold level of accuracy of the sequencing the anchor segment, and one or more consensus nucleobase(s). Information used for and results generated by the methods that can be stored on computer-readable media also include raw target sequences of a nucleic acid target, the adapter segments, the accepted class, the partially or fully determined sequences of the unknown segments (i.e., the nucleobases in the adjacent segment adjacent the adapter segment), the discarded raw target sequences, the discarded raw target sequences reassigned to the accepted class, the sequence variations at each position.

The present invention also includes an article of manufacture for analyzing a nucleic acid target that includes a machine-readable medium containing one or more programs which when executed implement the steps of the present methods.

Figure 2:
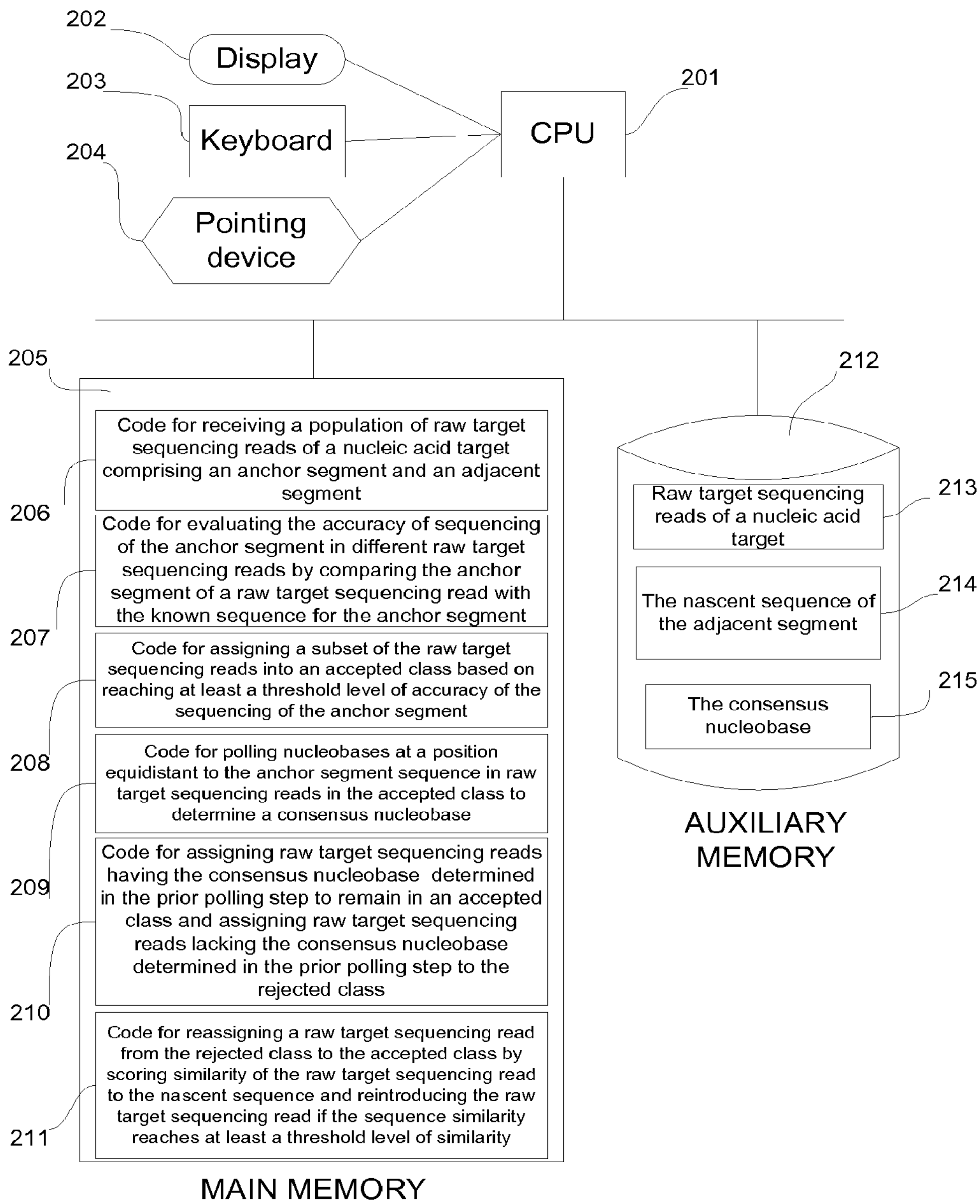
FIG. 2 shows a configuration of a device for analyzing a nucleic acid target.
Figure 4A:
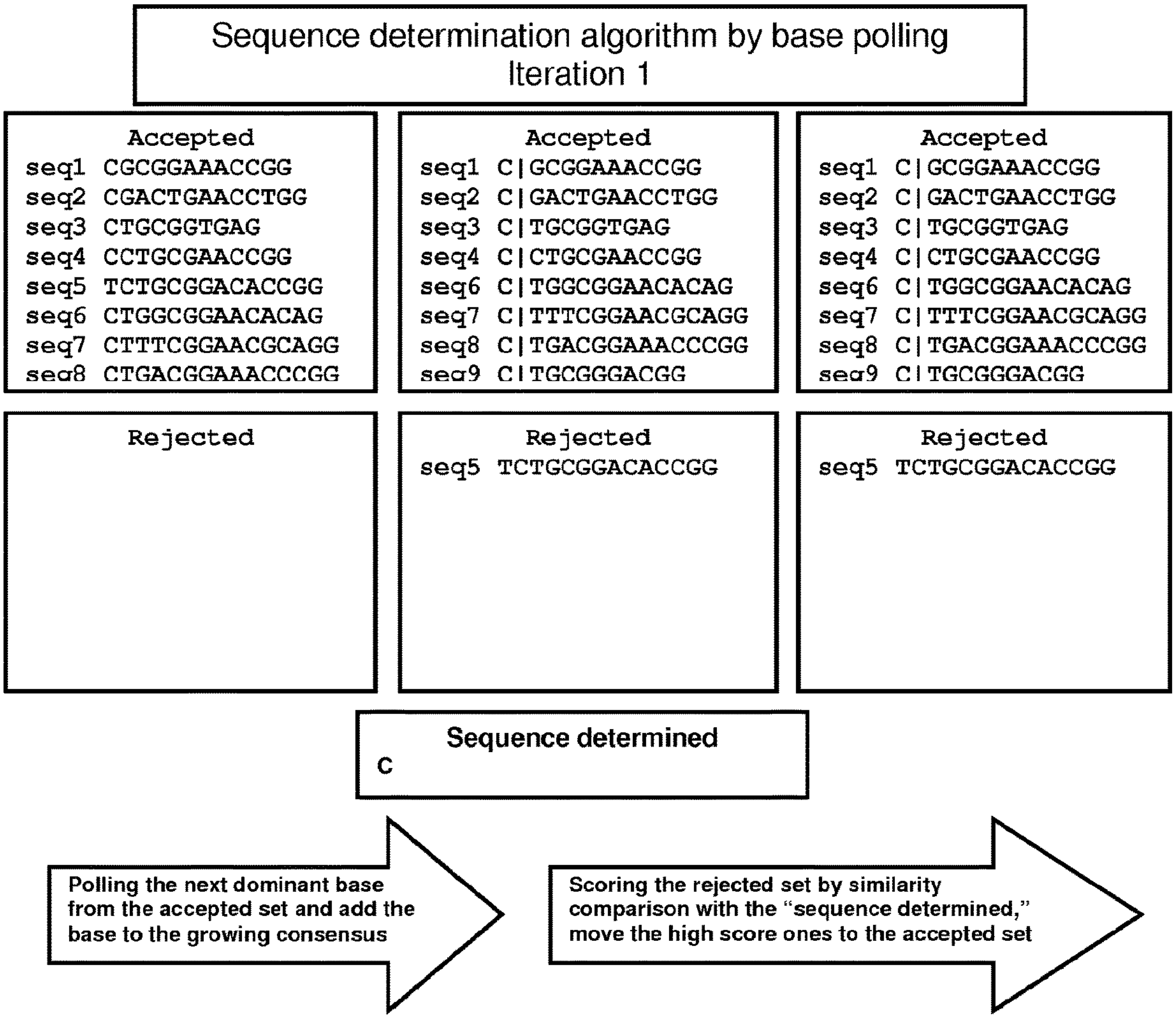
FIGS. 4A-D show determining a consensus sequence by nucleobase polling.
Figure 4B:
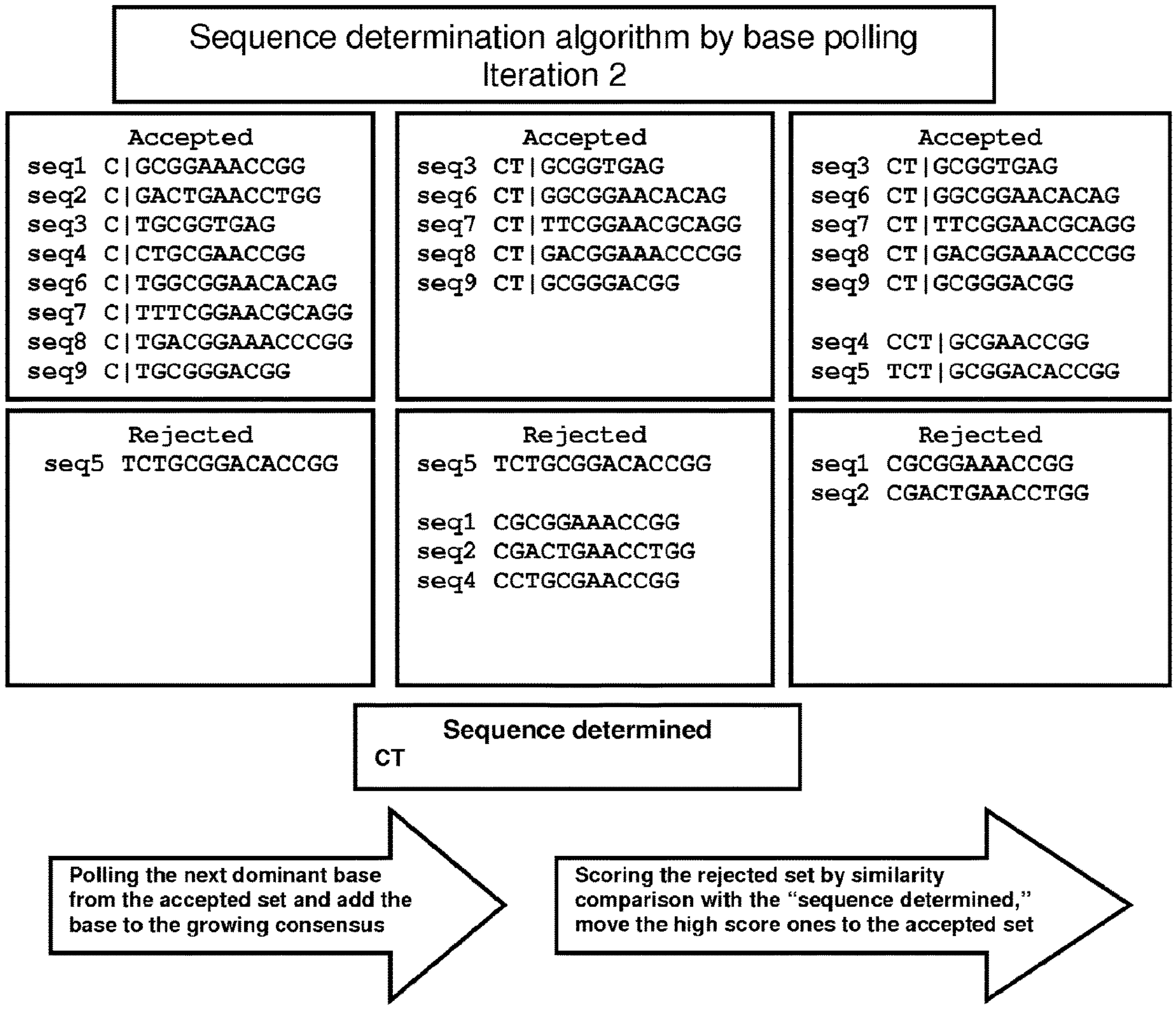
Figure 4C:
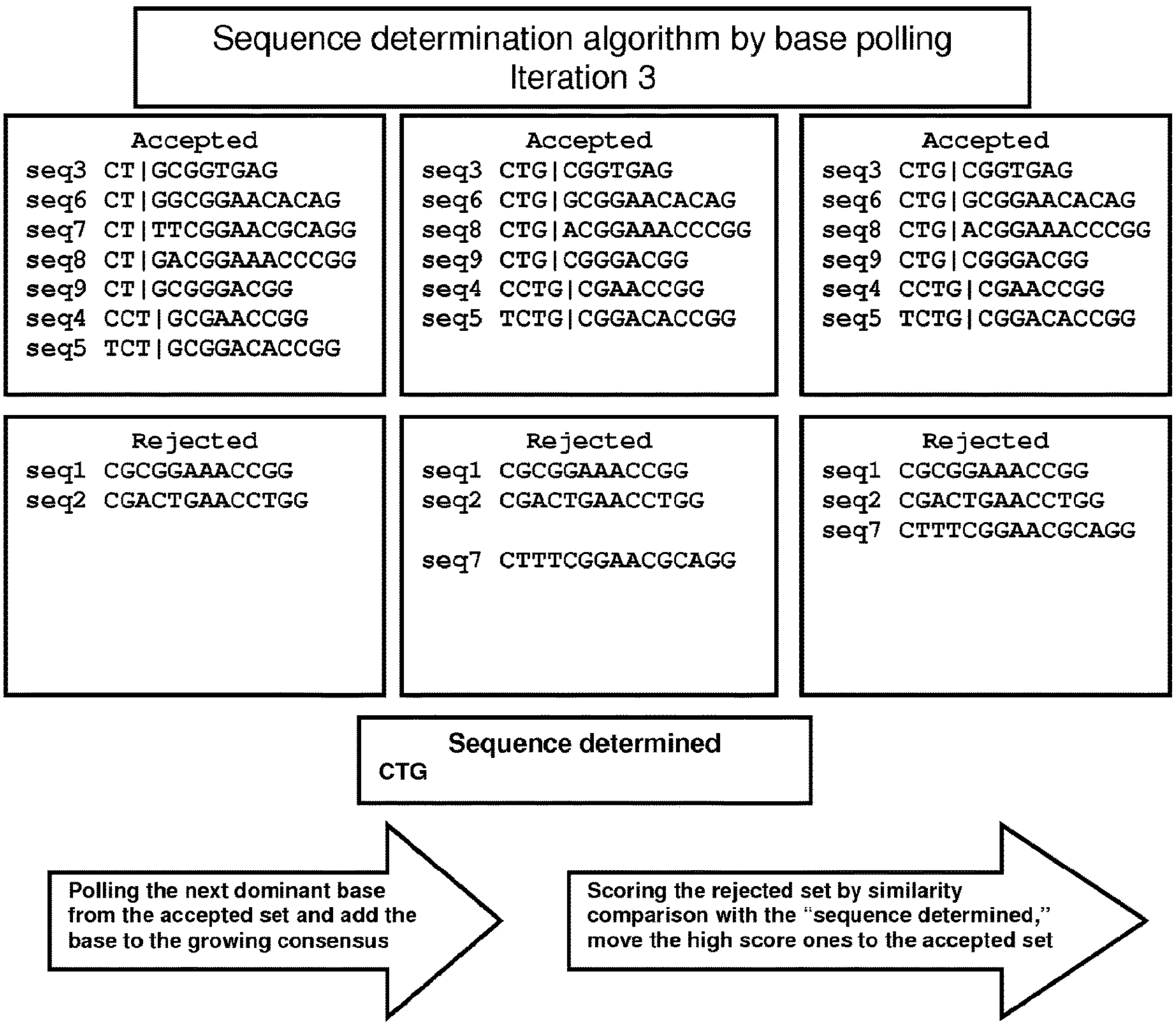
Figure 4D:
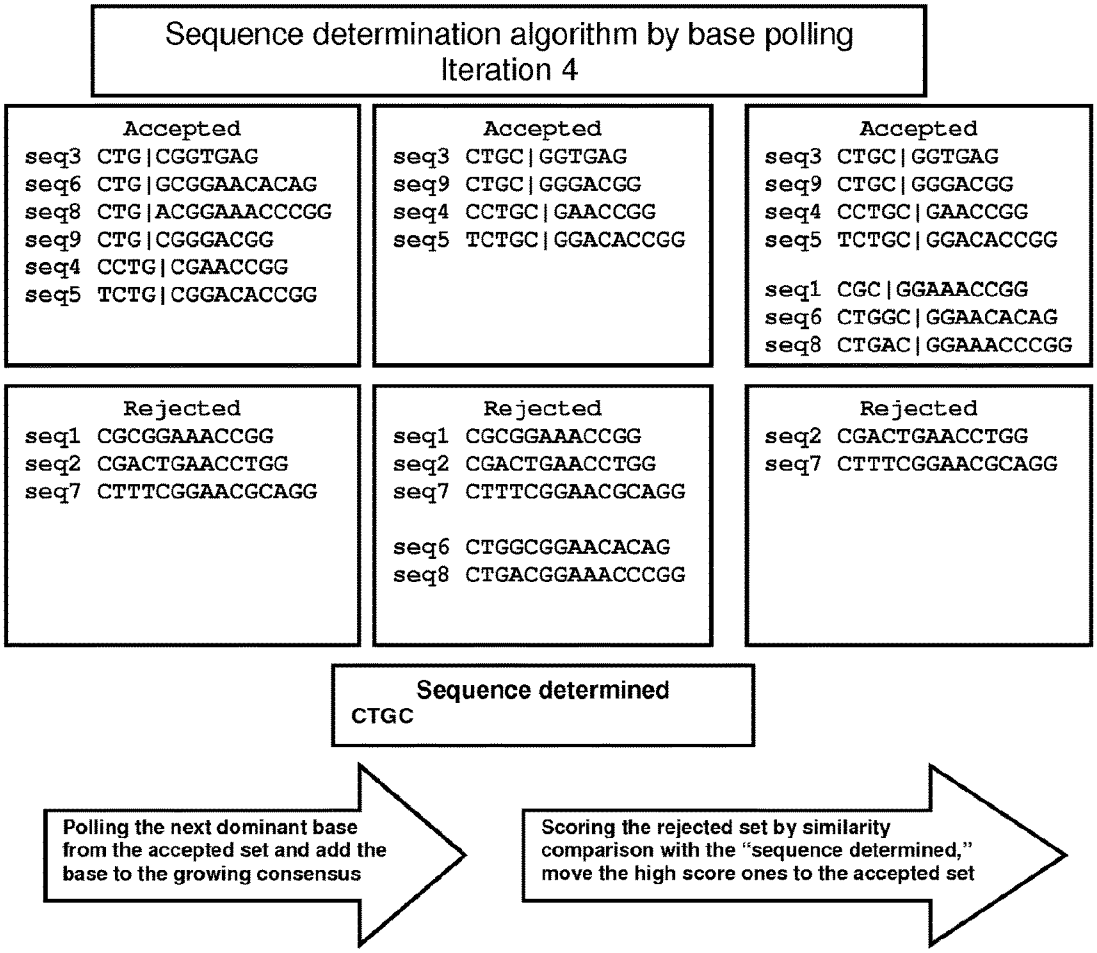

FIG. 2 is a block diagram showing a representative example of a configuration of a device for analyzing a nucleic acid target in which various aspects of the invention may be embodied. The invention can be implemented in hardware and/or software. For example, different aspects of the invention can be implemented in either client-side logic or server-side logic. The invention or components thereof can be embodied in a fixed media program component containing logic instructions and/or data that when loaded into an appropriately configured computing device cause that device to perform according to the invention. A fixed media containing logic instructions can be delivered to a viewer on a fixed media for physically loading into a viewer's computer or a fixed media containing logic instructions may reside on a remote server that a viewer accesses through a communication medium in order to download a program component.

FIG. 2 shows an information appliance (or digital device) that may be understood as a logical apparatus that can read information (e.g., instructions and/or data) from auxiliary memory 212, which may reside within the device or may be connected to the device via, e.g., a network port or external drive. Auxiliary memory 212 can reside on any type of memory storage device (e.g., a server or media such as a CD or floppy drive), and can optionally comprise multiple auxiliary memory devices, e.g., for separate storage of raw target sequences, determined sequences of the segments adjacent the adapter sequence, sequence variations information, and/or other information. The device can thereafter use that information to direct server or client logic to embody aspects of the invention.

One exemplary type of logical apparatus is a computer system as illustrated in FIG. 2, containing a CPU 201 for performing calculations, a display 202 for displaying an interface, a keyboard 203, and a pointing device 204, and further comprises a main memory 205 storing various programs and a storage device 212 that can store the raw target sequencing reads of a nucleic acid target 213 and the nascent sequence of the adjacent segment 214 and the consensus nucleobase 215. The device is not limited to a personal computer, but can be any information appliance for interacting with a remote data application, and can include such devices as, for example, a digitally enabled television, cell phone, or personal digital assistant. Information residing in the main memory 205 and the auxiliary memory 212 can be used to program such a system and can represent a disk-type optical or magnetic media, magnetic tape, solid state dynamic or static memory, or the like. For example, the invention may be embodied in whole or in part as software recorded on this fixed media. The various programs stored on the main memory can include a program to receive a population of raw target sequences of a nucleic acid target, a program 206 to receive a population of raw target sequencing reads of a nucleic acid target comprising an anchor segment and an adjacent segment, a program 207 to evaluate the accuracy of sequencing of the anchor segment in different raw target sequencing reads by comparing the anchor segment of a raw target sequencing read with the known sequence for the anchor segment, a program 208 to assign a subset of the raw target sequencing reads into an accepted class based on reaching at least a threshold level of accuracy of the sequencing of the anchor segment, a program 209 to poll nucleobases at a position equidistant to the anchor segment sequence in raw target sequencing reads in the accepted class to determine a consensus nucleobase, a program 210 to assign raw target sequencing reads having the consensus nucleobase determined in the prior polling step to remain in an accepted class and assigning raw target sequencing reads lacking the consensus nucleobase determined in the prior polling step to the rejected class, and a program 211 to reassign a raw target sequencing read from the rejected class to the accepted class by scoring similarity of the raw target sequencing read to the nascent sequence and reintroducing the raw target sequencing read if the sequence similarity reaches at least a threshold level of similarity. The lines connecting CPU 201, main memory 205, and auxiliary memory 212 can be any type of communication connection.

Raw target sequences and parameters required for the present methods can be specified by the display 202 (also referred to as a "screen"), the keyboard 203, and the pointing device 204. The CPU 201 can then execute a program stored in the main memory 205 and the sequence of a segment adjacent the adapter sequence including sequence variations, if present, can be determined by the present methods. The raw target sequencing reads of a nucleic acid target 213 can be read from the storage device 212. The output result of the nascent sequence of the adjacent segment 214 and the consensus nucleobase 215 can be stored into the storage devices 212. The progress of this processing can be displayed on the display 202. After completing this processing, the result of the processing can be also displayed on the display 202, saved to an additional storage device (e.g., ZIP disk, CD-R, DVD, floppy disk, flash memory card), or displayed and/or saved in hard copy (e.g., on paper). The result of the processing can be stored or displayed in whole or in part, as determined by the user.

VIII. Applications

The nucleic acid target or adjacent segment thereof can be derived from any of a number of sources, for example, viruses, prokaryotes, or eukaryotes (e.g., plants, fungi, and animals). These sources can include biological samples including patient and environmental samples (agricultural, water, soil), research samples, and industrial samples. A biological sample is a composition or mixture in which a nucleic acid molecule of interest may be present, including plant or animal materials, waste materials, materials for forensic analysis, environmental samples, and the like. A biological sample includes any tissue, cell, or extract derived from a living or dead organism which may contain a target nucleic acid, e.g., peripheral blood, bone marrow, plasma, serum, biopsy tissue including lymph nodes, respiratory tissue or exudates, gastrointestinal tissue, urine, feces, semen, or other body fluids. Samples of particular interest are patient tissue samples (including body fluids) from a human or an animal having or suspected of having a disease or condition, particularly infection by a virus. The nucleic acid target of interest in a patient sample can be from a pathogenic microorganism, such as a virus, bacteria or fungus, or can be endogenous to a patient, or both types of target can be of interest. Other samples of interest include industrial samples, such as for water testing, food testing, contamination control, and the like. Sample components may include nucleic acids to be sequenced and other nucleic acids, and other materials such as salts, acids, bases, detergents, proteins, carbohydrates, lipids and other organic or inorganic materials.

Nucleic acid targets or adjacent segments thereof can be isolated from samples using any of a variety of conventional procedures, for example target capture using a target-capture oligomer and a solid support (e.g., U.S. Pat. No. 6,110,678, EP 1778867, WO 2008/016988 & WO 2009/140374), the Applied Biosystems ABI Prism™ 6100 Nucleic Acid PrepStation, and the ABI Prism™ 6700 Automated Nucleic Acid Workstation, Boom et al., U.S. Pat. No. 5,234,809, or mirVana RNA isolation kit (Ambion). Nucleic acids can be cut or sheared prior to analysis, including the use of such procedures as mechanical force, sonication, restriction endonuclease cleavage, or other conventional methods to produce nucleic acid targets or adjacent segments from which nucleic acid targets can be formed.

The nucleic acid target or adjacent segment thereof can be DNA (genomic or cDNA), RNA (e.g., viral RNA, micro RNA, mRNA, cRNA, rRNA, hnRNA, transfer RNA, siRNA), and can comprise nucleic acid analogs or other nucleic acid mimics subjectable to sequence determination. The nucleic acid target or adjacent segment thereof can also be fragmented genomic DNA (gDNA), micro RNAs (miRNAs) or other short RNAs, or a short target nucleic acid is a short DNA molecule derived from a degraded source, such as can be found in for example forensics samples (see for example Butler, 2001, Forensic DNA Typing: Biology and Technology Behind STR Markers). The target can be methylated, non-methylated, or both. The target can be bisulfite-treated and have non-methylated cytosines converted to uracil.

A target nucleic acid can be synthetic or naturally occurring. Reference to a nucleic acid target can mean the nucleic acid target itself or s surrogates thereof, for example amplification products.

The present methods can be used in various applications, for example, de novo sequencing, DNA fingerprinting, polymorphism identification (e.g., SNPs) or other nucleic acid analysis. One application is determining the sequences of a heterogeneous population of variant nucleic acid molecules such as variant nucleic acid molecules of a same virus (e.g., HIV or HCV). Some examples of viruses that can be detected include HIV, hepatitis (A, B, or C), herpes virus (e.g., VZV, HSV-1, HAV-6, HSV-II, CMV, and Epstein Barr virus), adenovirus, XMRV, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, MLV-related Virus, papillomavirus, molluscum virus, poliovirus, rabies virus, JC virus and arboviral encephalitis virus.

Analysis of viral nucleic acids is particularly useful for analyzing drug resistance and the emergence of drug resistant viral strains presenting as minor variants in a virus population. Viruses mutate rapidly so that a patient is often infected with a heterogeneous population of viral nucleic acids, which changes over time. Some of the mutations differentiating species of the heterogeneous population may be associated with resistance to a drug that the patient has been treated with or may be treated with in the future. Deconvolution of the population to detect individual variants allows detection of drug resistant mutations and their change over time, thus allowing treatment regimes to be customized to take into account the drug resistance of strains infecting a particular patient. Because drug-resistant or other mutations may present as only a small proportion of viral nucleic acid molecules, sequencing of a large number of molecules in the viral nucleic population may be required to provide a high likelihood of identifying all drug resistant mutations or at least all, whose representation as a percentage of the total viral nucleic acid population exceeds a threshold.

The present methods can also be used for detecting SNP and somatic mutations. For example, the methods can be used to detect and characterize rare variants and identify unknown causative mutations in human diseases. The improved detection of rare sequence variants by the methods of the invention can also be applied to the discovery of novel somatic mutations, e.g., in cancers. Comprehensive genomic analysis of a variety of cancers can be performed, including acute myeloid leukemia, lung cancer, and melanoma. The present methods can be used to detect expression products of specific alleles, haplotype analysis and phasing of multiple SNPs within chromosomes, and copy number variation of DNA segments.

Human nucleic acids are useful for diagnosing diseases or susceptibility towards disease (e.g., cancer gene fusions, BR ACA-1 or BRAC-2, p53, CFTR, cytochromes P450), for genotyping (e.g., forensic identification, paternity testing, heterozygous carrier of a gene that acts when homozygous, HLA typing), determining drug efficacy on an individual (e.g., companion diagnostics) and other uses. Sequence variations information obtained from the present methods can be used to treat the subjects differentially. For example, samples from members of the patient population can be sequenced. The sequencing can provide information about a pathogenic microorganism infecting a patient (for example, type of organism and/or drug resistance). The sequencing can alternatively or additionally provide information about a patient gene associated with genetic disease, susceptibility or response to infection or response to treatment. Different members of the patient population can receive different treatment regimes (including no treatment) depending on the determined sequence for the sample from each member.

The present methods can also be used for epigenetics studies. For example, the methods can be used for detecting DNA methylation, such as aberrant methylation associate with various diseases such as cancers. The methods can also be used to select patients for demethylation therapies and to monitor the therapeutic response to demethylation agents.

The present methods can also be used for RNA analysis. Analysis of rRNA is particularly useful for detecting and/or typing pathogenic bacteria. Examples of such bacteria include chlamydia, rickettsial bacteria, mycobacteria, staphylococci, treptocci, pneumonococci, meningococci and conococci, klebsiella, proteus, serratia, pseudomonas, legionella, diphtheria, salmonella, bacilli, cholera, tetanus, botulism, anthrax, plague, leptospirosis, Lymes disease bacteria, streptococci, or neisseria. Ribosomal RNAs in these various organisms typically have conserved sequences and variant sequences that are unique to one or a few different organisms. A conserved sequence can be used to identify an rRNA and a variant sequence to identity an organism of which the variant sequence is characteristic. For example, U.S. Pat. Nos. 7,226,739 and 5,541,308 disclose conserved and variable rRNA sequences in a plurality of bacteria. Similarly, many diseases are associated with aberrant mRNA expression. The present methods can be used for transcriptome analysis (RNA-seq) such as small RNA mapping and transcriptome mapping.

Nucleic acids having sequences determined by present methods can be synthesized by conventional methods, including solid state synthesis and primer extension.

EXAMPLES

Example 1

Sequence Determination by Base-Polling

FIGS. 4A-D provides an illustrative example of sequence determination using the base-polling methods as described in the present invention. The example illustrates the sequence determination algorithm using an initial set of 9 raw target sequences (SEQ ID NOs:1-9). Raw target sequences that meet certain criteria (e.g., sequences being polled or reassigned) were placed into an "Accepted" class, and those that fail the same criteria were placed into a "Rejected" class. For illustration purposes, a total of four iterations of base-polling are provided for determining a sequence of four nucleotides.

Iteration 1

Raw target sequences 1-9 were chosen based on the quality of an adapter sequence (not shown), and aligned over the region of the adapter sequence. These sequences were placed into the accepted class and were used as the initial population of raw target sequences for base-polling. As illustrated in Iteration 1, the dominant nucleobase at the first nucleobase position is nucleotide C. The raw target sequences were accordingly polled and the first nucleobase of the sequence determined is C. Sequences 1-4, and 6-9, having C as the first base, remain in the accepted class. Sequence 5, having a T at the first base, were placed in the rejected class. The vertical bar in the accepted set indicates that the sequence segment before the bar is the sequence determined so far. The nucleobase after the vertical bar would be the next nucleobase for polling.

The sequences in the rejected class (e.g., sequence 5) were then compared with the determined sequence (e.g., a sequence comprising the first nucleobase C). In Iteration 1, sequence 5 was not reassigned into the accepted class because the first nucleobase of in sequence 5 is not the first nucleobase determined in the polling step, and there is not enough sequence similarity between the first nucleobase determined in the polling step and the first nucleobase of in sequence 5.

Iteration 2

The polling action at the second nucleobase generated the second polled base, T. Sequences 1, 2, and 4 were placed into the rejected class because the second nucleobase in these sequences is not T. Sequence 5 in the rejected class is carried over from the last iteration.

The sequences in the rejected class were then compared with the determined sequence CT. Both the first (C) and the second nucleobase (T) were found in sequences 4 and 5, even though they appear at the second and third positions by sequential numbering due to a single-base insertion. Therefore, sequence comparison found sequences 4 and 5 as good matches with the determined sequence CT. These two sequences were reassigned to the accepted set, leaving only sequences 1 and 2 in the rejected set.

Iteration 3

The polling action at the third nucleobase generated the third polled base, G. Sequence 7 was placed into the rejected class because the third nucleobase in sequence 7 is not G. All three sequences (1, 2, and 7) were not found to be similar to the determined sequence CTG. Sequences 1, 2, and 7 were not reassigned into the accepted class because there is not enough sequence similarity between the determined sequence CTG and these sequences.

Iteration 4

The polling action generated the fourth polled base, C. Sequences 6 and 8 were placed into the rejected class because the fourth nucleobase in these sequences is not C.

The sequences in the rejected class were then compared with the determined sequence CTGC. The fourth nucleobase C was found in these sequences, even though it appears at the third position of sequence 1 by sequential numbering due to a single-base deletion, and at the fifth positions of sequences 6 and 8 by sequential numbering due to a single-base insertion. These three sequences were reassigned to the accepted set because their overall sequences were highly similar to the consensus sequence.

Example 2

The Sample Sequence, Sequencing and the Primary Analysis Data

The sample sequenced was a region in the HCV 5' UTR of 164 base pair long that is listed below:

(SEQ ID NO: 10)
CTGCGGAACCGGTGAGTACACCGGAATTGCCAGGACGACCGGGTCCTTTC

GTGGATAAACCCGCTCAATGCCTGGAGATTTGGGCGTGCCCCCGCAAGAC

TGCTAGCCGAGTAGTGTTGGGTCGCGAAAGGCCTTGTGGTACTGCCTGAT

AGGGTGCTTGCGAG

The PacBio's standard sample preparation and SMRT™Bell preparation methods were used.

The sequencing was carried out on a PacBio RS sequencer using the following protocols.

TABLE 1

| Protocols used in sequencing and primary analyses | |
|---|---|
| Protocol | RS_CircCons_HCv1a3bUTR.1 |
| Collection protocol | Standard Scq 2-Sct v1 |
| Primary protocol | BasecallerV1 |

There are two videos of 45 minutes long. Data from the two videos are combined for the subsequent analyses.

TABLE 2

| Per video sequencing statistics | Video 1 | Video 2 |
|---|---|---|
| Reads of productivity = 0 | 2031 (2.7%) | 5033 (6.7%) |
| Reads of productivity = 1 | 44625 (59.38%) | 44098 (58.69%) |
| Reads of productivity > 1 | 28497 (37.92%) | 26008 (34.61%) |
| Mean Quality Score (productivity = 1) | 0.79 | 0.8 |
| Mean Read Length (productivity = 1) | 1398.67 | 1569.75 |
| Pass Filter | 59.73% | 58.85% |
| Active ZMWs | 97.30% | 93.30% |
| IPD | 0.22 | 0.26 |
| Poly. Speed | 2.21 | 2.05 |

TABLE 3

| The combined sequencing statistics are listed below. | |
|---|---|
| Total Bases | 391035620 |
| Total Reads | 150292 |
| Total Reads of productivity = 0 | 7064 |
| Total Reads of productivity = 1 | 88723 |
| Total Reads of productivity > 1 | 54505 |
| Total Active ZMWs | 143228 |
| Mean Quality Score (productivity = 1) | 0.79 |
| Mean Read Length (productivity = 1) | 1483.7 |

From the large number of files generated in PacBio's primary analysis, we only used the raw FastA file for all the ZMWs as our input.

On the PacBio platform, the sequenced molecule is in a SMRT™Bell format with a double stranded insert and a hairpin adapter at each ends. That produces a read of alternating forwarding and reversed strand of the insert interspersed with the adapter sequence.

The adapter sequence is (SEQ ID NO: 11)
ATCTCTCTCAACAACAACAACGGAGGAGGAGGAAAAGAGAGAGAT Example 3

The Workflow of the Polling Algorithm (1) Subread Extraction:

(a) Identify the adapter sequences and generate the subreads from each read.

(b) This process also offers some local sequencing quality information that can be used to further filter out low quality regions. That includes the spatial quality (the particular ZMW) and the temporal quality (the adjacent bases have a higher probability to be more similar than distant ones).

(c) Filter the subread set using certain criteria.

(2) Run Polling Algorithm:

(a) Assign all subreads with good adapter quality and sufficient length to the initial accepted set.

(b) A single base polling step: (i) Poll the most dominant base from the next base (the base immediately after the consensus matched segment of the subread in the accepted set, and initially it is the first base of the subread) of all the subreads in the accepted set. (ii) Assign the dominant base to be the next base in the growing consensus; (iii) Move the subreads with different bases to the rejected set (the newly rejected); (iv) Use the Overlap Matching pairwise-alignment algorithm that does not penalize overhanging ends to score the subreads in the rejected set with the consensus sequence. (v) Return the good matches to the accepted set (the returned).

(c) Repeat step b until a stop condition is met. The stop condition can be a pre-defined consensus length, the minimum size of the accepted set at that step, or a significant increase of the terminated subread at that step.

(3) After finishing one consensus, step 2 can be repeated with all the subreads in the rejected set. Iterate through to generate more consensuses until there is not enough subreads left.

Example 4

The Identification of the Adapters, Generation of Subreads and Quality Scores

From the primary data, the FastA files, all the adapter sequences in the raw sequence from each ZMW were identified using the algorithm described herein. We used the Overlap Matching alignment to align adapter sequence with the raw read. A score was computed from the alignment as $$\text{Score} = \frac{\text{Sum of the mismatches and indels}}{\text{The length of the matched portion of the adapter sequence}}$$

The score served as the quality score of the adapter. The alignment generated two unmatched fragments, occasionally one fragment from the read. The process was repeated recursively over the newly generated fragment until no more adapter matches could be found for the cutoff value 0.2 per base. In other words, for an alignment with a full-length adapter of 45 bases, the maximum allowed differences, mismatches and indels, was nine. The lower bound for the length of the matched portion of the adapter sequence was also set to be 24. Furthermore, the acceptable subreads were limited to the length between 60%-140% of the length of the amplicon that was 98-230, and there must be at least three subreads in a read.

124343 (83%) raw reads were removed due to short inserts (possibly adapter dimers) and poor quality adapters from further analyses. In the remaining 24836 reads, 179001 subreads were generated according to the adapter locations.

The matched sequences are normally not perfectly matched to the adapter sequence. For example, there can be some long regions without a good match indicating the quality was too poor for the adapter to be matched. Below is an example of removed low quality raw read. Notice the short length and long stretches like "AAAAAAAAAAAAAAAA (SEQ ID NO:12)".

-continued

```
TCGAGATAGAGGAATATGCGGTAGACGCGCTCGCGAAAGGACCTCAGCGG

CATTCTTTTCTTACACATACAGCTCTTTTTATTCTGCGCCACGCCGACAG

GTCTCCCCCAGATCCCTTCTTCAACCTAACCAGAGCTACAAGCTCTTGGC

GGGGAAGGCGGCGGCGACGCGCATCTGTAGATACGCGGCGGCGGTGTATA

GTTCTCCGACGCGGTACGCGGTCACTCCTGGCATGCTCGCAAGGGTGTAA

CTTAGATAGCTCCGGGTTTCCCCCGACTTCCCCAGGCCTGGCAGTAGGAG

TAGGCGTCCTTTGCGTTAGATTCTTCGTTTCTGCCTACAAACAAACCACA

AACACGCCAGATCGAGGAATGTGAGGAACCACCACGAGCCGCAAGAACTC

CATCCGCACGCGCCTACACCCGAGTACTATTTGGTTCGGGGCGTGGGTGA

CCCATTCCACCGGCCTGTGATCGACAGGACCCCTATAGGCATCTATACTC
```

```
>m110510_124258_sherri_c100084032555500001215005706031134_s1_p0/54
                                                    (SEQ ID NO: 13)
TGCAGCAGGGCGGCTGCTGAGAGTGATGGTCGCGACACTTGACTCGCAGGGTGA

CAAGAAAGCGCCTCTCCCCCATTGCCTCTTGTAAAATCCACGAGAACAAGACCGC

CATCCGACCCAAACAAAAACGACACTCAAAAAACAGCCACCAAAAAAACAAGC

ACAGAAGCAACCAAAAGAAACCACCAACCACACCCAGGAAAAAAAAAAACAAAA

AAAAACAAAAAAAAAACAAAAAAAAAACCACACCCACACATCATCTACAAACA

ACAAAAAAGACCGAAAAAAAAAAAAGATCGGACCCACCACCAATAACCTATAC

AACCACTTAAGAACGCGCAGCCACCCCCATCCACGAACAAAAAACACAACAGCC

AAAGAACACCAAAAAAAAAAAACAAAAAAAAAAAAAAAAAAAAAAAAAAAA

AAAAAAACAACAAAAAAAAAAGCTGGACGTGCTTGCCGAATGCGCGGTGGCGCTT
```

Five sequences with the matched portion to the adapter sequence indicated in lower case are listed below. The sequence names are their ZMW IDs. The matched sequences (lower case) are normally not perfectly matched to the adapter sequence. In addition, there are some long regions without a good match indicating the quality was too poor for the adapter to be matched. For example, in the first sequence (ZMW ID 7), the first two segments (spilt by the adapters) are quite long comparing to later ones. In this sequence, the subread should be about 164 base pair long.

```
> ZMW ID 7
                                        (SEQ ID NO: 14)
GGCCGCTCTGTCCAGCGATTCGCCGTGTTACCGTAATCGCTCAAGGCAGC

CCTCACGCTTCAGCGCGGTGTCTGTAGGATAGATCTTTCCGAGCGACAGA

GTGGACGGCCCTCGAAGAGGACTGGCCCGGCCTCGAGCCTGAGATCTGCG

TTAATGGCTCCCGATAGAGTCCGTCGGCTAGTGGTTGGAGCTCTCGCGCG

CTCCTAATAACTCGCTGCGCTTCCTCGCACICAGCAATCTACGCGTCCAC

TCTTCAGCTCAGACTAACAACCTCGCGAAGACGGAAGGAGAAGAGGCAGT

ATAGGGATGAGGTCATCGCGAAGGCCGCATCTATGCGCGAGGAAACCGGT

GAGTAACACCGCGGGTGCATCCGTGTATTGTATAGATCTCTGTGCCGAGC

ACCACAACAACGGAAGGGTCGCCGTTACGGGAAAAGCAGAAACGAGAACT

CGGATAAACCTTTATCTTGGCTCATTCGCACGGCTCTCGGGACCTGCCTC
```

-continued

```
TCGGAGCCTGGATATCGTACGGTGGCTTTGGCGGGGGTCGGACCGGCATA

TATCTCTCCATGCGTCATCTTAGAGCACAGGCAGTATTTCGGTACACAGA

AAAAGGACGAGACAGGACGAGTCGTCCTGTGCAATTCTGGCTCGTAGCTC

ACACCGGTCAGTCCGCAGACTGCTCTCTCAACCAAACACGAGACGCAGGT

AGGTTATGGCCAAAAGGAAGACCGAGGATTTCAAACTCTCTGGCCGGAAC

CGCGTGGGACAGTTCACCTTTCGGCGCACGCCAATCTGGCAGTGCTATTG

TCGCAGGCGCCCGGGGTTCATCTAAACGGATCGCTCGATATCTTAAATCC

TCGCGCTACAATGCCTTCCGGTGGAATGTAACTTCACCGTCCTTCTGGGG

CCAGATAGCCCCTCACCGCCAAGAACCAACCAACGAGGGAGGAGAAAGAA

CTGGACATTTACCCAGACCGTGTGGATGTGCATCCGCGACCGGCTTAGAT

GGTCCTCAAGGCTGAGCCTGGATTCCTGTGTCGGTGCTTAATCGCGCCGC

TCACATTCCTTCTCGATATCTGGAGACAACAGGACGGAGGTAGGAGGGAA

AAGAGCGAGGGAAGGTCCCTCGCCAAGCACCCTATCAGGCAGTACCACAG

GCCTTTCGCGACCCAACACTACTTCGGGCAAGACTTCTAACGCAGTACCT

TGAGTGACGGGGGCACGGTCCAAATCTCCCAGGCATTGAGCGGGTATCCA

CGAAAAAGGACCCGGTCGTCCTGGCAATTTCCGGTGTCTCACCGGTTCCG

CAGAatcttctctcaaacaacaacaacggaggaggaggaaatcggcagga
```

-continued gaAGACGTGCGTGTTTACACGGGTGTGTATTACACACCGGAATTGCCAGG
ACGGACCCTGGTCCTTGTCGGTGAGTGAATACCTTTCGGCGTCTACACAC
TCGTCACTCGAGCGAGAATCTAAACTAGGCAGAGGAAAGCGTAAGGAAGA
GCTCTCCAAAAGCACCTTCCTGCACTCCGCAACGAACGTGCTCGCTTGTT
GTCGCAGCTCCTGGGAACCACTCGCCGAAGGCCTTCGGTGGGTACTCTCT
TAGGTCAGGTGTGTCGCGGTTGGGAGGATCCCCTCTCAAACATCCACATT
TGAGGCGTTTTTTTAATTCACGGAAAAGGACCCGTCGGTTCCACCCAAAT
TCCGGGTGTACTCACCGGTCCCCAGATTCTTCTATTCAACAAAAAACGAG
AGGAACCAACGGAGGAGGAGGAAAAGAGAGAAGATCTCGCAAGCACCCTA
ATCAGAGCAAGGGATACGGCGAGGAACCTACTTGGCCTTTCCGCGGCCGA
ACCCGTGGAGTTAACCCGAATTCAACACCTAGGACCTGGCGGCTAAGCAG
TCTTGCGGGGCGCATCGCCAGATACTACCACGCGCCTTGCAACGGTTCTC
ACGAAGGAGGACCCGGTCGGTCCTGGGCAATTCCGGTCGTACTCACGCCG
AGTGCACGCGATACTCAATGCCGTCAACGCAACAAGCAGAACGGAGGCCA
GGGACCGCCGTTTTGAGTTAGATGAGACGAGGAATCTGCGGACCGGTGAG
TACACCGCATAATTCGTGGGCCATGGATCGACACGCTCAAGGCAAGCATC
TGATTCGTGGAATGGATAAAAAGAAAACCTTCTTCCGCAACGCTCAACTG
CCTGGCAGATTTGGCTGACGTTCAGGCCCCCAGCTCGCACAGACACTGCC
TTTTCGCGACGCGTACGTCTACCGAGTAGTCGTTGCGAGGCGTTCTTGGT
CGGCCGAAGGCCCCAAACTCCAGGGTTGCTCGGTTGGAAGCCTGTTTTAT
CCACCGAAGGAACCGCCGTCGGTCCTGCATGCTCCGTGATAGGCTCACGC
GCTTTCCTCGGGCATGTATGGATCTTTCTCCATACACAAAGCAACAAGCG
GAGAGGCAGGGAAAGAGAGAGCTAATCCCCGCAAGCACACCGCTATGCGG
CAGTTGACGCAAGAACAGAGAGACAGCGGGCCTTCTCGCTTGGACGCCAA
TTCACACTCAGCCTCGGCTAGCAAGTCTTGCGGGGCACGCCACCATCTCA
GGTGCTTGCATTTGAGCGGTCTGATTCCCACTGTATAGCGACCCGCGCTC
GTCCTGGGCAATTCCGTGTACCCCACCGGTTCCGCAGatactacaaccaa
caacaaacggaggaggcaggggaaaagagagagatGCTGAGGCGGAAGCC
GGTGAGTAGGCCACCGGAATTGCCAGGACGACGCCGGTCCTTTCGTGGAT
AAAACCCGCTCAATGCCTGAAGTTCTGGGCGTGCCCGCAAGACTGCTAGC
CGAGTTAGTGTTGTGGTCGCGAAATGGGAGGCCTGTGGTACTCGGCCTGA
TAGGGTGCTTGCGAGatctctctcaacaaacaacaacggaggagaggagg
aaagagacggcaggatCCGCAAGCACCCCTACTCAGGCCAGGTACGCACA
AGGCGCTGTTCGCCGAACGCCCCACACCTACTCCGGCTAGCAGTCTTGGC
GGGGGGCAGCGCCCAAATCTCCAGGCATTGAGCGGGTTTAATGCCACGAA
AGGACCGCCGGTCGTCCTGGCAATTCCGCGTGTACTCAGCCGGTTTCGCA
GatctctcatcaacaacaagcaacgcgaggaggaggaaaaggagatgatC
TGCGGACGCGTGAAGTACACCGGAATTGCCAGGACGACCGGTCCTTCCTC
GTGGATAAACGCCCGGCTTCCAAATGCGCTGGCCAGATTTGGCGGCGATG
GCCCGCAAGACTGCTAGCCGAGTTAGTGTTGGGTCGCGAAGGCCTTGTGG
TACTAGCCGTGAGTAGGGTGCTTGCCGAGatctctctcccaaacaaccaa -continued caacggaggaggaggaaaaagagagagatCCTCGGCAAGCACGCCTTATG
CAGGCCAGTACCACGAAGGCCTTCGCGACGGCGGCAACAACTACTCGGCT
ACAAAGACTCTTGGGCGGGGGGGCACGGCCAAATCTCCAGGCATTGAGCG
GGTTTATCCAACGAAAGGACGCGCGGTCGTCCTGGGCAATTCCGGTGTAG
CTCACGGTTTCCGCCAGAatctgctctcaacaagcaacacggaggaggga
ggaaaaggggggaAAGAGAGATCTGCGGAACCGGTGAGTACAGCCGGAA
TTGCCAGGACGCAACCGGGGGTCCTTTCGTGGATAAACCCGTCAATGCCT
GGAAGAATTTGGGGGCGTGCCCCCGCAAGACTCGCTAGGCCGAGTAGCTG
TTGGGCTGCGGGCGAAAGGCCTTGTGGTATCTCGCCTGATAGGCGTCGCC
TTGGCGAGatctctgctcagcccaacagacagacggaggcagagaggaaa
agagagagaATCCCTTCGCAAGCACGCCTATCAGGCCAGTACCACAAAGG
CCTTTCGCGAGCGCGTCAACACTAGCCTCGCTAAGCAGTCTTGGCGGGGG
GCAGCCAAATCTCGCAGGCATGAGGCGGGTTTATCCACGAAAGGACCCGG
TCGTCGCTGAGCAATTCCGGGTTAGCTCACCGGTTCCGCAGATCTCTCTC
AACAACAACAAGCCACCAAACGGAGGAGGAGGAAAGAGAGAGATCTGGCG
GAACGCGTGAGTACCG

> ZMW ID 8

(SEQ ID NO: 15)

GGTGGAGTACAAGCCACGGAATTGGCCACCGGGACGACGCACGCAGCACG
ACCCGGGTCCATTTCGTGGAATAACCCGCTCATGCCTGGAGATTTGGGCG
TGCCCCCCACCCCGCAAGACTGCTGCCGAGTAGTGTTGGTCGCCGAAAGC
GCCTTGTGGCTAAGCCTGCCGCCCTGATCAAGCACGGGTGCTTGCGAGAT
TCCTCTCACAACAACACCACGGATGAGGAGGCCAAAAGAGCAGAACTCTC
GCCAGCACCCTACTTCAAGGCAGTACCACCAAGGCCTTCCGCGACAGCCC
GCAACACCTACTCCGGCCTAGCCAGTCTTGAAGCGGGCGGGCAAGGCGCC
CAACGATCCTCCAGGGCATTGGCCGGGTTTTATCCCACGAAAGGACTCCG
GCGTGCCTGGCCCATTCCGTTGTACTCCACGCGGCTTCCGCAGCTCCTCT
CCTCCAAACAACCAACCAAAAACGAAGAGGAAGGAGGCAAAAGAGAGAGA
TCATGCGGAACCAAGGTGAGTACAAACCAGAGAATATAACACAAGGACAG
AACCAAAAAAGAAGAGAACCCATTCATAATCGATGATAACACAAACCGCT
CCACAGACATATAAAGAAGAACGCACGAACACGCGGCGCGTCGCCAAACG
CCAAGATAGCGAGTAAGCCAATAGATAAGAGAGCAAAACAAAGTCAGACA
GAGAAGACCATAATAGAGATAACAAAAAAAAAAAAAAAAAAACATAAAAG
CTGATAAGAGAAAAAAAAAGATGCTACAGAGAAAATATCATCTCCATCACA
CAACACAACACAGAGAGGAAGGAAAGGAAAAGAAGAAGAGAAGATACATG
CAGCACACTAAATCAAGAGAAAAAAACCAAAAAAAAGACAAGATAACAAA
AAAAAAAAAAAAAAAATACACACAAAAACACCAAACACACACAACAAACA
CACACCAAACAACACACAAACAAAAAAACAAACAAAAACACCAAAAAAAA
AGAAAAAAAAAAAAAAACAAAAAAACAAGACACAAACAAACAACAAAAAAC
CAAAACAAAAAAACAAAAAAAAACAAAGGCCTTTCGCCAAAAGAACCACA
ACAACTACAAAACAGACTAGAACAGATACCATATAAGCGGAGGAGCAAAA

-continued

GCACAAATACAAAAAATACCAGGCATATTGAAAGACAAAGGCGATAATAA
TAAACCACGAAAGGACCGGTCGTAAAACCTGGCAATTTCCGGCGTGTACT
CACCGTTCCGCAGatctctcctcacccaacacaaccggacggcaggaggc
aaaagagagagaGATCTGCGGAACCGCGCGTACACCGGAATTGCCAGCCG
GACGACCGGCGTCCTTTTCGTGGACTACACCCAGCTCAATCCGCCTCTGG
AGATTTGGGCGTGCCCCCCGCCAAGGCCGGACGGACCACTGCTAGCCGAG
TCAGTGTGATGGGGCGCCTCTGGCCCTCCGGCCCTTTGGCGGGGCGGGTT
TGCCTTCCGACCGTGGACGGGTCGCCGAAAGGCCGCCGTGTGCTCGGTCA
CTCCGCCGCCTGAAATAGGCGCTGGGCTTGGGGAGATCTTCTCCTCAACG
CGTCCGTCTGGCAATTCGGGTGGGCGCCCCGGGAGCGGGAGTGACGCGCA
GGAAAGAGAGAGCGCTCTGCATGCCGCCCCTATTCCCCAGGCGAGGGCGC
GACAGAGAAGGGCCGCTGTGTTCTGCTGCGGCCACGAGCATACTGCGGCC
TATGTAGTCGTGGCGGGGCGCCCAGATCTCCCAGGCATTGAGCGGGTTAT
CCACGAAGCTTATCTCCCGTCGTGGCCTTGGCCAACGCCCTTCCGGTGTA
CTCATCTGGGTGACGGCGATCTCGCGCCACGCCATTATAAGAGCGGCAGG
AGGGAGACGCGCCGAGAGCATGCTGCTGGAACCGCTGAGCGCGTTAACAG
CCGGAGTTTTCTGTGCCTAGGACGGGCTGTCGAGACCGTGGTCCTTTGTC
GTCGCTACATACCCGCTCAATGCCTTCGGAGATTGGTGGGCGTCTGCCGG
CCCGCGAAGGCACGGGCCTCTCCGGAGGTAAGCCGCTGTGGTGGGATTCG
CGAAAGGGCCTTGTGGTACTGGCCTGATAGCGCGTTTCCGCGCTTGCGCG
AGCGATCTCGTCTGCGAACATAACCAAAACGGGGAGGCGGCGGCGGAACA
GAGAGAGCAGAGTCCTGCGCGCCCCCCTCTCACCCGGTCGCGGCGCGGCG
ATCGATGCACCACAGGCGCCGCTTTCGCGGCCCAACATCTCACTACTGCG
CGCTAGCGCTCTGTGCGGCGGCTATACTGTCCAAGATGCGTCCTACCGGG
CAGGCCGCCGCCCGGCACCAGTCGCAGCATCCTGGAGCCCGCGGGTTTCA
GTCCACGGCAGCAGGTGGACGCCCCCGGGCTCGTGGCCCTCGCGACTCTC
CGGGTACGCACCCGGTTCCGGCAGGATCCCTCCATCAGCGCGGGCCGGGC
GCCGGCCACAACAGACGGGGCCGCGGCAGGAAGGGCCGGGACCCAAGAAG
AGAGAGATCTGCGGAACCGGTGAGTACACGGAATTGCCAGGACGACCGGG
TCCTTCGTGGATAAACGCTCGCTTCAATGCCTGGAGATTTTGGGCGTGCC
CCGAACTGCTAGCCGAGTAGTGTTGGGCTCGCGAAGCCCTTGTGGGTACT
CCGCCTGATAGGCGTGCCTTGCGAGatctctctcaacaacaagcaagcgg
aggaaggagggaaaagaaaggagatCGCTCCGGCAAGGCACCCTAATCAG
GCAGTACCACGAGAGGGCCTTTCGCGACCAAGCACTACTCGCGCTAGCAG
TCTTTGCGGGGGCACGCCAAATCCTCCGAGAGGCATCTGAGGGCGGGTTT
ATTCCAACGAAAGGACCCGGTCGTCGCCTGGCAATTCCCCGGTGTAGATC
ACGCGTTTCGCGGGCAGAATtctctctcacaacgacagcaacggagagag
caaaagaagagagatCGTGGCGGAACCGGTGAGTACACCCGGAATTGGCA
GGAACGACCGGTCCTTTCGTGGATAAACCCCGTCCAATGCCGTCGGAGAA
TTTGGGCGTGCCCGCAAGACTGCTTAGGCCGAGTAGTGTTGGTCGCCGAA
AGGCCTTGTTTGTGACTCGCCTGATAGGGTGCTTGCGGGGatgctctctc
caaacaaggcacacggaggagggaggcaaaagagagagatCTTCGCAAGC
CCGAGCCTATCAAGTGGCGCAGTACCCAACAAGGCTTCGGCGAGCCCACC
AACACTACTCGGGCTAGGCAGTCCTTGCGGGGCACGCCCAAATCCGGCAG
CATTGAGGCGGGTTTTTTTCTTTTTTAAAATCCAGGGTGCGGCTAAAGGA
CCCGGTCGTCCTGGCAATCCGTGTGTACCTCCCGGTCCGCAGatctgctc
caaacagacaacaacgggaggcagaggaaaagagagagatCTGCGGAACG
TCGTGTGAGTACGAACCGGAATTGCGCAGGACGACCTGGTCCCTTCTTCG
TGGATAGAACCCGCCTCAATGCACTGGAGATTTGGGGCGTGGCCCGCCGC
AAAGACTCCGGCTTAGCCGAGTAGATGGTTGGGTCGCGGATGCGCGAAAG
GCCTTGTGGTACCTCGCGTTTTTTTTTTTTATTTGTTCTTCCAA

> ZMW ID 19

(SEQ ID NO: 16)

CTTGTTGGGTCGCGCAACAGTGGGCCTGTGGTAACTGAGTTTTGTTCAGG
CCTGCATAGGTTGTGCTGCGAGTCTCTCTCGTGAAGCAGAGACAGACGGG
AGGCGGAGGAAAAGAGACGCCGGATATGATCCGAAGTTGTTATCTGCAGC
ACCTATCGGCAGTACCACAGTGCCTTTCGCGACCCATAGCACTACTCGGC
TAGCCAGTTCTGCGGGGGCACGCCAAATCTCAGGCATTGAGCGGGTTATC
CACGAAGACGGAACCCGGCGTCTGGCAATCGGTGCTACTCCGGTTCGCAG
CATCTTCTCACACAAACAACGGGGGAGACAGGAAAGAGAGAAAGATCAAT
GCGAACCGGTGAGTCACACCAGGATTCGCCAGGCGTACCGGGTCCCTTTC
GTGGATAAACCCAGCTCAATGCCTGGAGATTTTGGCGTGCCACCGCCAGA
CCTGCTCAGCCGAGTATGTTGGGTCGGAAAGGCCATTGTGGTACTAGCCT
GATAGGGGTGCTGTGCGAGATCTCTCTTCAACACACAACGCAGCGAGAAC
GGTTAAGGTAAACGGAGAGTTCTCGGAAGCACCCTATCGGGGGCAAGTCC
ACAGGAGGCCCTTTTCGCGACCCCATGACACTACTCGGGGGGGTCTTCGC
AGTCTTAGCCGGGGGCCGCCCAAATCTCTCAGGCATTTGGGCGGGTTTTT
TTTATCCACGAATGACCTGGCGGGCGGTCGTCTGGCAATGTCGGTGGTAC
TACACCGTTTCTCGCAGAGtctctctccaacatccacacaagcggaggag
gaggaaaagagaagagatCTGGCGGAGCCCGGTGGTACTCGGAATTGCCA
GGACGACCGGGGTCTTTCGTGATAAACCGCTCAATGCCTGGAAATTTGGG
CGTGCCCCCGCAAGACTGCTAGCCGAGTAGTGTTGGCGGTCGCGAATGGC
TTGTGTACTGGCCTGAATAGGGTTGCTTGCGGACGatcttcgtctcgaaa
caacaacaaacggaggagggagggaaaagagagagatCGTCGCAGCACCC
TATCAGCCGCAGCTACCACAAGCCTTTCGCGACGGGCAACGACTACTTTG
CGGGGAGCAGTCGTTGCGGGCCACGCCAATCTCGCCCAGGCATATTCGAG
GCGGGTTTTATCCCGCGGAGGGAGCCCGGTCGGTCTGGCAATTCGGTGTA
CTCGCACGGTTTCGCAGATCTCCTTCTCAAGCAACAGGGGGGGGGGAACA
GAGGGGGAGGGAGGCAGGACCAAGAGGAGGATGATCCTGCGGAAACCGGT
GAGTACAGCCGGGACATTGCCCAGGACGACCGCGCAGCCGGCCGCACCGC
CCCCCCGGTGCGGTCCTTCTCGTGGCCGCAGACGCCCCGCCCACCGGCGC
CCGTCAGTCCGCCCGTGCCGGAGAAGTATTGGGATGGGCGTGCCGCCCGC -continued

AAGACGTGCTCACGCCGAAGTAGTTGTGTTGGTGGCGCTGGAGGGTACTT

GTCGGCGAAAGGCGCTTTCGGGTAGCTGCCTGATAGGCCGTGCTTGGAGa tctcctctcaacaacaacaacggaggccacggaggcaaagagagctagat

GCTCGCAGCGACTATCCCGGCGCAAGGGCCTCATGTATGGAGCCGAACAC

TCAGCTCGGGCCGCTAAGGCGGCTCTGGCGGGGCCGACGCCTCGCGCGCG

CTCGAGGCTCGGGTTTATCCGCACCGACGGTACGCCGGTCGTCCTGGCAT

CGGTGTCACCTCACCGTTCCGCAGATCTCTCGCTGCCGACCAAGCAAGCC

AACCGGGGAGGCCGGGGAAAAGATGATCGAGATCGTGCGGACGCCTGGTG

ACGTACACCGGATTGCCAGGGACTACGACCTCCCTTTCCCGGGCTCCTCT

TCGTGGTATCAAGACCAGCAACGAAACCAGAGCGCTCACATGGCCTGGAC

GGGTTTGCGCGTGTCCGGCAAGACTGCTAGGCGCGAGATAGGTGTTGGGC

GTGCGCGAAGGAAACCTTAGTGGTACTAAGAAGCCTGATAGGGCGTGCCT

TAGCGAGATCTCTCGTGCACAGAGATTTTACTTCGCCCACCACAAACAAC

CGGAAGAAGGACGGCCAACAGAGACGAGATCCTCTCGCAAGCACCCCTAT

CAGGCAGTATAGCGCACAAGGCCTTTCGCGACCCAGCACTACTCGGGTCG

CTCGGCAGAGTCTTTGGGGCGCGCCAAATGTGCCAGGCATTGGACGGCGT

TATCCCCGAAAGGGACACCACGGTCGTCCTGCAGAAGCGTGCCGGTGTCA

CTGCACCGGTTCCGCGCAGTCTCtcttcgctcaacaagcagacaacggaa gcggaggaaaagagagtagatCTGGCACCGGGTGAGTACTACGCAATTTT

GCGCCAGGCAGCACGGGTCCCTTCGTGGATAGAACCCGGCTCATGCCTGG

GACTTTGGGCGTCGGCCCCCGCAAGACTGCTAGGCCCGAGTAGTGTTGGG

TCGCGAAAATGGCCTTGTGGTACTACTCGCCTTAGGAGTACGCTTGTGAG

ATCTtctctcgcaacaaaccacgacggaggcgggaggaaaagagagagaA

TCGGTCGCAAAGCCCCACTACATCAGGCAGTACCCTACAAGGGCCTTTCG

CGACTCCAACACTACTTCGGCTCTACGTCAGTCTTGCGCGGGGGCAGGGC

CGAATCTCAAGACATTGACGCGGGGTTTCTCCACGGAGGACGAGATCCGT

TCCTTGTGCAATTCCGTGTACTACAGCCGGTTTCGCAGATCCTCTCCCAA

CAAGCAACGCGAGGCGGCAACGGAACATGAGAGAGATCTGGCACCGTGAG

TGTACGCACGGAATTGCAGGCACGACGGGTCTTTCGTGGATAGTCAACCC

GCTATTGCTGGAGATTTGTGCGTTGCACCCAGCAATGACTGCTAGCGGCC

GACGTACGACGGGGTTAGGAAAAAGGGGTCGCGAAGGCCTTTGTGGTAAC

TACCGGCTGATAGGCGTGCTTGGCGAGATCCTGCTCTCCTCTCGCACTAA

CAACAGCGGGGAGGCCTGGAAGAGGAGAATTCTTCGCCAGCCGCCCGATC

CAGACAGCATAGTACTACACCCGGTGGCTTCTTCGCGCCCACACTACTCG

GCTCGACGATCTTGCGGGGCACGCCCAAAATCGTCCGCAGGGCCTTGAGG

CGGGTTATCCACGTAAAGGCCACGACCGGTCGTCCTGGCGACATATCTCG

GTGTACTCCGCGAGTTCCGCTCGATCTCTTCTCGATATCACCAACGTGAG

GCCAGGCGGCAAAAAGAGAGAGTCTGCGAACGCGGCTGACGATACACCGG

ATTGCAGGACGACCGGGTCTTTATCCGTGGATAGACACCCGCCATGCCTG

GAGATTTGGCGCGTTGCCCGCAAGACTGCTAGCGAGTAGCTCGTTGGGCG

TCGGCCGAACGGCCTTGTGGTACTGGCTGATAAGGGGTGCTTGCGACGat

-continued ctcttccttcacaacaacaaccggaggaggaggaaaagagaggaAGGATC

TCGCAGCACCCCTACCTCAGGCAAGTACCACAAGGCTTTCGGACCCAACC

TACCTCGCTAGCAGGTCTTGCGGGGGCCACGCCAAATCTCCCCAGGCATT

GAGCAGGCGTTTATCCAACCGACAAGCCTCGCCCGGGCGGCGCCCGCCCG

CCCAGCCTGTCTCCTCTTCTCTTTCTCTTTCTTCTGGCGCTCGCCTCCTC

GTCGGTCCCCGGCGTTCCGGCCCGGCGTCCCCTCATGTCTCGCCGCGCGC

CCCCCTCCTCCTTTGCCTGCCCGCTCTCGCCCCCTGTTTCCTTCCACGCT

GGCTCGCGCGTGCGCTGTCACTCCCGCCCTCCCGGTCCGCAGA

> ZMW ID 21

(SEQ ID NO: 17)

CCCGCAGACTGCTAGCCGAGTAGTGTTGGGTCGCGAAGGGCCTTGTGGTA

CTCTCCGCCTGATGGGGTGGCTTGCGAGAACGCCCCCGCGCCAAAAAAAC

ATGCTCTCCTCCACAACAACAACGGAGGAGGGTGCTGCTTTAGGAAAAGA

GAGAGATTCGCAGCCCCACGCAGCCCTAGTCCCGCAGCAGCGTACCCACC

CACCCCAGCGCCTGTTCGCCGACCGCCACACTACCGGCTTAGCAAGTCTT

GCGGGGCACGCCCAAATCTCCCGGGCATTGAGCGCGTTTTACTCCACCGG

AAAGACCAGACCTCGGGCGTCTGGGCATTCGGTTGCTAACTGCACCGGTT

TTCCCCGCAGatcttttctcacacaaccacggggcggaggaaaagagaga gatCTGGCGGTGAACCGGGTTGGTACACCCGGAATTGGCCCAGGGACGAC

CCCGGGTCCCTTTCTCGTGGATAGAACCCGCCTCCATGCCTGGAGATTTG

GGCGTCCCCCCGCCAGACTGCTAGCCGAGGTAGCTGTTTGGGCTCCGCGA

AGGGCTTTGTGGTACTGCTGAATAGGGTGCTTGCGAGATCTCCGtctcca acaacaacaacaacggaggaggaggaaacatgaagagagatCCTTCGCAA

GCACCCCTAGTCCAGCGGCAGTACCAACAAGGCCTTTCGGCGACCCAACA

CGTTACTCGGCTAGCAGTCCTTGCGGGGGCACGCCCAAATCTCCCAGGCA

TTTGAGCCGACGCGCGTTTTTTTATGCCCACCGAAAGGGGACCCGGCCG

TCCTGTGCCAAATTCCCGGTGTACTGCCACCCGGTTCCGCAGATtcgtct ctccaacaacaacaacggaggaggaagggaaaagagagagatCTGCGGAC

CCGGTGAAGCTCACCGGAAATTGCCAAAAGGAGACCCGGGTCCTTTTTTC

GTTTGGATAAACTCCGCTCATGCCTGGAGATTTGGGCGCGTGCCCGCCCC

GCAAGACTGCTTAACTAGCCGAGTAGTGTTGGGTCGGCGAAAGGCCTTGG

TGGTAACTGCCTGATAGGGTGGGCGTTGGCGAGatctccatcaacaacaa caacgggagggaggaggaaaagagagagatCTCGCAAGCAAGCCCTATCA

GGCGTACCACACGGCCTTTTCGCGGAACCAAACACCTACTCCGGCTAGCA

AGCTTCCTGCGGGGGGCCACGGCCAATCTCCAGCCATTTGAGCGGGTTTT

TATCACACGAAGACCCGGCCGGTCTGGCAATCTCCGGTGTAGCTGCAACG

CGGTTCCGCAGatctcttgctcaacaacaacaacggaggaggcaaaggaa acagagagagatCTGCGGAACCGGTGAGTCACCGGAAATTTGCCCAGGAC

GACACGGGTCCTTTCGTGGATAACACCGCCAATGCCGTGGGAGATTTGGG

CGTGCCCCGCAAGAAACTCTGCCTAGCCGAGTACGTGTTTGGGTCCGGCG

AAAGGGCCTTGTGGTAATTCGCCTGATAGGGTGCTTGGCGGAGCatctct

-continued ctcaacaacggaaaaacggaggaggagggaaagagaggagatCCTCGCAA
AGCACCCTATCAGGCAGTGACAACAAGGCCTTTCGCGACCTAACACTACT
TCGGCGTTAGCATCTTTGCCGGGGGCAGGCCCAAATCTCATACAGGCATT
GGAGGCGCGGGTTTTATCCACCCGAAAAGACCCGCCGGTCTGGCGGGGCA
ATTCCGGTGGTACTTCAACGGTTTCCCGCCAAGAatttctcctcaaacaa
caacaacggggaggaggaaaagagagagatCC

> ZMW ID 25

(SEQ ID NO: 18)

CCCGTCTGAGCCCGGCGTTCCTATCCACGACCCCGGACCCCCGCGCCTCG
TCCCCTGCGCCGCAACTGTCCGGCCCTGCTCAACCCTCCGGTTCCGGCCA
GatctcctctaacaacaccaacggaaggaggaggaaaagagatgacgatC
TGCGGAACCGGTTGAGTACACCGGAATTGCCAGGACGACCGGGTCCTTTC
GTGGATAAACCCGCTCATGCCCGGAGAATTTGGGCGGTGCCCACGCAAGA
CCTCGCTCCGATTCAGCGATAGTCGTTGGGTCGCGAAAGGCCTTTGTGGT
ACTGCCTGATAAGGGTGCCTGCGAGATCTTCTCAACCAGCACAAGCGGCA
GGGAGGCGAGGAAAAGAGAGAAGATCTCGCACGCACCCCCGCCTATCAGC
GCAGTACCACAAGGCCTTTCGCGACCAACAACCTACTCGGCCCGCCTAGC
AGTCTTGCCGGGGGCACGCAAATCTCCAGGCATGAGCGGGTTATCCACCG
ACAGGACCGTCGCGTCGTCCTGGCAATTCCGGTGTACTGCACAAGGCTTC
CGCAGGCATCTCTCTCAACCCACACCGCAACGAGGAGGAGGAAATACAGA
GAGAGATCTGCGGAACCGGTGAGTACACCCGGATTGCAGGACACCGGGTC
CTTTCCGTGGATAACCCGTCGAATGCCCCGGAGACTTTGGGCGTGCCACG
CAAGATGCTCAGCCCGAGTAGTGTCTGGGTCGCGAAAGGCCTTGTGTACT
GCTGATAGGGTGCTTGCGAAGatctctctcaacaacaacaacggggagga
ggaaagagatgagatCTCGCAAGCAACCCCTATCAGGGCAGGTCACCACA
AGGGCCTCGTATCGCGACCCACACTACTCGGCCTAGCAGTCTTGCGGGGG
GGCACGCCGAAATCTCCAGGCATGTGAGCGGGTTTATCCCGCGAAAGGGC
CACGCGGCTCGTGCTGGCCGAATTCCGGTGTACACTCACCGGTTCCGCAG
ATCTCTTCTCCATCAGCACAACAACGAGGAGGAGGAAAAGAGCAGGAAGA
TCTGCGGAACCGGTGACCGTACACCGGATTGCCAGGACGACCAGGGTCCT
TCTCGTGGATATACCCGCTCAATGCCCTCGGAGATTTTTGGCCGTGCCCA
CGCAAGAATGCTAGCCGAGTATTGTTTGGGTTCGCGAAAGGCCTTGTGGT
CTGCGCCTGATAGGGTGCTTGCGAGtctctctcaacaacaacaccggagg
gaggacaagagagagagatCTCGCAAGCACCCTATGCCAGGGCCGTACCCCC
ACGGGGCGGGGCCTGGTTCGCGAGCCCAAACACCTACTCGGCTAGGCAGG
TCTTGCGGGGCACGCCCAAATCTCCAGGCATTGAGCGGGTTTATCACGAC
AGGACCCGCGTCGTCCTGGCATTCCGTGTGTACTCCAACCGGTTTCCCGC
AGatctatctcaacaacacaacggaggaaggtaaggaacagaggagagat
CTGAGGAGAAACGCCGCGTGGAGTACACGGATTGCCAGGACGGACCGGGT
CCTTTCGTGGATAAACCCGCTCAAATCCGGAGATTTGGGGCGTCGGCCCA
CCGCAGACTGCTAGCCGAGTACTGTTGGGTCGCGAAAGGCCTTGTGGGTA
CTGCCTATAGGGTGGCTGCCGAGatcttctctcaacacacacggagggca
gcgaggaaaagagagaCAGCTCTCGGAACGCCCCTATTCAGGGGCCAAGG
CCTTCCCGCTCGGCGACCCCACACTACTCGGATAGCCAGTCTTGCGGGGC
CACGCCCAAAATCTCCAGCCATTCGGAGCGGGTTTAATCCACGAAAGGAC
CCCGGTCGTCCTGCAATTCCGGTGTACTCACCGGTTCCGCAGATtctctc
tcaacaacaacaaccgagaggagggacggaaaagagagacgatCTGCGGA
ACCGGTGAGGCTACAGCCCGGAATTGCCAGGACGACCGGTCCTTCTCGTG
ATACAACCCGCCTCAATGCCGAAGAATTTGGGCGTTGCCCACGCAACGAC
TCGCTAGCCCGACGTAGTGTTGGGTCCGACGAAAGGCTTGTTTGCGTACT
GCTGTAGGGTGCTTTGCGAGATCTTcgctctcacaacaacaacggaggca
ggaagggaaaagagagagTCCTCGCAAGCACCGCCTAGTCAGGCAGTACC
ACAAGGCCTTTCCGCGACCGCAACAACTATCGGGCCGCTAGCAGTCTTGC
GGGGCACGCCCAATTCTCCAGGCTTGAGCGGGTTTTATCACCGAAGGACC
CGGTCGTCCTGGCAATTCCGGTTGTACGCTCACCGGTCCGCAGatctcct
ctcacacacacaacggaggaggaggaaagacgagagatCTGCGGAACCGG
GGTGAGTACACGGACATTGCCAGGACGCCGGGTTCTTTCGTGGATAAACC
GCTCAATGCCCGGAGATTTGGGCGTGCCCCACGCAATGACTGCTAGCCAG
TAGTGTTGGGCTCGCGAAAGGCCCTTGTGGGTACTGCGCCTGATAAGGGT
GCTTGCGAGatcttctcaacaacacaacgagaggagggaaaagagagaga
tCTCGCAAGCACCTATCAGGCGTACACAACGGCCTTCAATCAGAAAAAAG
ACCCAGACACTACTCGGCTAGACAGTCTTGCGGGGGCACGCCCCAAATCT
CAGGCATTGAACGGGTTTATCCACGAAAGGACCGCGGTCGTCCCCTGGCA
ATCTCGGTGTACTCCAGCGGTTTCCGCACAGATCCTCTCCTCCCACACGC
CcaacaacaacaacgcgaggaggaggcgaaaagacgagagatTCTGCGAA
CCGGTGAGTACACCGGAATTGCCAGGCCGGACCGGGTCCTTTCGTGGCTA
AACCCCGCTCAATGCCGCGGAGATTTGGGGCGTTCGCCACGCACGACTCG
CTAGCCGAGTAGTGTTGGGCTCCGCCCCGGAAAGGCCTTGGTGGCTACTG
CCTGATAGGGTGCTGCGAGatctctctcaagcaacaacaacggaggacgg
gaggaaaagacgacgacgcatCTCGCCACGCAGCCCTAATCAGGGGGCAG
TCACCGGGCACAAGGCGCTTTCGCGCACCCCATCACACTCAATGCGCGCC
TGGAGCAGTCCACCCGCTTGCCGGGAGGCCTCGGCACGGCCAAACGCGCC
AGATCTCGCACGGCATCCGTGGAGCCGCGGTTTACTCCCACGAAGAGGAT
CCCCGGTCGTGCGCTGGGCAATTCCGGTGTACCTCGCTTGCAGCCCGGCT
TCCGCATGATCTCCTCTCCAATCAACAACAACGGAGGAGGGAGGAAAAAA
CGAGGAGCAGATCCGTGGCGGACAACGCCGGTGAGGTACAACCCGGGAAA
TTCCGCCGAAGCAAACGGCGACCGGTCTCTTCCCCACGCAACACCACGCG
ATCAATCCAAACAAAAAAAAAAAAAAAAAAAAAAAAAACGTGGAAACCAAGA
GGAACACCACCCGCCCCCCGGGCACCC Example 5

Run the Polling Algorithm to Generate One Consensus

From the initial 179001 sequences in the accepted set, the first poll produced the first base of the consensus that is C with about ⅔ of the bases (See Table 4). The distribution of the base were 114994, 26000, 19299, 18708 for C, A, G, T respectively. For the first two iterations, we skipped the scoring sequences from the rejected set simply because there is no chance for those sequences to be scored high and returned to the accepted set. The Overlap Matching alignment was used for the scoring starting at the third step. The cutoff was 0.25 per base. A sequence with a matching score less than the cutoff would be returned to the accepted set.

We started at the third step with 82079 in the accepted set and 96922 in the rejected set and the consensus sequence is CT. The polling found G is the next dominant base and rejected 44131 sequences. Then the Overlap Matching alignment of the 141035 sequences (96922 plus 44131) to the consensus sequence CTG and found 14915 sequences with good matches, and returned them to the accepted set. Therefore, at the end of the third step, we have consensus CTG, 52863 in the accepted set and 126138 in the rejected set. The data points mentioned in the paragraph are highlighted in Table 4.

To illustrate the process furthermore, nine subreads at step 5 are listed below. We started with the consensus CTGC. The next bases to be polled are lined up. It is obvious that G was the dominant base and should be incorporated in the consensus. Sequence 4 should be moved to the rejected set. Notice that sequences 3, 4, and 5 have an extra G at the fourth position (can be considered as an insertion there). They must have been rejected initially in step 4 and then returned hack into the accepted set because they had high enough matching score in the pairwise-alignment analysis.

1
CTGC G (SEQ ID NO: 19)

2
CTGC G (SEQ ID NO: 19)

3
CTGGC G (SEQ ID NO: 20)

4
CTGGC A (SEQ ID NO: 21)

5
CTGGC G (SEQ ID NO: 20)

6
CTGC G (SEQ ID NO: 19)

7
CTGC G (SEQ ID NO: 19)

8
CTGC G (SEQ ID NO: 19)

9
CTGC G (SEQ ID NO: 19)

The consensus generation was set to be terminated if the number of early-terminated subreads more than doubled from one step to the next. This round of consensus generation stopped when the terminated subreads jumped from 2934 to 27713, a more than nine fold increase. The generated consensus sequence exactly matched the amplicon sequence, representing 44490 sequences.

TABLE 4

The statistics at each step of the polling process for the first consensus

| Step | SEQ ID NO: | Consensus generated (omitted after 30) | Accepted size | Rejected Size | Newly rejected | Newly returned |
|---|---|---|---|---|---|---|
| 1 | — | C | 179001 | 0 | 64007 | 0 |
| 2 | — | CT | 114994 | 64007 | 32915 | 0 |
| 3 | — | CTG | 82079 | 96922 | 44131 | 14915 |
| 4 | 22 | CTGC | 52863 | 126138 | 9965 | 12798 |
| 5 | 19 | CTGCG | 55696 | 123305 | 11862 | 53929 |
| 6 | 23 | CTGCGG | 97763 | 81238 | 49577 | 17871 |
| 7 | 24 | CTGCGGA | 66057 | 112944 | 17367 | 10949 |
| 8 | 25 | CTGCGGAA | 59639 | 119362 | 11308 | 13704 |
| 9 | 26 | CTGCGGAAC | 62035 | 116966 | 21156 | 12550 |
| 10 | 27 | CTGCGGAACC | 53429 | 125572 | 11945 | 34538 |
| 11 | 28 | CTGCGGAACCG | 76022 | 102979 | 34638 | 23424 |
| 12 | 29 | CTGCGGAACCGG | 64808 | 114193 | 20730 | 13214 |
| 13 | 30 | CTGCGGAACCGGT | 57292 | 121709 | 14288 | 12986 |

TABLE 4-continued

| The statistics at each step of the polling process for the first consensus | | | | | | |
|---|---|---|---|---|---|---|
| Step | SEQ ID NO: | Consensus generated (omitted after 30) | Accepted size | Rejected Size | Newly rejected | Newly returned |
| 14 | 31 | CTGCGGAACCGGTG | 55990 | 123011 | 9236 | 11890 |
| 15 | 32 | CTGCGGAACCGGTGA | 58644 | 120357 | 12587 | 14177 |
| 16 | 33 | CTGCGGAACCGGTGAG | 60234 | 118767 | 14136 | 15506 |
| 17 | 34 | CTGCGGAACCGGTGA GT | 61604 | 117397 | 17413 | 11500 |
| 18 | 35 | CTGCGGAACCGGTGA GTA | 55691 | 123310 | 10119 | 13459 |
| 19 | 36 | CTGCGGAACCGGTGA GTAC | 59031 | 119970 | 15801 | 16710 |
| 20 | 37 | CTGCGGAACCGGTGA GTACA | 59940 | 119061 | 16114 | 33422 |
| 21 | 38 | CTGCGGAACCGGTGA GTACAC | 77248 | 101753 | 34352 | 14127 |
| 22 | 39 | CTGCGGAACCGGTGA GTACACC | 57023 | 121978 | 15523 | 16687 |
| 23 | 40 | CTGCGGAACCGGTGA GTACACCG | 58187 | 120814 | 26073 | 16440 |
| 24 | 41 | CTGCGGAACCGGTGA GTACACCGG | 48554 | 130447 | 13237 | 13830 |
| 25 | 42 | CTGCGGAACCGGTGA GTACACCGGA | 49147 | 129854 | 11748 | 14166 |
| 26 | 43 | CTGCGGAACCGGTGA GTACACCGGAA | 51565 | 127436 | 8564 | 17263 |
| 27 | 44 | CTGCGGAACCGGTGA GTACACCGGAAT | 60264 | 118737 | 21062 | 10416 |
| 28 | 45 | CTGCGGAACCGGTGA GTACACCGGAATT | 49618 | 129383 | 8836 | 10108 |
| 29 | 46 | CTGCGGAACCGGTGA GTACACCGGAATTG | 50890 | 128111 | 11249 | 13467 |
| 30 | 47 | CTGCGGAACCGGTGA GTACACCGGAATTGC | 53108 | 125893 | 9505 | 21651 |
| 31 | | | 65254 | 113747 | 18871 | 20863 |
| 32 | | | 67246 | 111755 | 22646 | 19167 |
| 33 | | | 63767 | 115234 | 18193 | 15587 |
| 34 | | | 61161 | 117840 | 13398 | 17384 |
| 35 | | | 65147 | 113854 | 20073 | 8978 |
| 36 | | | 54052 | 124949 | 11515 | 14100 |
| 37 | | | 56637 | 122364 | 17025 | 16122 |
| 38 | | | 55734 | 123267 | 16778 | 14578 |
| 39 | | | 53534 | 125467 | 13981 | 12212 |
| 40 | | | 51765 | 127236 | 11483 | 26561 |
| 41 | | | 66843 | 112158 | 35648 | 12012 |
| 42 | | | 43207 | 135794 | 6848 | 12433 |
| 43 | | | 48792 | 130209 | 12659 | 16392 |

TABLE 4-continued

The statistics at each step of the polling process for the first consensus

| Step | SEQ ID NO: | Consensus generated (omitted after 30) | Accepted size | Rejected Size | Newly rejected | Newly returned |
|---|---|---|---|---|---|---|
| 44 | | | 52527 | 126474 | 15338 | 6996 |
| 45 | | | 44190 | 134811 | 8778 | 15930 |
| 46 | | | 51347 | 127654 | 12923 | 17754 |
| 47 | | | 56186 | 122815 | 14998 | 17921 |
| 48 | | | 59124 | 119877 | 16010 | 14241 |
| 49 | | | 57376 | 121625 | 10879 | 11652 |
| 50 | | | 58174 | 120827 | 13281 | 9551 |
| 51 | | | 54473 | 124528 | 14658 | 13924 |
| 52 | | | 53772 | 125229 | 14505 | 13995 |
| 53 | | | 53299 | 125702 | 9755 | 9569 |
| 54 | | | 53167 | 125834 | 8883 | 9895 |
| 55 | | | 54236 | 124765 | 12433 | 7752 |
| 56 | | | 49618 | 129383 | 9334 | 19022 |
| 57 | | | 59375 | 119626 | 15454 | 10353 |
| 58 | | | 54349 | 124652 | 9130 | 14081 |
| 59 | | | 59385 | 119616 | 14028 | 6916 |
| 60 | | | 52362 | 126639 | 13466 | 10914 |
| 61 | | | 49905 | 129096 | 7646 | 18302 |
| 62 | | | 60669 | 118332 | 18664 | 11928 |
| 63 | | | 54055 | 124946 | 20405 | 14373 |
| 64 | | | 48154 | 130847 | 12198 | 17810 |
| 65 | | | 53920 | 125081 | 18203 | 13074 |
| 66 | | | 48957 | 130044 | 8908 | 8615 |
| 67 | | | 48836 | 130165 | 8893 | 18242 |
| 68 | | | 58362 | 120639 | 16139 | 17273 |
| 69 | | | 59678 | 119323 | 24104 | 9033 |
| 70 | | | 44794 | 134207 | 7642 | 13128 |
| 71 | | | 50470 | 128531 | 9146 | 19209 |
| 72 | | | 60729 | 118272 | 14745 | 13502 |
| 73 | | | 59694 | 119307 | 19389 | 13108 |
| 74 | | | 53637 | 125364 | 13656 | 9637 |
| 75 | | | 49854 | 129147 | 6114 | 16206 |
| 76 | | | 60196 | 118805 | 15221 | 9720 |
| 77 | | | 54953 | 124048 | 11659 | 15499 |
| 78 | | | 59056 | 119945 | 16262 | 9596 |
| 79 | | | 52660 | 126341 | 12704 | 10582 |

TABLE 4-continued

The statistics at each step of the polling process for the first consensus

| Step | SEQ ID NO: | Consensus generated (omitted after 30) | Accepted size | Rejected Size | Newly rejected | Newly returned |
|---|---|---|---|---|---|---|
| 80 | | | 50813 | 128188 | 6209 | 13179 |
| 81 | | | 58065 | 120936 | 13201 | 10722 |
| 82 | | | 55882 | 123119 | 13667 | 4597 |
| 83 | | | 47116 | 131885 | 4400 | 10757 |
| 84 | | | 53786 | 125215 | 12359 | 10225 |
| 85 | | | 51981 | 127020 | 11935 | 7755 |
| 86 | | | 48141 | 130860 | 14030 | 20101 |
| 87 | | | 54561 | 124440 | 16701 | 12618 |
| 88 | | | 50845 | 128156 | 12717 | 9321 |
| 89 | | | 47830 | 131171 | 9451 | 11740 |
| 90 | | | 50505 | 128496 | 5981 | 19800 |
| 91 | | | 64728 | 114273 | 16319 | 12222 |
| 92 | | | 61067 | 117934 | 16241 | 6365 |
| 93 | | | 51659 | 127342 | 21032 | 5777 |
| 94 | | | 36893 | 142108 | 14631 | 9883 |
| 95 | | | 32651 | 146350 | 8044 | 23761 |
| 96 | | | 48925 | 130076 | 11346 | 15219 |
| 97 | | | 53376 | 125625 | 11708 | 22066 |
| 98 | | | 64327 | 114674 | 21640 | 12338 |
| 99 | | | 55638 | 123363 | 16424 | 10164 |
| 100 | | | 50030 | 128971 | 11730 | 13787 |
| 101 | | | 52759 | 126242 | 14268 | 7517 |
| 102 | | | 46720 | 132281 | 10893 | 11049 |
| 103 | | | 47602 | 131399 | 10905 | 16890 |
| 104 | | | 54333 | 124668 | 18417 | 10017 |
| 105 | | | 46699 | 132302 | 10524 | 13928 |
| 106 | | | 50890 | 128111 | 13712 | 12025 |
| 107 | | | 50000 | 129001 | 10652 | 10501 |
| 108 | | | 50659 | 128342 | 10203 | 15584 |
| 109 | | | 56869 | 122132 | 17881 | 7781 |
| 110 | | | 47635 | 131366 | 8276 | 9503 |
| 111 | | | 49747 | 129254 | 11847 | 11253 |
| 112 | | | 50053 | 128948 | 9315 | 6967 |
| 113 | | | 48696 | 130305 | 9998 | 9995 |
| 114 | | | 49695 | 129306 | 11436 | 7769 |
| 115 | | | 47036 | 131965 | 9204 | 7643 |
| 116 | | | 46554 | 132447 | 9071 | 8961 |

TABLE 4-continued

The statistics at each step of the polling process for the first consensus

| Step | SEQ ID NO: | Consensus generated (omitted after 30) | Accepted size | Rejected Size | Newly rejected | Newly returned |
|---|---|---|---|---|---|---|
| 117 | | | 47535 | 131466 | 9866 | 6916 |
| 118 | | | 45681 | 133320 | 6519 | 16195 |
| 119 | | | 56465 | 122536 | 19096 | 9784 |
| 120 | | | 48284 | 130717 | 5765 | 9224 |
| 121 | | | 52886 | 126115 | 11413 | 9706 |
| 122 | | | 52359 | 126642 | 19003 | 2723 |
| 123 | | | 37299 | 141702 | 6838 | 15797 |
| 124 | | | 47494 | 131507 | 13657 | 18342 |
| 125 | | | 53432 | 125569 | 11954 | 7878 |
| 126 | | | 50637 | 128364 | 11854 | 13634 |
| 127 | | | 53716 | 125285 | 11775 | 9234 |
| 128 | | | 52499 | 126502 | 11018 | 11459 |
| 129 | | | 54308 | 124693 | 15627 | 8478 |
| 130 | | | 48544 | 130457 | 15301 | 4729 |
| 131 | | | 39378 | 139623 | 7013 | 16293 |
| 132 | | | 50146 | 128855 | 12080 | 12755 |
| 133 | | | 52331 | 126670 | 11221 | 16356 |
| 134 | | | 58998 | 120003 | 22818 | 10540 |
| 135 | | | 48357 | 130644 | 7920 | 10434 |
| 136 | | | 52526 | 126475 | 15722 | 10780 |
| 137 | | | 49256 | 129745 | 9569 | 5523 |
| 138 | | | 46896 | 132105 | 6868 | 9054 |
| 139 | | | 50775 | 128226 | 8095 | 9594 |
| 140 | | | 53980 | 125021 | 13734 | 4968 |
| 141 | | | 46947 | 132054 | 8485 | 7744 |
| 142 | | | 47956 | 131045 | 13700 | 14683 |
| 143 | | | 50705 | 128296 | 15142 | 8835 |
| 144 | | | 46203 | 132798 | 16167 | 13688 |
| 145 | | | 45583 | 133418 | 11996 | 9840 |
| 146 | | | 45346 | 133655 | 12349 | 16077 |
| 147 | | | 51023 | 127978 | 18671 | 10408 |
| 148 | | | 44751 | 134250 | 9391 | 8322 |
| 149 | | | 45692 | 133309 | 8604 | 12148 |
| 150 | | | 51259 | 127742 | 14748 | 6636 |
| 151 | | | 45187 | 133814 | 8758 | 5601 |
| 152 | | | 44099 | 134902 | 9162 | 12223 |

TABLE 4-continued

The statistics at each step of the polling process for the first consensus

| Step | SEQ ID NO: | Consensus generated (omitted after 30) | Accepted size | Rejected Size | Newly rejected | Newly returned |
|---|---|---|---|---|---|---|
| 153 | | | 49242 | 129759 | 8446 | 9105 |
| 154 | | | 52073 | 126928 | 13358 | 7117 |
| 155 | | | 48035 | 130966 | 14938 | 3586 |
| 156 | | | 38904 | 140097 | 7751 | 9171 |
| 157 | | | 42595 | 136406 | 10721 | 11489 |
| 158 | | | 45649 | 133352 | 13279 | 7927 |
| 159 | | | 42607 | 136394 | 8931 | 10176 |
| 160 | | | 46189 | 132812 | 11630 | 7796 |
| 161 | | | 44705 | 134296 | 8667 | 7355 |
| 162 | | | 45762 | 133239 | 11408 | 12879 |
| 163 | | | 49629 | 129372 | 12977 | 9778 |
| 164 | | | 48918 | 130083 | 13895 | 9467 |

Example 6

Run the Polling Algorithm to Generate the Second Consensus

The remaining 131577 sequences in the rejected set from the last example were used as the input for the second consensus generation. The process stopped when terminated subreads increased from 2689 to 26488, almost ten times. This time the sequence generated matched perfectly to the reverse strand of the amplicon sequence, representing 41808 sequences.

TABLE 5

The statistics at each step of the polling process for the second consensus

| Step | SEQ ID NO: | Consensus (omitted after 30) | Accepted size | Rejected size | Newly rejected | Newly returned |
|---|---|---|---|---|---|---|
| 1 | — | C | 131577 | 0 | 49289 | 0 |
| 2 | — | CT | 82288 | 49289 | 25463 | 0 |
| 3 | — | CTC | 56825 | 74752 | 21285 | 17963 |
| 4 | 48 | CTCG | 53503 | 78074 | 15524 | 9754 |
| 5 | 49 | CTCGC | 47733 | 83844 | 7484 | 28820 |
| 6 | 50 | CTCGCA | 69069 | 62508 | 28852 | 15530 |
| 7 | 51 | CTCGCAA | 55747 | 75830 | 14982 | 11761 |
| 8 | 52 | CTCGCAAG | 52526 | 79051 | 16118 | 10449 |
| 9 | 53 | CTCGCAAGC | 46857 | 84720 | 10305 | 14724 |
| 10 | 54 | CTCGCAAGCA | 51276 | 80301 | 13134 | 24531 |
| 11 | 55 | CTCGCAAGCAC | 62673 | 68904 | 20412 | 8228 |
| 12 | 56 | CTCGCAAGCACC | 50489 | 81088 | 7678 | 15564 |
| 13 | 57 | CTCGCAAGCACCC | 58375 | 73202 | 19113 | 8873 |
| 14 | 58 | CTCGCAAGCACCCT | 48135 | 83442 | 15343 | 7349 |

TABLE 5-continued

The statistics at each step of the polling process for the second consensus

| Step | SEQ ID NO: | Consensus (omitted after 30) | Accepted size | Rejected size | Newly rejected | Newly returned |
|---|---|---|---|---|---|---|
| 15 | 59 | CTCGCAAGCACCCTA | 40141 | 91436 | 7052 | 15067 |
| 16 | 60 | CTCGCAAGCACCCTAT | 48156 | 83421 | 12666 | 12094 |
| 17 | 61 | CTCGCAAGCACCCTA TC | 47584 | 83993 | 6985 | 16338 |
| 18 | 62 | CTCGCAAGCACCCTA TCA | 56937 | 74640 | 20854 | 12471 |
| 19 | 63 | CTCGCAAGCACCCTA TCAG | 48554 | 83023 | 8442 | 8653 |
| 20 | 64 | CTCGCAAGCACCCTA TCAGG | 48765 | 82812 | 10054 | 22863 |
| 21 | 65 | CTCGCAAGCACCCTA TCAGGC | 61574 | 70003 | 24213 | 11845 |
| 22 | 66 | CTCGCAAGCACCCTA TCAGGCA | 49206 | 82371 | 16506 | 10032 |
| 23 | 67 | CTCGCAAGCACCCTA TCAGGCAG | 42732 | 88845 | 8480 | 17900 |
| 24 | 68 | CTCGCAAGCACCCTA TCAGGCAGT | 52152 | 79425 | 14123 | 12569 |
| 25 | 69 | CTCGCAAGCACCCTA TCAGGCAGTA | 50598 | 80979 | 10021 | 13367 |
| 26 | 70 | CTCGCAAGCACCCTA TCAGGCAGTAC | 53944 | 77633 | 11707 | 12493 |
| 27 | 71 | CTCGCAAGCACCCTA TCAGGCAGTACC | 54730 | 76847 | 13884 | 10290 |
| 28 | 72 | CTCGCAAGCACCCTA TCAGGCAGTACCA | 51136 | 80441 | 19186 | 9156 |
| 29 | 73 | CTCGCAAGCACCCTA TCAGGCAGTACCAC | 41106 | 90471 | 9797 | 14231 |
| 30 | 74 | CTCGCAAGCACCCTA TCAGGCAGTACCACA | 45540 | 86037 | 13210 | 12774 |
| 31 | | | 45104 | 86473 | 10417 | 12477 |
| 32 | | | 47164 | 84413 | 13130 | 8108 |
| 33 | | | 42142 | 89435 | 6682 | 16091 |
| 34 | | | 51551 | 80026 | 13131 | 13281 |
| 35 | | | 51701 | 79876 | 11843 | 9937 |
| 36 | | | 49795 | 81782 | 14551 | 8109 |
| 37 | | | 43353 | 88224 | 4394 | 10992 |
| 38 | | | 49951 | 81626 | 9653 | 10094 |
| 39 | | | 50392 | 81185 | 14081 | 5273 |
| 40 | | | 41584 | 89993 | 9273 | 15104 |
| 41 | | | 47416 | 84161 | 12735 | 15665 |
| 42 | | | 50347 | 81230 | 13521 | 10807 |
| 43 | | | 47634 | 83943 | 12232 | 14538 |
| 44 | | | 49941 | 81636 | 14873 | 12238 |

TABLE 5-continued

The statistics at each step of the polling process for the second consensus

| Step | SEQ ID Consensus (omitted after NO: 30) | Accepted size | Rejected size | Newly rejected | Newly returned |
|---|---|---|---|---|---|
| 45 | | 47310 | 84267 | 7422 | 11357 |
| 46 | | 51276 | 80301 | 17354 | 8468 |
| 47 | | 42498 | 89079 | 13542 | 5153 |
| 48 | | 34265 | 97312 | 7361 | 19444 |
| 49 | | 46508 | 85069 | 14340 | 13229 |
| 50 | | 45564 | 86013 | 10745 | 7477 |
| 51 | | 42476 | 89101 | 7418 | 9868 |
| 52 | | 45117 | 86460 | 10444 | 9509 |
| 53 | | 44377 | 87200 | 9559 | 8617 |
| 54 | | 43633 | 87944 | 10191 | 10655 |
| 55 | | 44300 | 87277 | 10099 | 7424 |
| 56 | | 41836 | 89741 | 8976 | 8308 |
| 57 | | 41393 | 90184 | 11097 | 12270 |
| 58 | | 42799 | 88778 | 7688 | 14412 |
| 59 | | 49762 | 81815 | 16040 | 12832 |
| 60 | | 46812 | 84765 | 14967 | 6667 |
| 61 | | 38784 | 92793 | 6814 | 9283 |
| 62 | | 41528 | 90049 | 8077 | 13523 |
| 63 | | 47257 | 84320 | 11887 | 9707 |
| 64 | | 45373 | 86204 | 11723 | 11109 |
| 65 | | 45063 | 86514 | 10714 | 10190 |
| 66 | | 44855 | 86722 | 10635 | 9505 |
| 67 | | 44055 | 87522 | 8962 | 10352 |
| 68 | | 45785 | 85792 | 13688 | 7877 |
| 69 | | 40316 | 91261 | 6442 | 7949 |
| 70 | | 42166 | 89411 | 10535 | 12419 |
| 71 | | 44398 | 87179 | 10874 | 8866 |
| 72 | | 42743 | 88834 | 9433 | 12484 |
| 73 | | 46154 | 85423 | 6677 | 12519 |
| 74 | | 52362 | 79215 | 7606 | 7689 |
| 75 | | 52827 | 78750 | 7146 | 4760 |
| 76 | | 50834 | 80743 | 14193 | 4157 |
| 77 | | 41203 | 90374 | 14703 | 3249 |
| 78 | | 30162 | 101415 | 7814 | 16293 |
| 79 | | 39061 | 92516 | 11324 | 15240 |
| 80 | | 43407 | 88170 | 10665 | 11497 |

TABLE 5-continued

The statistics at each step of the polling process for the second consensus

| Step | SEQ ID Consensus (omitted after NO: 30) | Accepted size | Rejected size | Newly rejected | Newly returned |
|---|---|---|---|---|---|
| 81 | | 44679 | 86898 | 10084 | 11059 |
| 82 | | 46106 | 85471 | 6102 | 11146 |
| 83 | | 51611 | 79966 | 16715 | 6762 |
| 84 | | 42156 | 89421 | 12065 | 4884 |
| 85 | | 35489 | 96088 | 3599 | 19131 |
| 86 | | 51543 | 80034 | 12761 | 8347 |
| 87 | | 47685 | 83892 | 14291 | 4150 |
| 88 | | 38142 | 93435 | 7005 | 13226 |
| 89 | | 44967 | 86610 | 10884 | 10223 |
| 90 | | 44925 | 86652 | 6721 | 6796 |
| 91 | | 45623 | 85954 | 8531 | 11722 |
| 92 | | 49445 | 82132 | 13937 | 8084 |
| 93 | | 44235 | 87342 | 7208 | 9343 |
| 94 | | 47028 | 84549 | 6892 | 16241 |
| 95 | | 57045 | 74532 | 17317 | 7852 |
| 96 | | 48255 | 83322 | 11872 | 6496 |
| 97 | | 43564 | 88013 | 8613 | 8032 |
| 98 | | 43684 | 87893 | 6371 | 10758 |
| 99 | | 48782 | 82795 | 9835 | 8802 |
| 100 | | 48467 | 83110 | 9759 | 8202 |
| 101 | | 47633 | 83944 | 10902 | 9744 |
| 102 | | 47210 | 84367 | 11835 | 9750 |
| 103 | | 45886 | 85691 | 13333 | 11132 |
| 104 | | 44464 | 87113 | 7044 | 11864 |
| 105 | | 50079 | 81498 | 12673 | 9357 |
| 106 | | 47575 | 84002 | 10538 | 4318 |
| 107 | | 42191 | 89386 | 5362 | 13386 |
| 108 | | 51066 | 80511 | 8821 | 8202 |
| 109 | | 51328 | 80249 | 19122 | 3497 |
| 110 | | 36671 | 94906 | 7904 | 7765 |
| 111 | | 37525 | 94052 | 7163 | 18501 |
| 112 | | 49865 | 81712 | 10754 | 11545 |
| 113 | | 51676 | 79901 | 16811 | 8088 |
| 114 | | 44000 | 87577 | 8733 | 8088 |
| 115 | | 44411 | 87166 | 11148 | 12028 |
| 116 | | 46356 | 85221 | 9680 | 8129 |
| 117 | | 45903 | 85674 | 5740 | 13360 |

TABLE 5-continued

The statistics at each step of the polling process for the second consensus

| Step | SEQ ID Consensus (omitted after NO: 30) | Accepted size | Rejected size | Newly rejected | Newly returned |
|---|---|---|---|---|---|
| 118 | | 54632 | 76945 | 13222 | 5479 |
| 119 | | 48013 | 83564 | 13095 | 2910 |
| 120 | | 38962 | 92615 | 5280 | 14109 |
| 121 | | 48931 | 82646 | 11179 | 12921 |
| 122 | | 51822 | 79755 | 12920 | 6550 |
| 123 | | 46612 | 84965 | 8470 | 12408 |
| 124 | | 51737 | 79840 | 16021 | 8535 |
| 125 | | 45473 | 86104 | 16080 | 6694 |
| 126 | | 37326 | 94251 | 9148 | 13840 |
| 127 | | 43284 | 88293 | 12279 | 11998 |
| 128 | | 44288 | 87289 | 7481 | 9448 |
| 129 | | 47548 | 84029 | 16712 | 11273 |
| 130 | | 43420 | 88157 | 9401 | 8686 |
| 131 | | 44039 | 87538 | 10549 | 10398 |
| 132 | | 45252 | 86325 | 11681 | 7452 |
| 133 | | 42402 | 89175 | 13252 | 12448 |
| 134 | | 43004 | 88573 | 8978 | 9704 |
| 135 | | 45147 | 86430 | 7370 | 11084 |
| 136 | | 50302 | 81275 | 12861 | 5168 |
| 137 | | 44065 | 87512 | 7988 | 8605 |
| 138 | | 46150 | 85427 | 10181 | 10613 |
| 139 | | 48080 | 83497 | 12757 | 6971 |
| 140 | | 43804 | 87773 | 11373 | 11609 |
| 141 | | 45575 | 86002 | 11102 | 9298 |
| 142 | | 45321 | 86256 | 10997 | 9291 |
| 143 | | 45177 | 86400 | 11481 | 7816 |
| 144 | | 43090 | 88487 | 8871 | 9371 |
| 145 | | 45190 | 86387 | 9909 | 10369 |
| 146 | | 47274 | 84303 | 7169 | 8117 |
| 147 | | 49863 | 81714 | 11984 | 7030 |
| 148 | | 46559 | 85018 | 8863 | 5573 |
| 149 | | 44935 | 86642 | 11487 | 8142 |
| 150 | | 43294 | 88283 | 9948 | 7906 |
| 151 | | 42987 | 88590 | 10490 | 8716 |
| 152 | | 42979 | 88598 | 12730 | 7147 |
| 153 | | 39175 | 92402 | 8404 | 8161 |

TABLE 5-continued

The statistics at each step of the polling process for the second consensus

| Step | SEQ ID NO: | Consensus (omitted after 30) | Accepted size | Rejected size | Newly rejected | Newly returned |
|---|---|---|---|---|---|---|
| 154 | | | 40737 | 90840 | 9084 | 12699 |
| 155 | | | 46171 | 85406 | 12976 | 6695 |
| 156 | | | 41755 | 89822 | 9695 | 10354 |
| 157 | | | 44312 | 87265 | 11377 | 9028 |
| 158 | | | 43893 | 87684 | 6598 | 8552 |
| 159 | | | 47802 | 83775 | 15583 | 6781 |
| 160 | | | 40975 | 90602 | 7927 | 6816 |
| 161 | | | 41862 | 89715 | 13086 | 12534 |
| 162 | | | 43342 | 88235 | 9618 | 6643 |
| 163 | | | 42523 | 89054 | 11889 | 10580 |
| 164 | | | 43452 | 88125 | 9853 | 8209 |

Example 7

Run the Polling Algorithm on the First 100 Reads from the Data Set

This example took only the first 100 reads with 762 subreads from the data set as the input. The process stopped when terminated subreads changed from 13 to 134. The consensus generated matched perfectly to the amplicon sequence and representing 199 sequences.

TABLE 6

The statistics at each step of the polling process for the first consensus from 100 reads

| Step | SEQ ID NO: | Consensus (omitted after 30) | Accepted size | Rejected size | Newly rejected | Newly returned |
|---|---|---|---|---|---|---|
| 1 | — | C | 762 | 0 | 259 | 0 |
| 2 | — | CT | 503 | 259 | 129 | 0 |
| 3 | — | CTG | 374 | 388 | 180 | 59 |
| 4 | 22 | CTGC | 253 | 509 | 62 | 47 |
| 5 | 19 | CTGCG | 238 | 524 | 49 | 226 |
| 6 | 23 | CTGCGG | 415 | 347 | 212 | 102 |
| 7 | 24 | CTGCGGA | 305 | 457 | 78 | 40 |
| 8 | 25 | CTGCGGAA | 267 | 495 | 48 | 57 |
| 9 | 26 | CTGCGGAAC | 276 | 486 | 79 | 50 |
| 10 | 27 | CTGCGGAACC | 247 | 515 | 58 | 127 |
| 11 | 28 | CTGCGGAACCG | 316 | 446 | 126 | 99 |
| 12 | 29 | CTGCGGAACCGG | 289 | 473 | 101 | 70 |
| 13 | 30 | CTGCGGAACCGGT | 258 | 504 | 75 | 55 |
| 14 | 31 | CTGCGGAACCGGTG | 238 | 524 | 41 | 62 |

TABLE 6-continued

The statistics at each step of the polling process for the first consensus from 100 reads

| Step | SEQ ID NO: | Consensus (omitted after 30) | Accepted size | Rejected size | Newly rejected | Newly returned |
|---|---|---|---|---|---|---|
| 15 | 32 | CTGCGGAACCGGTGA | 259 | 503 | 52 | 64 |
| 16 | 33 | CTGCGGAACCGGTGAG | 271 | 491 | 59 | 65 |
| 17 | 34 | CTGCGGAACCGGTGA GT | 277 | 485 | 76 | 52 |
| 18 | 35 | CTGCGGAACCGGTGA GTA | 253 | 509 | 48 | 52 |
| 19 | 36 | CTGCGGAACCGGTGA GTAC | 257 | 505 | 61 | 68 |
| 20 | 37 | CTGCGGAACCGGTGA GTACA | 264 | 498 | 65 | 136 |
| 21 | 38 | CTGCGGAACCGGTGA GTACAC | 335 | 427 | 146 | 50 |
| 22 | 39 | CTGCGGAACCGGTGA GTACACC | 239 | 523 | 71 | 72 |
| 23 | 40 | CTGCGGAACCGGTGA GTACACCG | 240 | 522 | 104 | 74 |
| 24 | 41 | CTGCGGAACCGGTGA GTACACCGG | 210 | 552 | 56 | 60 |
| 25 | 42 | CTGCGGAACCGGTGA GTACACCGGA | 214 | 548 | 49 | 62 |
| 26 | 43 | CTGCGGAACCGGTGA GTACACCGGAA | 227 | 535 | 29 | 79 |
| 27 | 44 | CTGCGGAACCGGTGA GTACACCGGAAT | 277 | 485 | 90 | 46 |
| 28 | 45 | CTGCGGAACCGGTGA GTACACCGGAATT | 233 | 529 | 34 | 39 |
| 29 | 46 | CTGCGGAACCGGTGA GTACACCGGAATTG | 238 | 524 | 55 | 48 |
| 30 | 47 | CTGCGGAACCGGTGA GTACACCGGAATTGC | 231 | 531 | 44 | 93 |
| 31 | | | 280 | 482 | 83 | 97 |
| 32 | | | 294 | 468 | 117 | 83 |
| 33 | | | 260 | 502 | 71 | 70 |
| 34 | | | 259 | 503 | 55 | 92 |
| 35 | | | 296 | 466 | 93 | 27 |
| 36 | | | 230 | 532 | 45 | 50 |
| 37 | | | 235 | 527 | 63 | 84 |
| 38 | | | 256 | 506 | 79 | 57 |
| 39 | | | 234 | 528 | 63 | 55 |
| 40 | | | 226 | 536 | 57 | 111 |
| 41 | | | 280 | 482 | 140 | 60 |
| 42 | | | 200 | 562 | 29 | 62 |
| 43 | | | 233 | 529 | 67 | 65 |

TABLE 6-continued

The statistics at each step of the polling process for the first consensus from 100 reads

| Step | SEQ ID NO: 30) Consensus (omitted after | Accepted size | Rejected size | Newly rejected | Newly returned |
|---|---|---|---|---|---|
| 44 | | 231 | 531 | 69 | 27 |
| 45 | | 189 | 573 | 40 | 73 |
| 46 | | 222 | 540 | 70 | 77 |
| 47 | | 229 | 533 | 66 | 98 |
| 48 | | 261 | 501 | 69 | 72 |
| 49 | | 264 | 498 | 43 | 50 |
| 50 | | 271 | 491 | 62 | 26 |
| 51 | | 235 | 527 | 46 | 65 |
| 52 | | 254 | 508 | 70 | 62 |
| 53 | | 246 | 516 | 41 | 36 |
| 54 | | 242 | 520 | 38 | 45 |
| 55 | | 250 | 512 | 55 | 28 |
| 56 | | 224 | 538 | 41 | 101 |
| 57 | | 285 | 477 | 76 | 52 |
| 58 | | 262 | 500 | 57 | 55 |
| 59 | | 261 | 501 | 58 | 23 |
| 60 | | 227 | 535 | 49 | 53 |
| 61 | | 232 | 530 | 33 | 90 |
| 62 | | 290 | 472 | 98 | 44 |
| 63 | | 237 | 525 | 89 | 53 |
| 64 | | 202 | 560 | 54 | 98 |
| 65 | | 247 | 515 | 78 | 70 |
| 66 | | 240 | 522 | 46 | 39 |
| 67 | | 234 | 528 | 43 | 66 |
| 68 | | 258 | 504 | 85 | 72 |
| 69 | | 246 | 516 | 88 | 37 |
| 70 | | 196 | 566 | 27 | 67 |
| 71 | | 237 | 525 | 40 | 86 |
| 72 | | 284 | 478 | 76 | 64 |
| 73 | | 273 | 489 | 95 | 58 |
| 74 | | 237 | 525 | 58 | 47 |
| 75 | | 227 | 535 | 32 | 71 |
| 76 | | 267 | 495 | 79 | 40 |
| 77 | | 229 | 533 | 38 | 76 |
| 78 | | 268 | 494 | 77 | 50 |
| 79 | | 243 | 519 | 57 | 27 |
| 80 | | 215 | 547 | 20 | 62 |

TABLE 6-continued

The statistics at each step of the polling process for the first consensus from 100 reads

| Step | SEQ ID Consensus (omitted after NO:30) | Accepted size | Rejected size | Newly rejected | Newly returned |
|---|---|---|---|---|---|
| 81 | | 259 | 503 | 56 | 50 |
| 82 | | 255 | 507 | 54 | 19 |
| 83 | | 222 | 540 | 15 | 43 |
| 84 | | 252 | 510 | 53 | 50 |
| 85 | | 251 | 511 | 70 | 28 |
| 86 | | 211 | 551 | 49 | 88 |
| 87 | | 252 | 510 | 77 | 73 |
| 88 | | 250 | 512 | 63 | 36 |
| 89 | | 225 | 537 | 39 | 39 |
| 90 | | 227 | 535 | 23 | 96 |
| 91 | | 302 | 460 | 85 | 62 |
| 92 | | 281 | 481 | 82 | 28 |
| 93 | | 229 | 533 | 100 | 31 |
| 94 | | 162 | 600 | 54 | 46 |
| 95 | | 156 | 606 | 32 | 110 |
| 96 | | 236 | 526 | 66 | 56 |
| 97 | | 228 | 534 | 52 | 92 |
| 98 | | 270 | 492 | 78 | 57 |
| 99 | | 252 | 510 | 70 | 48 |
| 100 | | 233 | 529 | 51 | 51 |
| 101 | | 236 | 526 | 56 | 41 |
| 102 | | 224 | 538 | 55 | 51 |
| 103 | | 223 | 539 | 54 | 72 |
| 104 | | 244 | 518 | 77 | 45 |
| 105 | | 215 | 547 | 49 | 61 |
| 106 | | 230 | 532 | 54 | 54 |
| 107 | | 233 | 529 | 54 | 47 |
| 108 | | 229 | 533 | 49 | 60 |
| 109 | | 243 | 519 | 83 | 49 |
| 110 | | 213 | 549 | 30 | 37 |
| 111 | | 224 | 538 | 55 | 49 |
| 112 | | 222 | 540 | 39 | 28 |
| 113 | | 215 | 547 | 50 | 55 |
| 114 | | 224 | 538 | 43 | 38 |
| 115 | | 223 | 539 | 45 | 37 |
| 116 | | 219 | 543 | 40 | 33 |

TABLE 6-continued

The statistics at each step of the polling process for the first consensus from 100 reads

| Step | SEQ ID Consensus (omitted after NO: 30) | Accepted size | Rejected size | Newly rejected | Newly returned |
|---|---|---|---|---|---|
| 117 | | 216 | 546 | 37 | 40 |
| 118 | | 224 | 538 | 36 | 80 |
| 119 | | 273 | 489 | 86 | 35 |
| 120 | | 227 | 535 | 23 | 38 |
| 121 | | 247 | 515 | 48 | 36 |
| 122 | | 240 | 522 | 91 | 9 |
| 123 | | 163 | 599 | 27 | 73 |
| 124 | | 214 | 548 | 53 | 90 |
| 125 | | 256 | 506 | 50 | 29 |
| 126 | | 240 | 522 | 43 | 53 |
| 127 | | 256 | 506 | 53 | 40 |
| 128 | | 249 | 513 | 58 | 45 |
| 129 | | 242 | 520 | 72 | 30 |
| 130 | | 206 | 556 | 62 | 17 |
| 131 | | 167 | 595 | 34 | 72 |
| 132 | | 211 | 551 | 49 | 64 |
| 133 | | 232 | 530 | 71 | 67 |
| 134 | | 234 | 528 | 86 | 37 |
| 135 | | 193 | 569 | 36 | 51 |
| 136 | | 216 | 546 | 49 | 54 |
| 137 | | 229 | 533 | 46 | 29 |
| 138 | | 220 | 542 | 32 | 29 |
| 139 | | 225 | 537 | 35 | 47 |
| 140 | | 246 | 516 | 65 | 23 |
| 141 | | 213 | 549 | 34 | 34 |
| 142 | | 222 | 540 | 72 | 54 |
| 143 | | 213 | 549 | 54 | 31 |
| 144 | | 199 | 563 | 62 | 53 |
| 145 | | 199 | 563 | 47 | 43 |
| 146 | | 204 | 558 | 57 | 74 |
| 147 | | 230 | 532 | 77 | 37 |
| 148 | | 199 | 563 | 31 | 34 |
| 149 | | 211 | 551 | 36 | 60 |
| 150 | | 244 | 518 | 76 | 27 |
| 151 | | 204 | 558 | 42 | 26 |
| 152 | | 198 | 564 | 35 | 55 |
| 153 | | 228 | 534 | 30 | 43 |

TABLE 6-continued

The statistics at each step of the polling process for the first consensus from 100 reads

| Step | SEQ ID NO: | Consensus (omitted after 30) | Accepted size | Rejected size | Newly rejected | Newly returned |
|---|---|---|---|---|---|---|
| 154 | | | 251 | 511 | 53 | 31 |
| 155 | | | 239 | 523 | 71 | 18 |
| 156 | | | 196 | 566 | 40 | 31 |
| 157 | | | 197 | 565 | 48 | 52 |
| 158 | | | 211 | 551 | 52 | 36 |
| 159 | | | 205 | 557 | 41 | 54 |
| 160 | | | 228 | 534 | 52 | 22 |
| 161 | | | 208 | 554 | 43 | 32 |
| 162 | | | 207 | 555 | 45 | 42 |
| 163 | | | 214 | 548 | 46 | 49 |
| 164 | | | 227 | 535 | 67 | 39 |

Example 8

Generating the Second Consensus from the First 100 Reads from the Data Set

This example started with 550 subreads left from example 6. The process stopped when terminated subreads changed from 9 to 102. The sequence generated matched perfectly to the reverse strand of the amplicon sequence, representing 174 sequences.

TABLE 7

The statistics at each step of the polling process for the second consensus from 100 reads

| Step | SEQ ID NO: | Consensus (omitted after 30) | Accepted size | Rejected size | Newly rejected | Newly returned |
|---|---|---|---|---|---|---|
| 1 | — | C | 550 | 0 | 203 | 0 |
| 2 | — | CT | 347 | 203 | 99 | 0 |
| 3 | — | CTC | 248 | 302 | 109 | 78 |
| 4 | 48 | CTCG | 217 | 333 | 56 | 45 |
| 5 | 49 | CTCGC | 206 | 344 | 36 | 132 |
| 6 | 50 | CTCGCA | 302 | 248 | 124 | 43 |
| 7 | 51 | CTCGCAA | 221 | 329 | 68 | 55 |
| 8 | 52 | CTCGCAAG | 208 | 342 | 66 | 36 |
| 9 | 53 | CTCGCAAGC | 178 | 372 | 36 | 66 |
| 10 | 54 | CTCGCAAGCA | 208 | 342 | 45 | 86 |
| 11 | 55 | CTCGCAAGCAC | 249 | 301 | 79 | 34 |
| 12 | 56 | CTCGCAAGCACC | 204 | 346 | 38 | 66 |
| 13 | 57 | CTCGCAAGCACCC | 232 | 318 | 81 | 42 |

TABLE 7-continued

The statistics at each step of the polling process for the second consensus from 100 reads

| Step | SEQ ID NO: | Consensus (omitted after 30) | Accepted size | Rejected size | Newly rejected | Newly returned |
|---|---|---|---|---|---|---|
| 14 | 58 | CTCGCAAGCACCCT | 193 | 357 | 57 | 36 |
| 15 | 59 | CTCGCAAGCACCCTA | 172 | 378 | 36 | 63 |
| 16 | 60 | CTCGCAAGCACCCTAT | 199 | 351 | 54 | 39 |
| 17 | 61 | CTCGCAAGCACCCTA TC | 184 | 366 | 18 | 57 |
| 18 | 62 | CTCGCAAGCACCCTA TCA | 223 | 327 | 76 | 60 |
| 19 | 63 | CTCGCAAGCACCCTA TCAG | 207 | 343 | 30 | 32 |
| 20 | 64 | CTCGCAAGCACCCTA TCAGG | 209 | 341 | 41 | 94 |
| 21 | 65 | CTCGCAAGCACCCTA TCAGGC | 262 | 288 | 104 | 47 |
| 22 | 66 | CTCGCAAGCACCCTA TCAGGCA | 205 | 345 | 73 | 35 |
| 23 | 67 | CTCGCAAGCACCCTA TCAGGCAG | 167 | 383 | 31 | 60 |
| 24 | 68 | CTCGCAAGCACCCTA TCAGGCAGT | 196 | 354 | 44 | 59 |
| 25 | 69 | CTCGCAAGCACCCTA TCAGGCAGTA | 211 | 339 | 56 | 59 |
| 26 | 70 | CTCGCAAGCACCCTA TCAGGCAGTAC | 214 | 336 | 44 | 50 |
| 27 | 71 | CTCGCAAGCACCCTA TCAGGCAGTACC | 220 | 330 | 68 | 53 |
| 28 | 72 | CTCGCAAGCACCCTA TCAGGCAGTACCA | 205 | 345 | 69 | 36 |
| 29 | 73 | CTCGCAAGCACCCTA TCAGGCAGTACCAC | 172 | 378 | 48 | 65 |
| 30 | 74 | CTCGCAAGCACCCTA TCAGGCAGTACCACA | 189 | 361 | 53 | 44 |
| 31 | | | 180 | 370 | 51 | 52 |
| 32 | | | 181 | 369 | 45 | 36 |
| 33 | | | 172 | 378 | 29 | 77 |
| 34 | | | 220 | 330 | 57 | 56 |
| 35 | | | 219 | 331 | 65 | 40 |
| 36 | | | 194 | 356 | 56 | 22 |
| 37 | | | 160 | 390 | 8 | 49 |
| 38 | | | 201 | 349 | 45 | 32 |
| 39 | | | 188 | 362 | 51 | 21 |
| 40 | | | 158 | 392 | 30 | 68 |
| 41 | | | 196 | 354 | 51 | 66 |
| 42 | | | 211 | 339 | 55 | 39 |
| 43 | | | 195 | 355 | 45 | 64 |

TABLE 7-continued

The statistics at each step of the polling process for the second consensus from 100 reads

| Step | SEQ ID NO: 30) | Consensus (omitted after | Accepted size | Rejected size | Newly rejected | Newly returned |
|---|---|---|---|---|---|---|
| 44 | | | 214 | 336 | 60 | 39 |
| 45 | | | 193 | 357 | 36 | 36 |
| 46 | | | 194 | 356 | 69 | 34 |
| 47 | | | 161 | 389 | 50 | 23 |
| 48 | | | 136 | 414 | 37 | 69 |
| 49 | | | 170 | 380 | 55 | 53 |
| 50 | | | 170 | 380 | 43 | 41 |
| 51 | | | 170 | 380 | 37 | 37 |
| 52 | | | 172 | 378 | 39 | 36 |
| 53 | | | 171 | 379 | 39 | 36 |
| 54 | | | 170 | 380 | 33 | 51 |
| 55 | | | 190 | 360 | 43 | 29 |
| 56 | | | 178 | 372 | 44 | 31 |
| 57 | | | 167 | 383 | 40 | 42 |
| 58 | | | 171 | 379 | 29 | 64 |
| 59 | | | 208 | 342 | 69 | 57 |
| 60 | | | 198 | 352 | 59 | 41 |
| 61 | | | 182 | 368 | 34 | 32 |
| 62 | | | 182 | 368 | 36 | 41 |
| 63 | | | 189 | 361 | 54 | 40 |
| 64 | | | 177 | 373 | 48 | 57 |
| 65 | | | 188 | 362 | 52 | 50 |
| 66 | | | 188 | 362 | 46 | 27 |
| 67 | | | 171 | 379 | 36 | 43 |
| 68 | | | 180 | 370 | 53 | 31 |
| 69 | | | 160 | 390 | 28 | 30 |
| 70 | | | 164 | 386 | 41 | 57 |
| 71 | | | 182 | 368 | 55 | 37 |
| 72 | | | 166 | 384 | 28 | 56 |
| 73 | | | 196 | 354 | 34 | 65 |
| 74 | | | 229 | 321 | 36 | 25 |
| 75 | | | 220 | 330 | 35 | 20 |
| 76 | | | 207 | 343 | 53 | 18 |
| 77 | | | 174 | 376 | 64 | 14 |
| 78 | | | 126 | 424 | 32 | 56 |
| 79 | | | 152 | 398 | 35 | 71 |

TABLE 7-continued

The statistics at each step of the polling process for the second consensus from 100 reads

| Step | SEQ ID NO: 30) | Consensus (omitted after | Accepted size | Rejected size | Newly rejected | Newly returned |
|---|---|---|---|---|---|---|
| 80 | | | 190 | 360 | 41 | 41 |
| 81 | | | 192 | 358 | 39 | 44 |
| 82 | | | 199 | 351 | 25 | 42 |
| 83 | | | 218 | 332 | 80 | 24 |
| 84 | | | 164 | 386 | 33 | 20 |
| 85 | | | 153 | 397 | 22 | 97 |
| 86 | | | 230 | 320 | 70 | 20 |
| 87 | | | 182 | 368 | 46 | 17 |
| 88 | | | 155 | 395 | 22 | 63 |
| 89 | | | 198 | 352 | 48 | 41 |
| 90 | | | 193 | 357 | 31 | 35 |
| 91 | | | 199 | 351 | 48 | 43 |
| 92 | | | 196 | 354 | 54 | 20 |
| 93 | | | 164 | 386 | 23 | 44 |
| 94 | | | 187 | 363 | 39 | 65 |
| 95 | | | 215 | 335 | 62 | 35 |
| 96 | | | 190 | 360 | 45 | 29 |
| 97 | | | 176 | 374 | 44 | 38 |
| 98 | | | 172 | 378 | 27 | 40 |
| 99 | | | 187 | 363 | 38 | 50 |
| 100 | | | 201 | 349 | 37 | 38 |
| 101 | | | 204 | 346 | 47 | 40 |
| 102 | | | 199 | 351 | 52 | 46 |
| 103 | | | 195 | 355 | 49 | 51 |
| 104 | | | 199 | 351 | 35 | 51 |
| 105 | | | 217 | 333 | 52 | 36 |
| 106 | | | 203 | 347 | 45 | 16 |
| 107 | | | 176 | 374 | 11 | 57 |
| 108 | | | 224 | 326 | 40 | 30 |
| 109 | | | 216 | 334 | 72 | 12 |
| 110 | | | 159 | 391 | 33 | 34 |
| 111 | | | 163 | 387 | 26 | 70 |
| 112 | | | 210 | 340 | 38 | 41 |
| 113 | | | 216 | 334 | 55 | 36 |
| 114 | | | 200 | 350 | 54 | 34 |
| 115 | | | 183 | 367 | 40 | 45 |
| 116 | | | 191 | 359 | 43 | 38 |

TABLE 7-continued

The statistics at each step of the polling process for the second consensus from 100 reads

| Step | SEQ ID Consensus (omitted after NO: 30) | Accepted size | Rejected size | Newly rejected | Newly returned |
|---|---|---|---|---|---|
| 117 | | 189 | 361 | 26 | 47 |
| 118 | | 213 | 337 | 63 | 27 |
| 119 | | 180 | 370 | 45 | 13 |
| 120 | | 152 | 398 | 15 | 74 |
| 121 | | 215 | 335 | 49 | 43 |
| 122 | | 213 | 337 | 52 | 23 |
| 123 | | 188 | 362 | 32 | 50 |
| 124 | | 210 | 340 | 74 | 34 |
| 125 | | 174 | 376 | 56 | 32 |
| 126 | | 154 | 396 | 38 | 74 |
| 127 | | 194 | 356 | 53 | 38 |
| 128 | | 183 | 367 | 24 | 31 |
| 129 | | 194 | 356 | 50 | 51 |
| 130 | | 199 | 351 | 37 | 46 |
| 131 | | 212 | 338 | 53 | 28 |
| 132 | | 191 | 359 | 53 | 25 |
| 133 | | 167 | 383 | 39 | 52 |
| 134 | | 185 | 365 | 36 | 47 |
| 135 | | 201 | 349 | 37 | 33 |
| 136 | | 202 | 348 | 45 | 24 |
| 137 | | 186 | 364 | 33 | 34 |
| 138 | | 192 | 358 | 54 | 43 |
| 139 | | 186 | 364 | 41 | 18 |
| 140 | | 168 | 382 | 31 | 50 |
| 141 | | 192 | 358 | 42 | 36 |
| 142 | | 191 | 359 | 52 | 38 |
| 143 | | 182 | 368 | 48 | 25 |
| 144 | | 164 | 386 | 27 | 38 |
| 145 | | 180 | 370 | 45 | 53 |
| 146 | | 193 | 357 | 23 | 27 |
| 147 | | 203 | 347 | 53 | 46 |
| 148 | | 202 | 348 | 35 | 20 |
| 149 | | 193 | 357 | 58 | 29 |
| 150 | | 170 | 380 | 33 | 25 |
| 151 | | 168 | 382 | 27 | 41 |
| 152 | | 188 | 362 | 54 | 25 |

TABLE 7-continued

The statistics at each step of the polling process for the second consensus from 100 reads

| Step | SEQ ID Consensus (omitted after NO:30) | Accepted size | Rejected size | Newly rejected | Newly returned |
|---|---|---|---|---|---|
| 153 | | 165 | 385 | 35 | 26 |
| 154 | | 162 | 388 | 34 | 52 |
| 155 | | 186 | 364 | 46 | 36 |
| 156 | | 182 | 368 | 48 | 41 |
| 157 | | 181 | 369 | 45 | 26 |
| 158 | | 168 | 382 | 23 | 44 |
| 159 | | 195 | 355 | 69 | 23 |
| 160 | | 155 | 395 | 28 | 24 |
| 161 | | 157 | 393 | 37 | 64 |
| 162 | | 190 | 360 | 42 | 25 |
| 163 | | 179 | 371 | 50 | 35 |
| 164 | | 171 | 379 | 34 | 37 |

The examples and embodiments described herein are for illustrative purposes only. Various modifications or changes thereof are apparent and are included within the spirit and purview of this application and scope of the appended claims. All publications, patents, patent applications, web sites, accession numbers and the like cited herein are hereby incorporated by reference in their entirety for all purposes. If different versions of any such citation are available, the most recent version at the effective filing date of the present application, the effective filing date meaning the filing date of the earliest priority application disclosing the sequence. Unless otherwise apparent from the context, any embodiment, aspect, step, feature, element or the like can be used in combination with any other.

What is claimed is:

1. A method of differentially treating a patient population, comprising;

sequencing samples from members of the patient population; wherein for each sample the sequencing comprises:

(i) ligating a target nucleic acid and an anchor segment of known sequence and thereby forming a nucleic acid target template, which is a circular molecule in which the target nucleic acid forms an adjacent segment adjacent the anchor segment, (ii) generating raw target sequencing reads by synthesis directed by a polymerase reading around the nucleic acid target template multiple times primed from a primer binding to the anchor segment, the raw target sequencing reads comprise alternating reads of the anchor segment and the target nucleic acid; and at least some of the raw target sequencing reads containing sequencing errors; (iii) performing the following computer-implemented steps:

(a) receiving a population of raw target sequencing reads of the nucleic acid target template;

(b) evaluating the accuracy of sequencing of the adapter segment in different raw target sequences by comparing raw target sequencing reads of the anchor segment with the known correct sequence of the adapter segment;

(c) assigning a subset of the raw target sequences into an accepted class based on the accuracy of sequencing of the adapter segment in the raw target sequences;

(d) aligning at least some of the raw target sequences from the accepted class; and (e) determining a sequence of at least part of the adjacent segment from the aligned sequences;

wherein different members of the patient population receive different treatment regimes depending on the determined sequence for the sample from each member.

2. The method of claim 1, wherein step (e) comprises (e1) polling nucleobases at a position equidistant to the anchor segment sequence in raw target sequencing reads in the accepted class to determine a consensus nucleobase, which consensus nucleobase is assigned as the first nucleobase of a nascent sequence of the adjacent segment;

(e2) assigning raw target sequencing reads having the consensus nucleobase determined in the prior polling step to remain in an accepted class and assigning raw target sequencing reads lacking the consensus nucleobase determined in the prior polling step to the rejected class;

(e3) optionally reassigning a raw target sequencing read from the rejected class to the accepted class by scoring similarity of the raw target sequencing read to the nascent sequence and reintroducing the raw target sequencing read if the sequence similarity reaches at least a threshold level of similarity; and (e4) repeating steps (e1), (e2) and optionally (e3), except that a repetition polls a position adjacent the position poled in the previous polling step for raw target sequencing reads having the consensus nucleobase polled in the previous step or in the case of a raw target sequencing read reassigned from the rejected class to the accepted class and not polled in the previous polling step or if polled not having the consensus nucleobase in the previous polling step, the polling polls a position adjacent the position aligned with the last nucleobase of the nascent sequence to determine a consensus nucleobase, and the consensus nucleobases determined in successive repetitions are assigned as successive nucleobases in the nascent sequence of the adjacent segment.

3. The method claim 2, wherein step (e3) is performed at least once.

4. The method of claim 2, wherein step (e4) is performed at least 20 times and step (e3) at least 5 times.

5. The method of claim 2, wherein step (e4) is performed at least 100 times and step (e3) at least 20 times.

6. The method of claim 2, wherein the threshold for step (e3) is at least 80% identity between the raw target sequencing read and nascent sequence when maximally aligned and a match between the last assigned nucleobase of the nascent sequence and corresponding nucleobase of the raw targeting sequencing read.

7. The method of claim 1, wherein the threshold level of accuracy of the sequencing the anchor segment is based on percentage of sequence identity and/or location of matched nucleobases between a raw target sequencing read and the known anchor segment.

8. The method of claim 1, wherein the members of the population are infected with a pathogenic organism and the determined sequence for a member of the population provides information as to type of organisms and/or drug resistance to the organism.

9. The method of claim 1, wherein the determine sequence for a member of the population provides information as to a gene associated with genetic disease, susceptibility or response to infector or response to treatment.

10. The method of claim 1, wherein the determined sequence for a member of the population provides information for a cancer gene fusion.

* * * * *